US007442773B2

(12) United States Patent
Zhao et al.

(10) Patent No.: US 7,442,773 B2
(45) Date of Patent: Oct. 28, 2008

(54) UNIVERSAL PEPTIDE-BINDING SCAFFOLDS AND PROTEIN CHIPS

(75) Inventors: Huimin Zhao, Champaign, IL (US); Olga Esteban, Saragossa (ES)

(73) Assignee: The Board of Trustees of The University of Illinois, Urbana, IL (US)

( * ) Notice: Subject to any disclaimer, the term of this patent is extended or adjusted under 35 U.S.C. 154(b) by 0 days.

(21) Appl. No.: 11/040,686

(22) Filed: Jan. 21, 2005

(65) Prior Publication Data

US 2005/0191706 A1 Sep. 1, 2005

Related U.S. Application Data

(60) Provisional application No. 60/538,959, filed on Jan. 23, 2004.

(51) Int. Cl.

| | |
|---|---|
| ***C07K 16/00*** | (2006.01) |
| ***C12N 1/00*** | (2006.01) |
| ***G01N 33/53*** | (2006.01) |
| ***C40B 20/02*** | (2006.01) |
| ***C40B 30/04*** | (2006.01) |
| ***C40B 40/02*** | (2006.01) |
| ***C40B 40/10*** | (2006.01) |

(52) U.S. Cl. .................. 530/387.1; 435/254.2; 435/7.1; 506/3; 506/9; 506/14; 506/18

(58) Field of Classification Search ............. 530/387.1; 435/254.2, 7.1; 506/3, 9, 14, 18
See application file for complete search history.

(56) References Cited

U.S. PATENT DOCUMENTS

| | | | | |
|---|---|---|---|---|
| 6,300,065 | B1 | 10/2001 | Kieke et al. | |
| 6,391,625 | B1 | 5/2002 | Park et al. | |
| 6,423,538 | B1 | 7/2002 | Wiltrup et al. | |
| 7,049,413 | B2 * | 5/2006 | Zhang et al. | 530/395 |
| 2002/0165149 | A1 * | 11/2002 | Kranz et al. | 514/12 |

FOREIGN PATENT DOCUMENTS

| | | |
|---|---|---|
| WO | WO 01/83827 | 11/2001 |
| WO | WO 02/054070 | 7/2002 |

OTHER PUBLICATIONS

Adams et al. (1983) "Production and Characterization of Monoclonal Antibodies Recognizing the α-Chain Subunits of Human la Alloantigens," *Immunol.* 50:613-624.

Arnold (2001) "Combinatorial and Computational Challenges for Biocatalyst Design," *Nature* 409:253-257.

Arnold (1998) "Design by Directed Evolution," *Acc. Chem. Res.* 31:125-131.

Bertoletti et al. (1994) "Natural Variants of Cytotoxic Epitopes are T-Cell. Receptor Antagonists for Antiviral Cytotoxic T Cells," *Nature* 369:407-410.

Boder et al. (2000) "Yeast Surface Display for Directed Evolution of Protein Expression, Affinity, and Stability," *Methods Enzymol.* 328:430-444.

Boder et al. (2000) "Directed Evolution of Antibody Fragments with Monovalent Femtomolar Antigen-Binding Affinity," *Proc. Natl. Acad. Sci. USA* 97:10701-10705.

Boder et al. (1998) "Optimal Screening of Surface-Displayed Polypeptide Libraries," *Biotechnol Prog.* 14:55-62.

Boder et al. (1997) "Yeast Surface Display for Screening Combinatorial Polypeptide Libraries," *Nature Biotehcnol.* 15:553-557.

Burley et al. (1986) "Amino-Aromatic Interactions in Proteins," *FEBS Lett.* 203:139-143.

Burley et al. (1988) "Weakly Polar Interactions in Proteins," *Adv. Protein Chem.* 39:125-189.

Busch et al. (1990) "Detection of Peptide-MHC Class II Complexes on the Surface of Intact Cells," *J. Immunol. Methods* 134:1-22.

Butler et al. (2003) "Functional Expression of a Fungal Laccase in *Saccharomyces cerevisiae* by Directed Evolution," *Appl. Environ. Microbiol.* 69(2):987-995.

Buus (1999) "Description and Prediction of Peptide-MHC BindingL The 'Human MHC Project'," *Curr. Opin. Immunol.* 11(2):209-213.

Cahill (2001) "Protein and Antibody Arrays and Their Medical Applications," *J. Immunol. Methods* 250:81-91.

Casares et al. (2002) Down-Regulation of Diabetogenic CD4+ T Cells by a Soluble Dimetric Peptide-MHC Class II Chimera, *Nature. Immunol.* 3:383-391.

Chang et al. (2001) Design, Engineering, and Production of Human Recombinant T Cell Receptor Ligands Derived from Human Leukocyte Antigen DR2, *J. Biol. Chem.* 276:24170-24176.

Crameri et al. (1998) "Dna Shuffling of a Family of Genes from Diverse Species Accelerates Directed Evolution," *Nature* 391:288-291.

De Wildt et al. (2000) "Antibody Arrays for High-Throughput Screening of Antibody-Antigen Interactions," *Nature Biotechnol.* 18(9):989-994.

Doebele et al. (2003) "Point Mutations in or Near the Antigen-Binding Groove of HLA-DR3 Implicate Class II-Associated Invariant Chain Peptide Affinity as a Constraint on MHC Class II Polymorphism," *J. Immunol.* 170:4683-4692.

Emili et al. (2000) "Large Scale Functional Analysis Using Peptide or Protein Arrays," *Nature Biotechnology.* 18(4):393-397.

Esteban et al. (2004) "Directed Evolution of Soluble Single-chain Human Class II MHC Molecules," *J. Mol. Biol.* 340:81-95.

Esteban et al. (2004) "Directed Evolution of Functional Single-Chain HLA-DR1 Molecules," Poster—Symposium on the Evolution of Biomolecular Structure, Michigan State University, East Lansing, Michigan, Jun. 4, 2004.

(Continued)

*Primary Examiner*—Jon D. Epperson
*Assistant Examiner*—Amber D. Steele
(74) *Attorney, Agent, or Firm*—Greenlee, Winner and Sullivan, P.C.

(57) ABSTRACT

The present invention provides a universal peptide-binding scaffold. This scaffold is used to bind a target. The target can be a peptide or peptides of interest (for example, peptides associated with a disease state) or can represent the entire proteome. The target can be either protein fragments prepared by enzymatic digestion of the entire proteome or N- or C-terminal short sequences exposed by chemical denaturation of the entire proteome (unfolded proteins). The universal peptide-binding scaffold can be tailored to specifically bind a target using the methods described herein.

14 Claims, 16 Drawing Sheets

OTHER PUBLICATIONS

Esteban et al. (2003) "Directed Evolution of Functional Single-Chain HLA-DR1 Molecules," Abstract—The Protein Society 17th Annual Symposium, Boston, Jul. 27, 2003.
Feldhaus et al. (2003) "Flow-Cytometric Isolation of Human Antibodies From a Nonimmune *Saccharomyces cerevisiae* Surface Display Library," *Nature. Biotechnol.* 21:163-170.
Ferlin et al. (2000) "Present Difficulties and Future Promise of MHC Multimers in Autoimmune Exploration," *Curr. Opin. Immunol.* 12:670-675.
Frayser et al. (1999) "Empty and Peptide-Loaded Class II Major Histocompatibility Complex Proteins Produced by Expression in *Escherichia coli* and Folding in Vitro," *Protein Expr. Purif.* 15:105-114.
Garboczi et al. (1992) "HLA-A2-Peptide Complexes: Refolding and Crystallization of Molecules Expressed in *Escerichia coli* and Complexed with Single Antigenic Peptides," *Proc. Natl. Acad. Sci. USA* 89(8):3429-3433.
Garboczi et al. (1994) "Five Viral Peptide-HLA-A2 Co-Crystals. Simultaneous Space Group Determination and X-ray Data Collection," *J. Mol. Biol.* 239(4):581-587.
Gietz et al. (2002) "Transformation of Yeast by Lithium Acetate/Single-Stranded Carrier DNA/Polyethylene Glycol Method," *Methods in Enzymology* 350:87-96.
Gygi et al. (1999) "Quantitative Analysis of Complex Protein Mixtures Using Isotope-Coded Affinity Tags," *Nature Biotechnol.* 17(10):994-999.
Hackett et al. (2002) "Frontiers in Peptide-MHC Class II Multimer Technology," *Nature Immunol.* 3:887-889.
Hammond et al. (1994) "Quality Control in the Secretory Pathway: Retention of a Misfolded Viral Membrane Glycoprotein Involves Cycling Between the ER, Intermediate Compartment, and Golgi Apparatus," *J. Cell. Biol.* 126:41-52.
Holler et al. (2000) "In vitro Evolution of a T Cell Receptor with High Affinity for Peptide/MHC," *Proc, Natl. Acad. Sci. USA* 97:5387-5392.
Horton et al. (1993) Gene Splicing by Overlap Extension, *Methods Enzymol.* 217:270-279.
Jain et al. (1988) "Mechanisms of Heterogeneous Distribution of Monoclonal Antibodies and Other Macromolecules in Tumors: Significance of Elevated Interstitial Pressure," *Cancer Res.* 48:7022-7032.
Joshi et al. (2000) "A Three-Step Kinetic Mechanism for Peptide Binding to MHC class II Proteins," *Biochem.* 39:3751-3762.
Kalandadze et al. (1996) "Expression of Recombinant HLA-DR2 Molecules," *J. Biol. Chem.* 271:20156-20162.
Kieke et al. (2001) High Affinity T Cell Receptors from Yeast Display Libraries Block T Cell Activation by Superantigens *J. Mol. Biol.* 307:1305-1315.
Kieke et al. (1999) "Selection of Functional T Cell Receptor Mutants from a Yeast Surface-Display Library," *Proc. Natl. Acad. Sci. USA* 96:5651-5656.
Kieke et al. (1997) "Isolation of Anti-T Cell Receptor scFv Mutants by Yeast Surface Display," *Protein Eng.* 10:1303-1310.
Klenerman et al. (1994) "Cytotoxic T-Cell Activity Antagonized by Naturally Occurring HIV-1 Gag Variants," *Nature* 369:403-407.
Kozono et al. (1994) "Production of Soluble MHC Class II Proteins with Covalently Bound Single Peptides," *Nature* 369:151-154.
Kwok et al. (2002) "Use of Class II Tetramers for Identification of CD4+ T Cells," *J. Immunol. Methods* 268:71-81.
LaPan et al. (1992) "Production and Characterization of Two New Mouse Monoclonal Antibodies Reactive with Denatured Mouse Class II Beta Chains," *Hybridoma* 11(2):217-223.
Leary (1994) "Strategies for Rare Cell Detection and Isolation," *Methods Cell Biol.* 42(B):331-358.
Lin et al. (1999) "Functional Expression of Hoseradish Perixidase in *E. coli* by Directed Evolution," *Biotechnol. Prog.* 15:467-471.
Madden et al. (1993) "The Antigenic Identity of Peptide-MHC Complexes: A Comparison of the Conformations of Five Viral Peptides Presented by HLA-A2," *Cell* 75:693-708.
Madden (1995) "The Three-Dimensional Structure of Peptide-MHV Complexes," *Ann. Rev. Immunol.* 13:587-622.
Maile et al. (2001) Antigen-Specific Modulation of an Immune Response by In Vivo Administration of Soluble MHC Class I Tetramers, *J. Immunol.* 167:3708-3714.
Masteller et al. (2003) "Peptide-MHC Class II Dimers as Therapeutics to Modulate Antigen-Specific T Cell Responses in Autoimmune Diabetes," *J. Immunol.* 171:5587-5595.
Mitchell et al. (2002) "A Perspective on Protein Microarrays," *Nature Biotechnol* . 20:225-229.
Musacchio et al. (1992) "SH3 an Abundant Protein Domain in Search of a Function," *FEBS* 307(1):55-61.
Natarajan et al. (1999) "Stable Peptide Binding to MHC Class II Molecule Is Rapid and is Determined by a Receptive Conformation Shaped by Prior Association with Low Affinity Peptides," *J. Immunol.* 162:4030-4036.
Oldenburg et al. (1997) "Recombination-Mediated PCR-Directed plasmid Construction in vivo in Yeast," *Nuc. Acid Res.* 25:451-452.
Orr et al. (2003) "Rapid Method for Measuring ScFv Thermal Stability by Yeast Surface Display," *Biotechnol Prog.* 19:631-638.
Pandey et al. (2000) "Proteomics to Study Genes and Genomes," *Nature* 405:837-846.
Pedelacq et al. (2002) "Engineering Soluble Proteins for Structural Genomics," *Nature. Biotechnol.* 20:927-932.
Pinilla et al. (1999) Exploring Immunological Specificity Using Synthetic Peptide Combinatorial Libraries, *Curr. Opin. Immunol.* 11(2):193-202.
Ponting, C.P. (1997) "Evidence for PDZ Domains in Bacteria, Yeast, and Plants," *Protein Sci.* 6(2):464-468.
Prado et al. (1994) "New In-Vivo Cloning Methods by Homologous Recombination in Yeast," *Curr. Genet.* 25:180-183.
Reid et al. (1985) "Sulphur-Aromatic Interactions in Proteins," *FEBS Lett.* 190:209-213.
Robinson et al. (2003) "IMGT/HLA and IMGT/MHC: Sequence Databases for the Study of the Major Histocompatibility Complex," *Nuc. Acid Res.* 31(1):311-314.
Russell et al. (1992) "Conservation Analysis and Structure Prediction of the SH2 Family of Phosphotyrosine Bonding Domains," *FEBS Lett.* 304(1):15-20.
Santambrogio et al. (1999) "Abundant Empty Class II MHC Molecules on the Surface of Immature Dendritic Cells," *Proc. Natl.Acad. Sci. USA* 96:15050-15055.
Sato et al. (1999) "Substitution of Aspartic Acid at B57 with Alanine Alters MHC Class II Peptide Binding Activity but Not Protein Stability: HLA-DQ (α1*0201, β1*0302) and (α1*0201, β1*0303)," *Hum. Immunol.* 60:1227-1236.
Sato et al. (2000) "Determinants of the Peptide-Induced Conformation Change in the Human Class II Major Histocompatibility Complex Protein HLA-DR1," *J. Biol. Chem.* 275:2165-2173.
Scheirle et al. (1992) "Peptide Binding to Soluble HLA-DR4 Molecules Produced by Insect Cells," *J. Immunol.* 149(6):1994-1999.
Schneider et al. (1999) "Mutagenesis and Selection of PDZ Domains that Bind New Protein Targets," *Nature Biotechnol.* 17(2):170-175.
Schweickhardt et al. (2003) "Structure-Expression Relationship of Tumor Necrosis Factor Receptor Mutants That Increase Expression," *J. Biol. Chem.* 278:28961-28967.
Schmidt-Dannert (2001) "Directed Evolution of Single Proteins, Metabolic Pathways, and Viruses," *Biochem.* 40(44):13125-13136.
Scott et al. (1996) "Role of Chain Pairing for the Production of Functional Soluble IA Major Histocompatibility Complex Class II Molecules," *J. Exp. Med.* 183:2087-2095.
Sharma et al. (1991) "Antigen-Specific Therapy of Experimental Allergic Encephalomyelitis by Soluble Class II Major Histocompatibility Complex-Peptide Complexes," *Proc. Natl. Acad. Sci. USA* 88:11465-11469.
Shusta et al. (1998) "Increasing the Secretory Capacity of *Saccharomyces cerevisiae* for Production of Single-Chain Antibody Fragments," *Nature Biotechnol.* 16:773-777.
Shusta et al. (2000) "Directed evolution of a stable scaffold for T-cell receptor engineering," *Nature Biotechnol.* 18:754-759.
Shusta et al. (1999) "Yeast Polypeptide Fusion Surface Display Levels Predict Thermal Stability and Soluble Secretion Efficiency," *J. Mol. Biol.* 292(5):949-956.

Singh et al. (1997) "Infectious Diseases and Immunity: Special Reference to Major Histocompatibility Complex," *Emerging Infectious Diseases* 3:41-49.

Stanfield et al. (1995) "Protein-Peptide Interactions," *Curr. Opin. Struct. Biol.* 5(1):103-113.

Starwalt et al. (2003) "Directed Evolution of a Single-Chain Class II MHC Product by Yeast Display," *Prot. Eng.* 16:147-156.

Stern et al. (1994) "Crystal Structure of the Human Class II MHC Protein HLA-DR1 Complexed with an Influenza Virus Peptide," *Nature* 368:215-221.

Stern et al. (1992) "The Human Class II MHC Protein HLA-DR1 Assembles as Empty αβ Heterodimers in the Absence of Antigenic Peptide," *Cell* 68(3):465-477.

Strominger et al. (1995) "The Class I and Class II Proteins of the Human Major Histocompatibility Complex," *JAMA* 274(13):1074-1076.

Tissot et al. (2000) "Viral Escape at the Molecular Level Expanded by Quantitative T-Cell Receptor/Peptide/MHC Interactions and the Crystal Structure of a Peptide/MHC Complex," *J. Mol. Biol.* 302:873-875.

Tiwari et al. (1981) "HLA-DR and Disease Associations," *Prog. Clin. Biol. Res.* 58:151-163.

Todd et al. (1987) "HLA-$DQ_\beta$ Gene Contributes to Susceptibility and Resistance to Insulin-Dependent Diabetes Mellitus," *Nature* 329:599-604.

Townsend et al. (1986) "The Epitopes of Influenza Nucleoprotein Recognized by Cytotoxic T Lymphocytes can be Defined with Short Sythetic Peptides," *Cell* 44(6):959-968.

Ueda et al. (2000) "Genetic Immobolization of Proetins on the Yeast Cell Surface," *Biotechnol. Adv.* 18:121-140.

VanAntwerp et al. (2000) "Fine Affinity Discrimination Yeast Surface Display and Flow Cytometry," *Biotechnol. Prog.* 16:31-37.

van der Burg et al. (1996) "Immunogenicity of Peptides Bound to MHC Class I Molecules Depends on the MHC-Peptide Complex Stability," *J. Immunol.* 156:3308-3314.

Waldburger et al. (1996) "Barriers to Protein Folding: Formation of Buried Polar Interactions is a Slow Step in Acquisition of Structure," *Proc. Natl. Acad. Sci. USA* 93:2629-2634.

Waldo (2003) "Genetic Screens and Directed Evolution for Protein Solubility," *Curr. Opin. Chem. Biol.* 7:33-38.

Wittrup (2001) "Protein Engineering by Cell-Surface Display," *Curr. Opin Biotechnol.* 12:395-399.

Yeung et al. (2002) "Quantitative Screening of Yeast Surface-Displayed Polypeptide Libraries by Mangetic Bead Capture," *Biotechnol. Prog.* 18:212-220.

Zauhar et al. (2000) "Evidence for a Strong Sulfur-Aromatic Interaction Derived from Crystallographic Data," *Biopolymers* 53:233-248.

Zhao et al. (1999) "Methods for Optimizing Industrial Enzymes by Directed Evolution," In: *Manual of Industrial Microbiology and Biotechnology*, 2 nd Ed., Demain et al., eds., ASM Press, Washington, DC, pp. 597-604.

Zhao et al. (1998) "Molecular Evolution by Staggered Extension Process (StEP) in vitro Recombination," *Nature. Biotechnol.* 16:258-261.

Zhao et al. (2001) "Interaction of α-Agglutinin and a-Agglutinin, *Saccharomyces cerevisiae* Sexual Cell Adhesion Molecules," *J. Bacteriol.* 183:2874-2880.

Zhu et al. (1997) "A Recombinant Single-Chain Human Class II MHC Molecule (HLA-DR1) as a Covalently Linked Heterotrimer of α Chain, β Chain, and Antigenic Peptide, with Immunogenicity In Vitro and Reduced Affinity for Bacterial Superantigens," *Eur. J. Immunol.* 27(8):1933-1941.

Zhu et al. (2001) "Global Analysis of Protein Activities Using Proteome Chips," *Science* 293:2101-2105.

* cited by examiner

UNIVERSAL PEPTIDE-BINDING SCAFFOLDS AND PROTEIN CHIPS

CROSS-REFERENCE TO RELATED APPLICATIONS

This application claims priority to U.S. provisional application 60/538,959, filed Jan. 23, 2004, which is hereby incorporated by reference to the extent not inconsistent with the disclosure herewith.

BACKGROUND OF THE INVENTION

Proteomic research is the study of all proteins in an organism and is expected to lead to discoveries leading to improved diagnosis and treatment of disease. One problem inherent in proteomics research is the requirement of a high throughput analysis of a large number of proteins. The most widely used protein analysis method is based on 2-D gel electrophoresis and mass spectrometry in which proteins are first separated on gels according to charge and size, and then identified by mass spectrometers. An alternative analysis method is based on isotopic labeling such as isotope-coded affinity tags (ICAT) and tandem mass spectrometry in which no protein separation is needed. Another analysis method is based on protein chips in which thousands of "bait" proteins such as antibodies are immobilized in an array format onto specially treated surfaces. Compared to the other two methods, protein chips have the advantage of being scalable, and their organized nature enables high throughput screening using robotic, imaging, or analytical methods. Protein chips are powerful tools for the genome-scale analysis of gene function, such as enzyme activity, protein-protein, protein-DNA, protein-RNA, and protein-ligand interactions, directly on the protein level. The main limitation in developing protein chips is the lack of a universal peptide-binding scaffold to create tailor-made protein capturing reagents that specifically bind to every single protein in a given organism.

Because of their high specificity and affinity to proteins, monoclonal antibodies have been widely considered for use as protein capturing reagents of choice for protein chips. Several antibody-based low-density protein chips have been developed. However, generation of specific antibodies for each protein remains a time-consuming and expensive challenge. In particular, the preparation of monoclonal antibodies requires the availability of thousands of purified soluble proteins which are difficult to obtain in large scale. In addition, the stability of immobilized antibodies is a concern. Therefore, non-antibody based protein capturing reagents that can be tailored to specifically bind to a target peptide are desired. Ideally, such reagents should have high stability, similar or better specificity and affinity as antibodies, and the reagents should be able to be prepared on a large scale.

BRIEF SUMMARY OF THE INVENTION

The present invention provides a universal peptide-binding scaffold. This scaffold is used to bind a target. A universal peptide-binding scaffold is a library of mutants of a universal peptide binding domain. A "mutant" is a naturally-occurring or wild-type peptide or protein with one or more amino acid substitutions from the naturally-occurring amino acid sequence. A "library" is a collection of more than one mutant. A "binding domain" is a minimum sequence having specific binding. The target can be a peptide or peptides of interest (for example, peptides associated with a disease state) or can be the entire proteome. The target includes protein fragments prepared by enzymatic digestion of the entire proteome and N- or C-terminal short sequences formed by chemical denaturation of the entire proteome (unfolded proteins). The universal peptide-binding scaffold can be tailored to specifically bind a target using the methods described herein. "Specific" binding between the universal peptide-binding scaffold and a target means the target binds only to the universal peptide-binding scaffold, within current detection abilities.

The universal peptide binding domain is selected from the group consisting of: SH2 domains, SH3 domains, PDZ domains, MHC class I peptide binding domains and MHC class II peptide binding domains. Any individual member or combination of members of the universal peptide binding domains listed forms a particular class of the invention. The universal peptide binding scaffold of the invention is formed using the description provided herein. The mutants of the universal peptide binding domain are formed using the description provided herein. One specific example is display of the mutants using yeast display system. One specific example is a mutant of MHC II having one or more amino acid alterations at positions where it is known yeast display of the mutant leads to correct conformation.

Also provided is a method of selecting proteins or peptides that bind to a universal peptide binding scaffold comprising: preparing a universal peptide binding scaffold; contacting said scaffold with labeled proteins or peptides of interest; and selecting those mutants from the scaffold that bind to the labeled proteins or peptides of interest with a desired affinity. The desired affinity is determined by the purposes of the experiment. Some desired affinities range from micromolar to subnanomolar, including all individual values and intermediate ranges therein, including $10^{-6}$ molar to $10^{-7}$ molar; $10^{-7}$ molar to $10^{-8}$ molar; $10^{-8}$ molar to $10^{-9}$ molar; $10^{-6}$ molar to $10^{-8}$ molar; and $10^{-7}$ molar to $10^{-9}$ molar.

Also provided is a protein chip comprising mutants of a universal peptide-binding domain bound to a substrate. These mutants may be bound to the substrate in patterns that facilitate analysis, as known in the art. Methods of forming patterns of substrates on chips are known in the art. Methods of analyzing protein chips for a desired binding interaction are known in the art, and include tagging one component with a label, such as a fluorescent label, and analyzing the protein chip for the presence of the label, the presence thereof indicates the label is bound to the material on the substrate. The substrate can be any composition known in the art and is preferably selected from the group consisting of: glass, polycarbonate, polytetrafluoroethylene, polystyrene, silicon oxide and silicon nitride.

As used herein, "protein" refers to a full-length protein, portion of a protein, or peptide. Proteins can be prepared recombinantly in an organism, preferably bacteria, yeast, insect cells or mammalian cells, or produced via fragmentation of larger proteins, or chemically synthesized.

As used herein, "functional domain" is a domain of a protein which is necessary and sufficient to give a desired functional activity. Examples of functional domains include domains which exhibit binding activity towards DNA, RNA, protein, hormone, ligand or antigen. A binding domain is one example of a functional domain.

DETAILED DESCRIPTION OF THE INVENTION

The single-chain Class II MHC molecule binding site is described herein as an example of the binding domain used in the universal peptide-binding scaffold, however, other universal peptide-binding domains may be used in the universal peptide-binding scaffold, including SH2 domains, SH3 domains, PDZ domains, and MHC class I peptide binding domains, as known in the art, using the disclosure herewith.

The sequences of each of the domains are discussed in the following references: SH2 domain: "Conservation analysis and structure prediction of the SH2 family of phosphotyrosine binding domains." Russell R B, Breed J, Barton G J, FEBS Lett. 1992, 304(1):15-20; SH3 domain: "SH3—an abundant protein domain in search of a function." Musacchio A, Gibson T, Lehto V P, Saraste M. FEBS Lett. 1992, 307(1): 55-61; PDZ domain: "Evidence for PDZ domains in bacteria, yeast, and plants." Ponting C P. Protein Sci. 1997, 6(2):464-8; MHC class I: the HLA-A2 sequence is provided here.

Human major histocompatibility complex (MHC) class II molecules are membrane-anchored heterodimers that bind and present peptides on the surface of antigen presenting cells to T cells in a cell-mediated immunity. MHC molecules are major contributors to the genetic susceptibility underlying autoimmune diseases, cancer and infectious diseases. For example, MHC class II molecule HLA-DR1 and HLA-DR4 are associated with rheumatoid arthritis while HLA-DR2 is associated with multiple sclerosis. Because of their important biological role in immune responsiveness, MHC proteins have attracted great attention as a new class of diagnostic and therapeutic agents. For example, the MHC-peptide complexes may be used to detect a variety of antigen-specific T cells in human blood or to induce antigen-specific autoreactive T cell unresponsiveness in human autoimmune diseases. The high specificity and affinity between the peptide and the MHC molecule and the stability of the peptide-complex are often considered to be prerequisite for successful development of MHC-based diagnostic and therapeutic agents or MHC-based peptide capturing agents for a protein chip. Unfortunately, it is very difficult to obtain soluble functional MHC molecules for characterization and protein engineering, in particular, in a system amenable to powerful combinatorial protein design approaches such as directed evolution.

Figure 1:
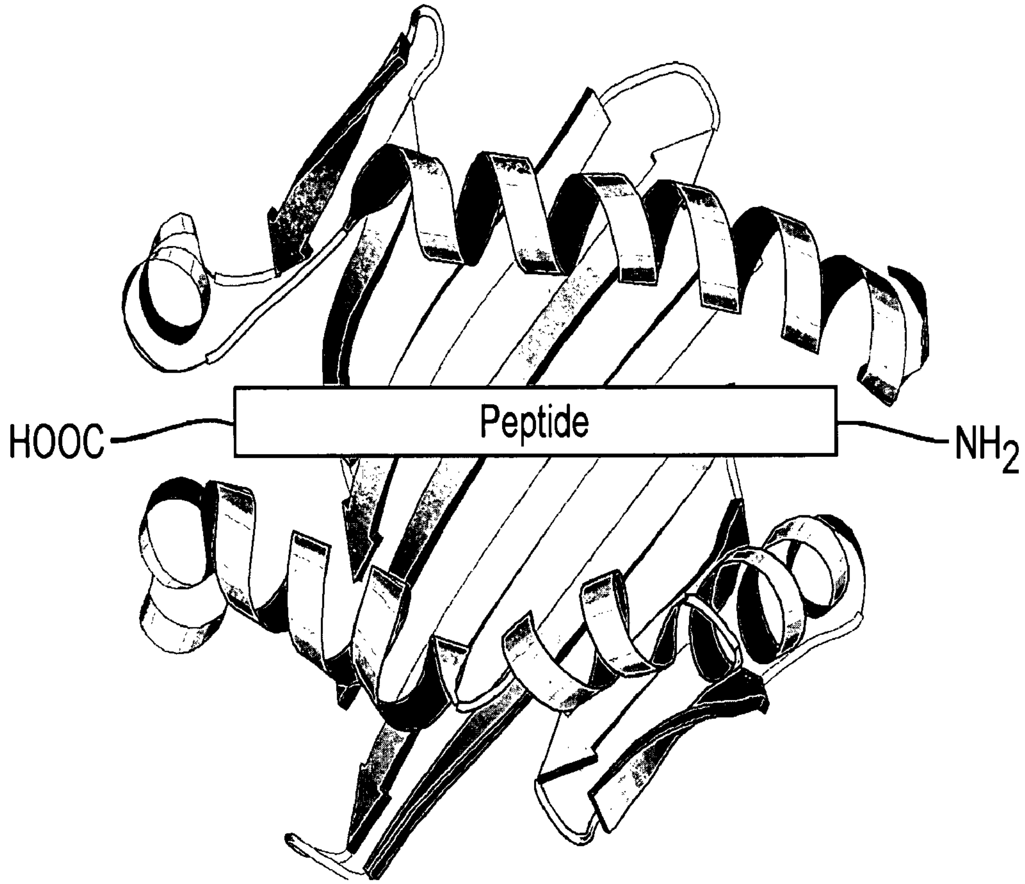
FIG. 1 shows the peptide-binding site of MHC molecules.

The use of MHC molecules as universal peptide-binding scaffolds have several practical advantages over other universal peptide-binding scaffolds. MHC molecules are used in nature for peptide recognition and discrimination in the immune system. MHC molecules can capture peptides from the cellular environment and present these peptides for scrutiny by immune cells. MHC molecules are extremely polymorphic with distinct specificities, suggesting the versatility of these molecules for peptide recognition. Several hundred different MHC molecules have been found within the human species and their nucleotide sequences are available. Crystallographic studies of the MHC molecules have revealed a common overall structure, featuring a unique peptide-binding site situated at the outer domains. The peptide-binding site consists of two long α-helices and an eight-stranded antiparallel β-sheet (groove-like structure, see FIG. 1). For class I MHC molecules, the binding site is formed as intrachain dimer of the α1 and α2 domains. For class II MHC molecules, the binding site is formed as interchain dimer of the α1 and β1 domains. Not surprisingly, the polymorphic residues are all concentrated along the peptide-binding site that determines the MHC specificity. A given peptide-binding groove can bind hundreds or thousands of different peptides, identical or homologous at only a few side chain positions. Nonetheless, the typical dissociation constant between a peptide antigen and a MHC molecule ranges from micromolar to nanomolar. Much of the binding energy comes from the interactions between the peptide main chain and MHC molecules (sequence-independent) while the interactions between the peptide side-chains (i.e. sequence) and MHC molecules accounts for the specificity.

The peptide binding groove of class II MHC molecules is open, allowing peptides of 10-25 amino acids in length to bind. The readily accessible N- and C-termini provide handles for convenient and universal chemical labeling. Unlike class I MHC molecules, functional class II MHC molecules have been produced in an empty, peptide-free form, suggesting the peptide-binding site can be formed without loaded peptides. This is desirable because the peptide-free functional class II MHC molecules are ready to bind a peptide as they are made.

In vitro evolution or directed evolution methods of the universal peptide-binding scaffold were used here to mimic the process of natural evolution in the test tube, involving repeated cycles of creating molecular diversity by random mutagenesis and gene recombination and screening/selecting the functionally improved variants. The power of in vitro evolution mainly lies in its use of a combinatorial algorithm to rapidly search and accumulate beneficial mutations from libraries containing a large number of different variants. Unlike rational design, in vitro evolution does not require extensive structural and mechanistic information on the biomolecules.

The universal peptide-binding scaffold of the invention is useful in all applications where antibodies are useful, for example, use as a diagnostic agent, therapeutic agent or research agent for protein purification and western blotting.

Directed evolution and yeast surface display were used to express mutants of human MHC class II molecule HLA-DR1 on the yeast cell surface that are properly folded and can bind specific antigenic peptides. This system can be used for further engineering of the affinity and specificity of peptide binding to DR1 molecules by powerful directed evolution approaches. Briefly, in vitro evolution experiments were focused on the peptide-binding site of HLA-DR1 consisting of α1 and β1 domains (~180 residues). Genetic variations were introduced within this site using two distinct DNA diversification approaches. The first approach is to randomly introduce multiple amino acid substitutions using error-prone PCR. The second approach was to create different combinations of naturally existing mutations (polymorphism) among a set of homologous MHC genes using family shuffling. Genes encoding classical HLA molecules are extremely polymorphic, with most genes consisting of a large number of allelic variants specifying differences at the amino acid level and fine structural detail. The HLA IMGT/HLA database currently includes 1524 HLA allelic sequences (904 HLA I alleles and 620 HLA II alleles) (release 1.16, Oct. 14, 2002 "IMGT/HLA and IMGT/MHC: sequence databases for the study of the major histocompatibility complex" Nucleic Acids Res. 2003 Jan. 1; 31(1):311-4). The number of HLA allelic variants that diverge in at least one amino acid residue varies for the individual HLA genes, being greatest for HLA-B and DRB1 genes with 447 and 271 variants, respectively. The three HLA class II genes (HLA-DP, HLA-DQ, and HLA-DR) share more than 60% sequence identity whereas allelic sequences within the same gene, e.g. HLA-DR, share more than 90% identity. Family shuffling often creates a library of chimerical genes that has much richer functional diversity than error-prone PCR or DNA shuffling, allowing rapid improvement of desired protein functions. The co-transformation of mutated target gene products and the linear vector digested with two unique restriction sites into the yeast cells results in the cloning and expression of variants of the peptide-binding scaffold on the yeast cell surface.

The following nonlimiting examples are intended to further explain and illustrate the invention. The description below specifically describes expression of single-chain class II MHC HLA-DR1 and class I HLA-A2 molecules on a yeast cell surface and the use of in vitro evolution methods to rapidly create a variant of the scaffold that specifically binds to a given target peptide. Although yeast surface display is particularly described herein, as known in the art, phage display, ribosome display, bacterial display or yeast two hybrid systems can also be used in the present invention.

Yeast surface display allows expression of a protein of interest as a fusion protein with the yeast AGA2 agglutinin mating factor on the cell surface. It is an efficient system for directed evolution since a library of protein variants can be readily generated and screened by fluorescence-activated cell sorting (FACS) or magnetic beads (Yeung, Y. A., and Wittrup, K. D. (2002) *Biotechnol Prog* 18, 212-220), and it offers multiple advantages over other display methods such as phage display. Yeast is a eukaryote and so contains protein-processing machinery similar to that of a mammalian cell. Thus, yeasts are more appropriate than prokaryotes to correctly express and display human therapeutic proteins, including MHC molecules. Moreover, the robustness of the yeast surface provides an excellent scaffold for direct biochemical and biophysical characterization of the displayed protein. Yeast surface display coupled with sorting by flow cytometry or magnetic beads has been used to engineer single-chain antibodies, single-chain TCR receptors of increased affinity and stability, stabilized versions of class II I-$A^{g7}$, and more recently, tumor necrosis factor-α (TNF-α) mutants with higher expression levels. The yeast display system is described in U.S. Pat. Nos. 6,423,538 and 6,300,065, for example, which patents are hereby incorporated by reference to the extent not inconsistent herewith.

HLA-DR1

Figure 3:
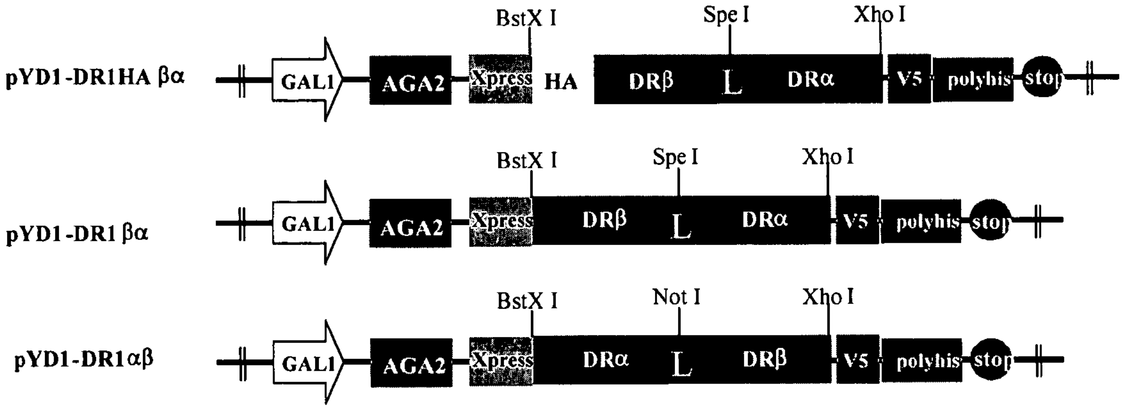
FIG. 3 shows different constructs of single chain HLA-DR1 molecules.

Directed evolution and yeast surface display methods were used to prepare soluble MHC molecules. Human MHC class II molecule HLA-DR1 was used as a model system. HLA-DR1 is associated with rheumatoid arthritis. Constructs of single-chain HLA-DR1 were made with and without a covalently bound high-affinity antigenic peptide containing residue 306-318 ($HA_{306-318}$) of influenza virus hemagglutinin (PKYVKQNTLKILAT, SEQ ID NO:1). For construction of the peptide-free single-chain HLA-DR1 molecule, extracellular domains of DRα and DRβ were amplified from sscDRβHA plasmid (Zhu et al., *Eur. I Immunol.* 27(8):1933-41, 1997) and joined by a linker of 15 amino acids ($G_4SG_3RSG_4S$, SEQ ID NO:45) (scDR1αβ) by splicing overlap extension PCR (SOE-PCR). The α and β domains were amplified from plasmid sscDRβHA with the oligonucleotide pairs α-5BX (5' GTACCAGGATCCAGTG TGGTGGAA GGGGACACCCGACCACG 3', SEQ ID NO:2) / α-3GS (5' GCCAGAGCGGCCGCCACCTG A GCCGCCGCCTCCTAAGTTCTCTGTAGTCTCTGG 3', SEQ ID NO:3), and β-5GS (5' TCAGGTGGCGGCC GCTCTGGCGGAGGTGGATCCGGGGACAC-CCGACCAC 3', SEQ ID NO:4)/β-3XH (5' CCCTCTA-GACT CGAGCTTGCTCTGTGCAGATTCAGAC 3', SEQ ID NO:5), respectively. The primers α-3GS and β-5GS overlap by 20 nucleotides (nt) and were modified to introduce a unique NotI restriction site in the linker sequence that connects the α domain to the β domain. These two PCR products were mixed together and assembled by a primerless PCR, followed by reamplification of the assembled products with the external oligonucleotides α-5BX and β-3XH. The final product was purified, digested with BstXI and XhoI and cloned into the pYD1 vector digested with the same restriction enzymes, giving the plasmid pYD1scαβ (FIG. 3). DNA encoding the single chain βα (scDR1βα) was also obtained from plasmid sscDRβHA by PCR amplification with the oligonucleotides β-5BX (5' GTACCAGGATCCAGTGTGGTGGAAGGGGACACCCGACCA CG 3', SEQ ID NO:6) and α-3XH (5' CCCTCTAGACTCGAGTAAGTTCTCTG TAGTCTCTGG 3', SEQ ID NO:7). The resulting amplification product was cloned into pYD1 via BstXI and XhoI to give pYD1scβα (FIG. 3). The plasmids were sequenced through the entire encoding sequence to verify the absence of undesired mutations introduced by PCR.

Oligonucleotides were synthesized by Integrated DNA Technologies (Coralville, Iowa). Cloned PfuTurbo DNA polymerase and *E. coli* XL1-Blue were purchased from Stratagene (La Jolla, Calif.). Taq DNA polymerase was purchased from Promega (Madison, Wis.). Endonuclease restriction enzymes and DNA ligase were from New England Biolabs (NEB) (Beverly, Mass.). Peptides used in this study were synthesized and purified (>90%) commercially (Jerini AG, Berlin, Germany) and included a peptide containing residues 306-318 of influenza virus hemagglutinin ($HA_{306-318}$) and a HLA-A2-specific Tax-derivative peptide (Tax-8K).

Figure 2A:
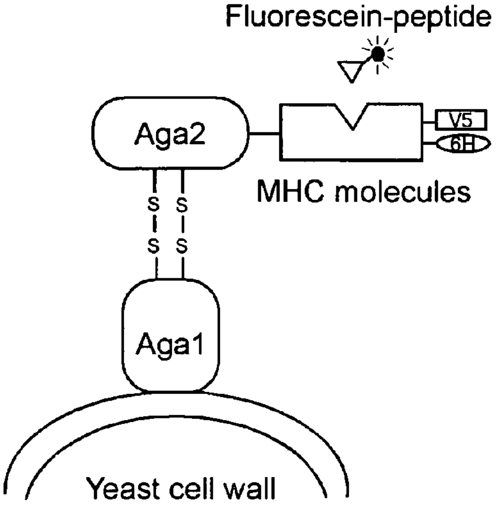
FIG. 2A shows MHC molecules displayed on yeast.

The assembled single-chain HLA-DR1 molecule was cloned into pYD1 vector (Invitrogen) in frame with the C-terminal end of the Aga2 gene. Vector pYD1 uses the α-agglutinin yeast adhesion receptor consisting of two domains, Aga1 and Aga2, to display recombinant proteins on the surface of *S. cerevisiae* based on the fact that Aga1 domain and Aga2-fusion protein can associate to each other by two disulfide bridges within the secretory pathway (FIG. 2A). The yeast surface display system has been successfully used to express single chain antibodies and single chain T-cell receptors (TCRs) and to create variants of these molecules with high affinity using directed evolution. As shown in FIG. 3, genes encoding the single-chain HLA-DR1 molecules HAβα (HA-linker-β-linker-α), βα (β-linker-α) and αβ (α-linker-β) were cloned into yeast surface display vector pYD1 as a fusion to the carboxyl-terminus of Xpress epitope and amino-terminal end of V5 tag. Antibody analysis of Xpress and V5 epitopes by flow cytometry allows the detection of expressed proteins on the cell surface and estimation of their expression levels.

Monoclonal antibodies used in this study were anti-DR L243 (Biodesign International, Saco, Me.), LB3.1 (American Tissue Culture Collection (ATCC), Manassas, Va.), Immuno-357 (Beckman Coulter, Fullerton, Calif.), anti-DR, -DP and -DQ CR3/43 (Biomeda, Foster City, Calif.), anti-Xpress, and anti-V5 (Invitrogen, Carlsbad, Calif.). Biotin-conjugated goat-anti-mouse (GAM) IgG was purchased from Rockland (Gilbertsville, Pa.) and streptavidin-phycoerytrin (SA-PE) conjugate was purchased from PharMingen (San Diego, Calif.). Alkaline phosphatase-conjugated GAM IgG was purchased from Sigma (St. Louis, Mo.). The Zymoprep miniprep kit was obtained from ZymoResearch (Orange, Calif.). The QIAprep spin plasmid mini-prep kits and QIAquick PCR purification kits were purchased from Qiagen (Valencia, Calif.). Unless otherwise indicated, all chemicals were purchased from Sigma (St. Louis, Mo.).

Figure 2B:
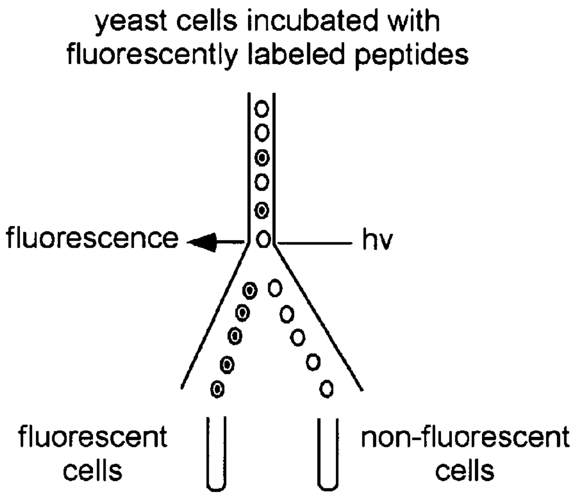
FIG. 2B shows the general FACS sorting method.
Figure 4:
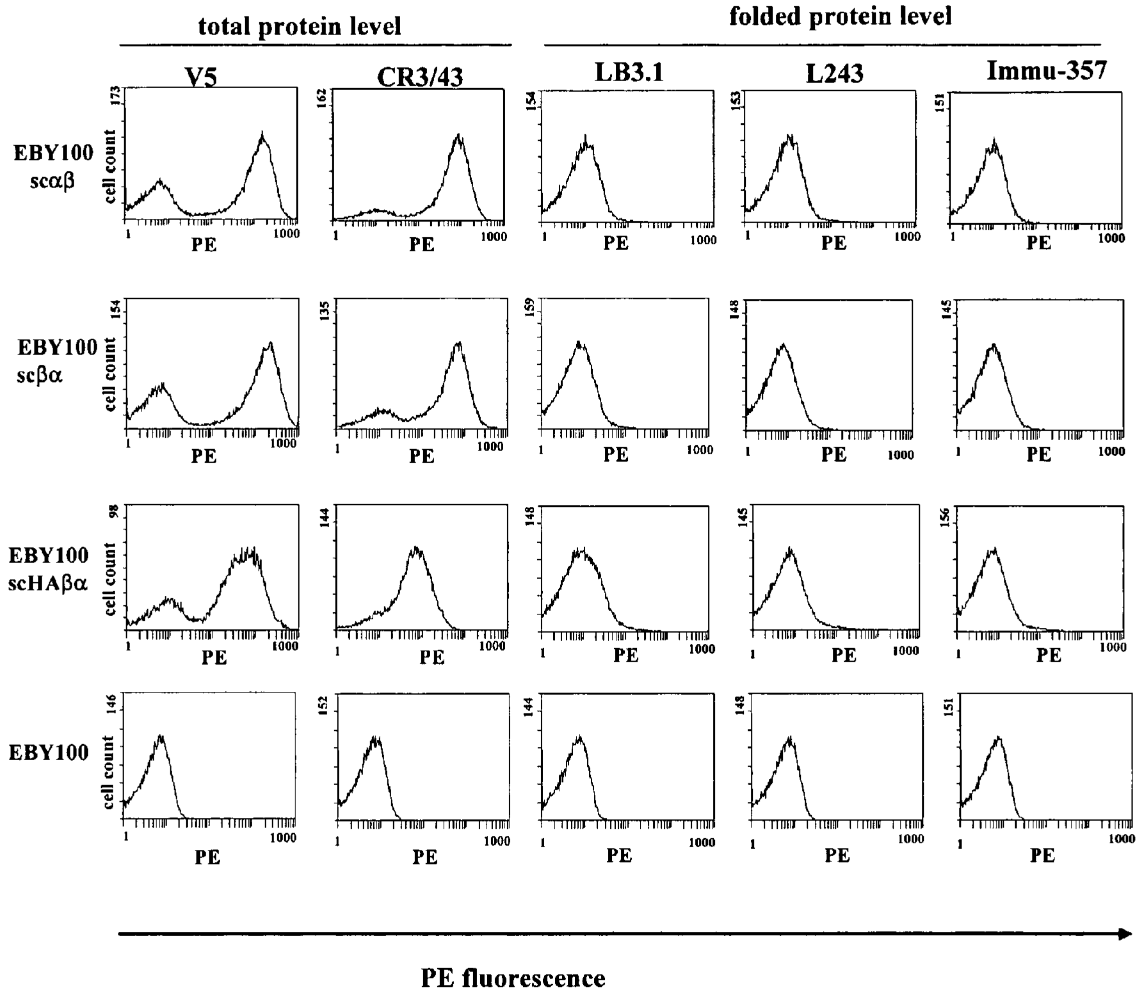
FIG. 4 shows fluorescence of cells displaying the wild-type single-chain HLA-DR1 molecules, αβ, βα and HAβα compared to that of EBY100 control yeast (untransformed).

FIG. 2B shows the general sorting method. FIG. 4 shows fluorescence of cells displaying the wild-type single-chain HLA-DR1 molecules, αβ, βα and HAβα are compared to these of EBY100 control yeast (untransformed). Cells were labeled with V5, CR3/43, LB3.1, L234, Immuno-357 antibodies followed by secondary labeling with biotinylated-goat-anti-mouse Ig antibodies and streptavidin-PE conjugated, then analyzed by flow cytometry. Approximately 75-80% of the population of cells expressed HLA-DR1 on the surface. Histograms of surface expression level, as measured by epitope tag labeling with V5 and CR3/43 antibodies, are shown in the two left columns. Histograms of folded single chain HLA-DR1 as measured by L243, LB3.1 and Immuno-357 antibodies, are shown in the three right columns. Labeled yeast were analyzed on a Coulter Epics XL flow cytometer collecting 30000 cells gated on light scatter (size) to prevent analysis of the clumps. As shown in FIG. 4, all three constructs were capable of expressing soluble single-chain DR1 proteins on the yeast cell surface as indicated by the large cell population with high mean fluorescence intensity stained with anti-V5 antibodies. Similarly, binding of each single-chain DR1 molecule to the DR-specific antibody, CR3/43, which recognizes the denatured β chain of DR molecules, could also be detected by flow cytometry. However, when conformation-sensitive anti-DR antibodies L243, LB3.1 or Immu-357 were used to detect properly folded single chain DR1 molecules, binding of the antibody to the DR1 molecule was barely detected for each of these three DR1 constructs, indicating no or very low level of properly folded DR1 molecules on the yeast cell surface (FIG. 4).

Figure 5:
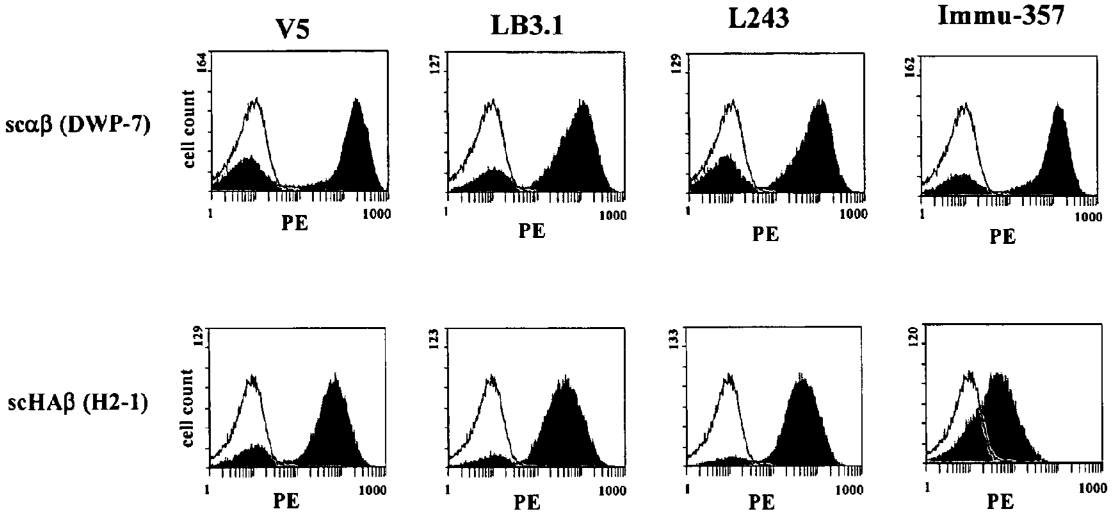
FIG. 5 shows flow cytometric analysis of mutant scHLA-DR1/yeast.

To express properly folded single-chain DR1 molecules and address whether the presence of the peptide and/or chain order within the DR1 molecule could influence the functional soluble expression of this molecule, two mutant libraries, one consisting of single chain DR1 variants in the configuration α-linker-β (lib-αβ) and the other consisting of variants in the configuration HA-linker-β-linker-α (lib-HAβα) were generated by error-prone PCR. Each of these two libraries was sorted through three cycles of FACS with the conformation-sensitive anti-DR antibody L243 followed by biotin-labeled goat-anti-mouse (GAM) IgG and streptavidin-phycoeritrin (SA-PE). In each cycle, yeast cells collected from the previous sort were cultured and protein expression was induced. For the library lib-αβ, protein induction was performed both in the presence or absence of 1 μM of HA peptide into the induction medium. 19 clones isolated from each library were screened for binding to the anti-V5 and anti-DR antibodies L243, LB3.1 and Immu-357. In contrast to wild-type constructs, the mutants showed positive populations with the three conformational antibodies. Representative histograms of one clone of each library are shown in the FIG. 5. FIG. 5 shows flow cytometric analysis of mutant scHLA-DR1/yeast. Yeast displaying mutant αβ DWP-7 (top) or mutant HAβα H2-1 (bottom) was stained with anti-V5 monoclonal antibody, anti-DR LB3.1, L243 and Immu-357 antibodies followed by biotinylated goat-anti-mouse IgG and SA-PE. Unshaded peaks represent cells that were stained only with the secondary labeling reagents. Labeled yeast was analyzed on a Coulter Epics XL flow cytometer collecting 30000 cells gated on light scatter (size) to prevent analysis of the clumps. To ensure the phenotype of the mutant yeast was plasmid-linked, the plasmid was rescued from the respective mutant yeast clone and transformed into fresh EBY100 cells to verify that the selected phenotype was reconstituted. In general, all selected clones showed levels of binding to antibody L234 similar to those obtained with LB3.1 antibody but they differed in the binding to antibody Immu-357. In particular, clones isolated from library lib-HAβα showed reduced binding to this antibody.

Figure 6:
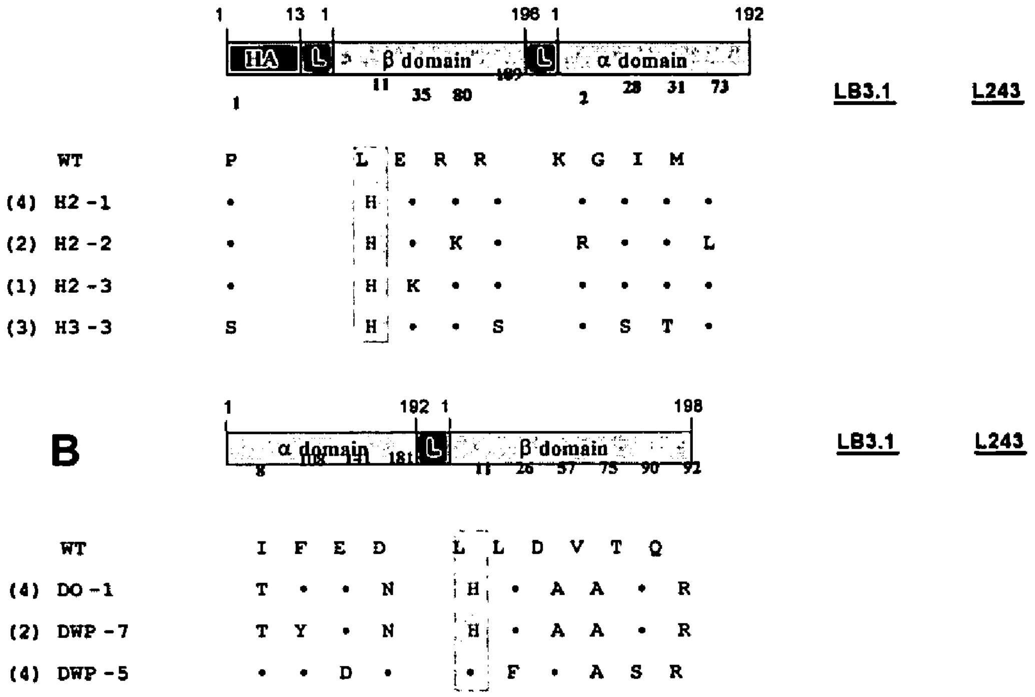
FIG. 6 shows DNA sequence analysis of the selected DR1 mutants from library lib-HAβα (A) and lib-αβ (B). The numbers below the diagrams refer to the amino acid positions in the domains. Dot indicates the residue is the same as wild type DR1. The number in the parenthesis is the number of identical DNA sequences in each group.
Figure 7:
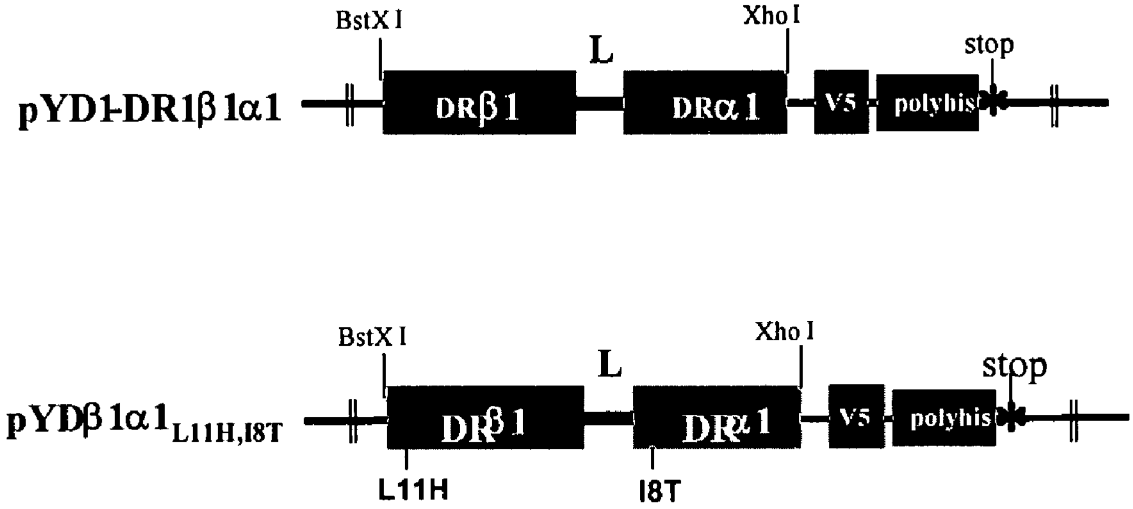
FIG. 7 shows the schematic representation of the two single chain constructs of β1α1 domain of HLA-DR1: wild type β1α1 (top) and double mutant $\beta1\alpha1L_{\beta11H,J\alpha8T}$ (bottom).

To uncover the molecular basis of DR1 expression, the genes encoding those DR1 mutants that exhibited the highest binding to the conformational antibodies LB3.1 and L243 were sequenced (nucleotide and amino acid sequences are shown in Table 1). Deduced amino acid sequences of DR1 mutants selected from library lib-HAβα allowed classification of these mutants in four main groups, represented by H2-1, H2-2, H2-3 and H3-3 in FIG. 6A. Some variants contained several amino acid substitutions but others only presented one amino acid change from the wild type in the β chain, Lβ11H. Interestingly, this single amino acid substitution from the wild type was found in all mutants selected from the library after the third sort. Similarly, DNA sequencing of mutants selected from library lib-αβ allowed to discriminate three different groups of clones, referred as DO-1, DWP-7 and DWP-5 in FIG. 6B, although two of them presented amino acid sequence that only differed in an additional amino acid substitution in the α chain (FIG. 6B). Using site-directed mutagenesis and flow cytometric analysis, three novel single site mutations, Lβ11H, Dβ57A and Lβ26F, in the $\beta_1$ domain, were found to be critical for the proper folding of the single chain DR1 molecules.

β1α1 domains (~180 residues) connected by an amino acid linker were obtained by splicing overlap extension PCR (SOE-PCR). β1 domain was amplified from pYDHA β α with the oligonucleotides β-5BX (5' TACCAGGATCCAGTGTGGTGGAAGGGGACACCC GACCACG 3', SEQ ID NO:6) and β1-3GS (5' CTTCTTTACTAGTACCTCCTGAGCC AACTCGCCGCTGCACTGTG 3', SEQ ID NO:8). α1 domain was amplified from the same vector using the primers α1-5GS (5' GGCTCAGGAGGTACTAGTAAAG 3', SEQ ID NO:9) and α1-3XH (5' CCCTCTAGACTCGAGATTGGTGATCGGAGTATAGTTG 3', SEQ ID NO:10). The primers β1-3GS and α 1-5GS overlap 20 nucleotides with each other and present an unique SpeI restriction site in the linker sequence (GSGGT, SEQ ID NO: 46) that connects the β1 to the α1 domain. These two PCR products were mixed together, primerless assembled and reamplified by PCR with the external oligonucleotides β-5BX and α 1-3XH. The final product was digested with BstXI and XhoI and cloned as a single-chain molecule (β1-linker-α1) into pYD1, in frame with Aga2 and as a fusion to the carboxyl-terminus of Xpress epitope and amino-terminal end of V5 tag (FIG. 7). In order to express folded β1α1 domains on the yeast surface, the mutations Lβ11H and Iα8T previously found in the evolved single-chain αβ molecules were introduced into wild-type pYDβ1α1 to give pYDβ1α$1_{L}\beta_{11H,1^{\alpha}8.T}$ (FIG. 7).

Figure 8:
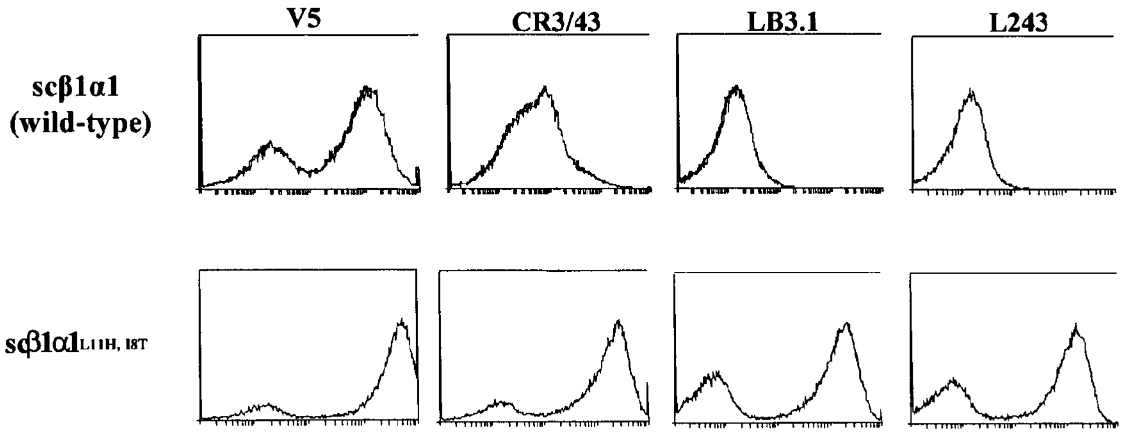
FIG. 8 shows flow cytometric analysis of wild type β1α1 (top) and double mutant $\beta1\alpha1L_{\beta11H,J\alpha8T}$ (bottom).

To make β1α$1_{L}\beta_{11H,1^{\alpha}8T}$, a fragment encoding the β1 domain with the mutations Lβ11H, Qβ92R and the amino terminal end of α1 domain with the mutation Iα8T was obtained by PCR amplification from DWP-7 with the oligonucleotides Xpress5' GGTCGGGATCTGTACGAC GATGACGATAAGGTACCAGGATCCAGTGGGGACACCCGACCACGTTTC 3', SEQ ID NO:11) and β1-3LSpe (5'GATAGAACTCGGCCTGGRTGATCACATGTTCTTCTTTACTA GTACCTCCTGAGCCAACTCGCCGCCGCACTG 3', SEQ ID NO:12). This PCR fragment was inserted into BstXI/SpeI pYDβ1α1 by homologous recombination giving the plasmid pYDβ1α1mut that presents the mutations Lβ11H, Vβ75A, Qβ92R and Iα8T. β1 domain with the only mutation Lβ11H was amplified from the H2-1 mutant with the oligonucleotides Xpress and $\beta_{rev73\text{-}67}$ ((5' GGCCCGCCTCTGCTCCAGGA 3', SEQ ID NO:13) and cloned by yeast homologous recombination into BstXI-treated pYDβ1α1 giving the plasmid pYDβ1α$1_{L\beta11H}$. In one second step, α1 domain with the mutation I8T was amplified from pYDβ1α1 mut with the oligonucleotides $\beta_1$R93 (5' CGGCGAGTTGGCTCAGGAG 3', SEQ ID NO:14) and pYDR3 (5'AGTATGTGTAAAGTTGGTAACG 3', SEQ ID NO:5) and inserted into SpeI/XhoI-treated pDβ1α1H11 by yeast homologous recombination. Yeast clones with plasmid containing the mutations Lβ11H and Iα8T (pYDβ1α$1_{L\beta11H,I\alpha8T}$) were selected by PCR screening with specific primers and DNA sequencing. Sequence of the single-chain β1α1 construct with these two mutations is shown in Table 2). Induction of yeast cells transformed with this plasmid yielding β1α1 domains properly folded, as revealed by their reactivity against conformation-sensitive anti-DR antibodies L243, LB3.1 (FIG. 8). Therefore, the mutations Lβ11H and Iα8T are important for the proper folding of the β1α1 domain.

Figure 10:
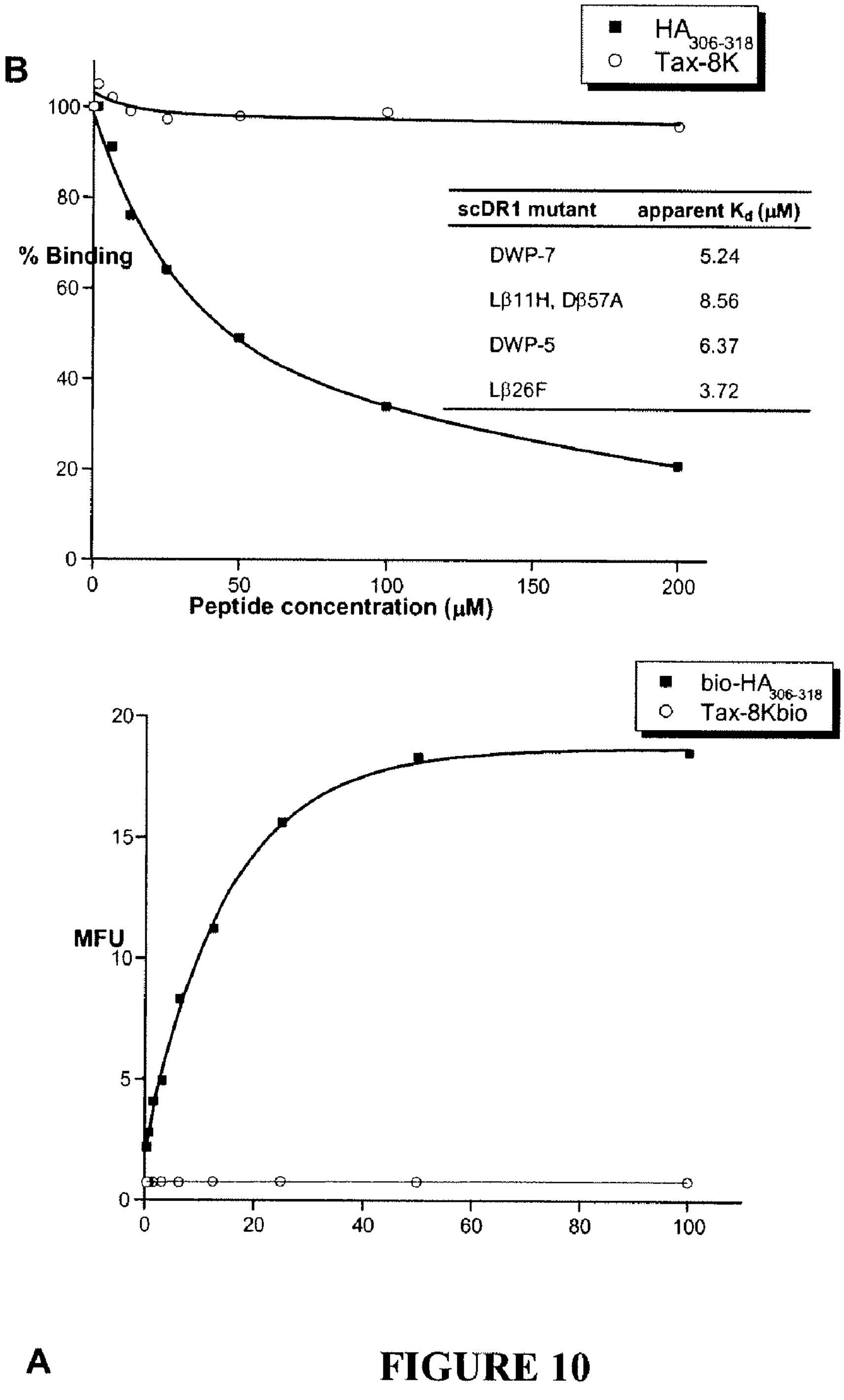
FIG. 10 shows titration curve of the binding to biotinylated $HA_{306-318}$ (DR-specific) and Tax-8Kbio (A2-specific) peptides by mutant DWP-7. A) Direct peptide binding. scDR1αβ-displaying yeast cells were incubated for 20 hours at 37° C. with a series of concentrations of biotinylated DR-specific $HA_{306-318}$ (squares) or A2-specific Tax-8K (circles) peptides. Inset: Apparent association constants of biotinylated $HA_{306-318}$ peptide to yeast-displayed single-chain HLA-DR1 variants. B) Competitive peptide binding. Binding of the biotinylated $HA_{306-318}$ peptide was inhibited by an excess of the unlabeled $HA_{306-318}$ peptide (squares), but not by an A2-specifc Tax-8K peptide (circles). scDR1αβ-displaying yeast cells were incubated for 20 hours at 37° C. with 10 μM of biotinylated peptide at pH 6.5 in the presence of a competitor unlabeled peptide (0-200 μM). DR1-bound biotinylated peptide was quantified by flow cytometry. Specific binding is expressed as the percentage of binding by using the following formula: percentage of binding=[(MFU with competitor-background)/(MFU without competitor-background)]×100%.

The Lβ11H mutation plays an important role in the expression of folded scDR1αβ molecules. Although position 11 in the β chain is polymorphic, His is not found in any of the DR alleles with known sequences. Molecular modeling indicates that the substitution Lβ11H on the first β-sheet strand of the β1 domain approaches the δ(+) amino group of Hβ11 within 5 Å of the ring centroid of Fβ13 where it makes van der Waals contacts with the δ(−) π-electrons of the ring. This amino-aromatic interaction is analogous to the enthalpically favorable interaction between aromatic side chains. In addition, the sulfur atom of Cβ30 is placed at 4 Å from the ring centroid of Hβ11, and may form a strong non-covalent interaction with the π-electron system of the aromatic ring (histidine) of Hβ11. Sulfur-aromatic interactions are weakly polar interactions that are stronger than van der Waal's interactions between nonpolar atoms. These sulfur-aromatic interactions are commonly observed in the hydrophobic core of proteins and may have special significance for stabilizing the folded conformation of proteins. The Dβ57A mutation also promotes the folding of the single-chain DR1αβ molecule since its presence in the single mutant Lβ11H increases the expression level of folded protein by up to 50% (FIG. 10A). Position Dβ57 in DRB alleles, although usually Asp, is polymorphic. Interestingly, the substitution Dβ57A is characteristic of DQ alleles that correlate with insulin-dependent diabetes mellitus (IDDM) susceptibility. Residues Dβ57 in the β1 domain and Rα76 in the α1 domain form a salt-bridge underneath the bound peptide that links the HLA-DR1 β1- and α1-chain helical regions. The substitution of Asp by Ala breaks this salt bridge and therefore could destabilize the structure of HLA-DR1. However, our thermostability data obtained with the mutant scDR1α$\beta_{L\beta11H,D\beta57A}$ (Inset of FIG. 10) do not seem to indicate that the Dβ57A substitution affects the stability of the single-chain DR1 molecules. This observation is in agreement with data previously reported for DQ molecules in which the Dβ57A substitution predominately alters the peptide-binding specificity rather than the overall stability of either empty or peptide-loaded forms of these MHC molecules. Therefore, the contribution of this salt bridge does not seem to be important for protein stability. However, formation of this salt bridge might be a kinetic barrier for the folding of the scDR1αβ molecule, as was proposed for other proteins. Since Aβ57 increases the hydrophobic interaction with Vβ38 and Wβ61 in the β1 chain (FIG. 11D), it is likely that Dβ57A may lower a kinetic barrier in the folding pathway of single-chain DR1 by enhancing the stability of the hydrophobic core of the β1α1 domain. However, we cannot exclude the possibility that these three mutations favor the close packing with some yeast endogenous peptides that in turn help to stabilize a conformation that is critical to subsequent binding of high affinity peptides, such as the $HA_{306\text{-}318}$ peptide. Recently, it has been reported that mutation S11F in the β1 domain of DR3 stabilized the CLIP peptide in the antigen-binding groove.

For biotinylated $HA_{306\text{-}318}$ peptide (bio-$HA_{306\text{-}318}$), the biotin was attached to its N terminus via a linker of two 6-amino-hexanoic acid molecules. For biotinylated Tax peptide, the biotin was attached to the ε-amino group of a lysine residue, substituted at position 8 of the Tax peptide (Tax-8Kbio).

Figure 9:
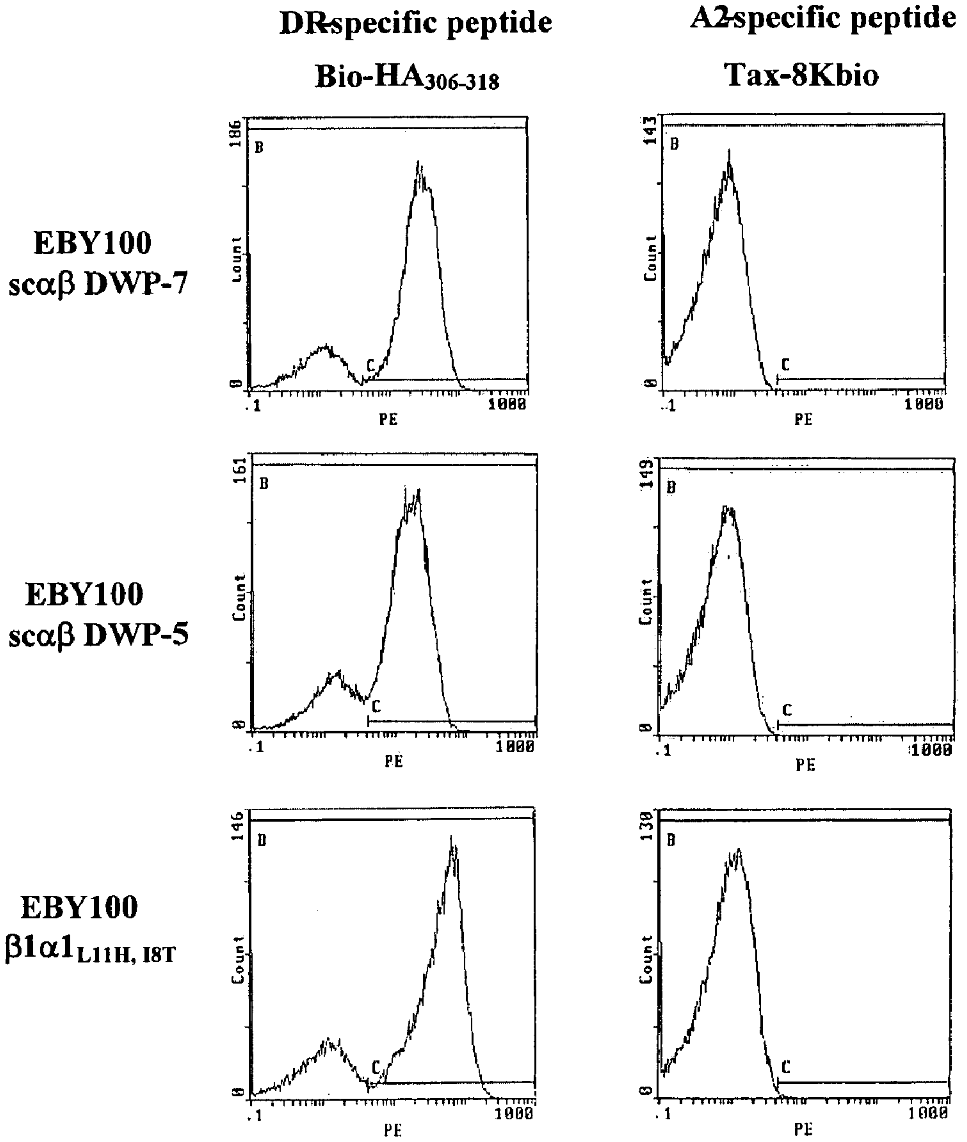
FIG. 9 shows flow cytometric analysis of binding by $HA_{306-318}$ peptide. Binding levels of biotinylated DR-specific $HA_{306-318}$ peptide (left) and A2-specific Tax-8Kbio peptide (right) for the yeast-displaying mutants scαβ DWP-7 (top), DWP-5 (middle) and $\beta1\alpha1\Lambda_{\beta11H,J\alpha8T}$ (bottom) are shown.

To determine whether the different single-chain DR1 mutant proteins were capable of binding peptides, the direct binding of the biotinylated $HA_{306-318}$ peptide to yeast cells displaying mutant single-chain HLA-DR1 molecules was assayed. After incubation of the yeast cells with 25 μM of biotinylated $HA_{306-318}$ peptide for 16 hours at 37° C., a positive population could be observed for the mutants expressing single-chain αβ or β1α1 molecules without a covalently bound peptide (FIG. 9, left panels). This positive population was not observed when the cells were incubated with the same concentration of a biotinylated derivative of the peptide Tax, specific for HLA-A2 molecules (right panels of FIG. 9). Similarly, incubation of yeast cells expressing a class I molecule failed to react with $HA_{306-318}$ peptide (data not shown). In comparison, only a weak binding could be detected for the mutants expressing the heterotrimer of peptide HA, β chain and α chain as a covalently linked single-chain protein.

To estimate the binding constant of the expressed single chain DR1 mutants with the biotinylated $HA_{306-318}$ peptide, and more importantly, to determine the sensitivity of the flow cytometric assay as a high throughput screening method for measuring the affinity and specificity between a specific peptide and the expressed single-chain DR1 mutants, the mean fluorescence units (MFU) of peptide binding of the biotinylated $HA_{306-318}$ peptide to the DR1 mutants DWP-7 and DWP-5 at various peptide concentrations were measured. FIG. 10 shows titration curves of the binding to biotinylated $HA_{306-318}$ (left panel) and Tax8 Kbio (right panel) peptides by mutant DWP-7. The binding of this mutant to different concentrations of biotinylated DR-specific $HA_{306-318}$ peptide is compared to that obtained with a biotinylated derivative of the A2-specific peptide Tax (Tax8 Kbio).

The equilibrium dissociation constant ($K_d$) between the peptide and surface-expressed molecules is estimated from the fluorescence data of flow cytometry using the method described by VanAntwerp et al. with some modifications. Briefly, aliquots of yeast cells displaying HLA-A2 proteins are mixed with fluorescein-labeled peptide antigen ILKECVHGV (SEQ ID NO: 47) at a range of concentrations bracketing the expected $K_d$, and allowed to approach equilibrium at room temperature. Cells are then examined using a flow cytometer. The mean fluorescence intensity of the population of cells is measured. The $K_d$ is calculated by a non-linear least square curve fit of the fluorescence data.

As shown in FIG. 10, the apparent dissociation constant $K_D$ of the biotinylated $HA_{306-318}$ peptide-DWP-7 complex was estimated to be 5 μM. This value is larger than the $K_D$ value determined using soluble wild type HLA-DR1 molecules and non-biotinylated $HA_{306-318}$ peptide (~20 nM). There are several possibilities for this discrepancy. First, the expressed single chain DWP-7 or DWP-5 molecules may bind some weak endogenous peptides, which requires higher concentration of HA peptide for peptide displacement. This possibility is partially supported by the lack of reactivity of DR1 mutants (DWP-7 and DWP-5) with monoclonal antibody KL304 which specifically recognizes empty (peptide-free) HLA-DR molecules. Second, the mutations in the DWP-7 or DWP-5 may affect the peptide binding. Third and most likely, inherent problems of cellular binding assays such as aggregation of cells or other technical difficulties such as limited solubility of peptides may underestimate the real affinities. Nonetheless, the assay is very sensitive since a two-fold difference in peptide concentration between 1 and 10 μM can be discriminated (FIG. 10).

HLA-A2

Figure 11:
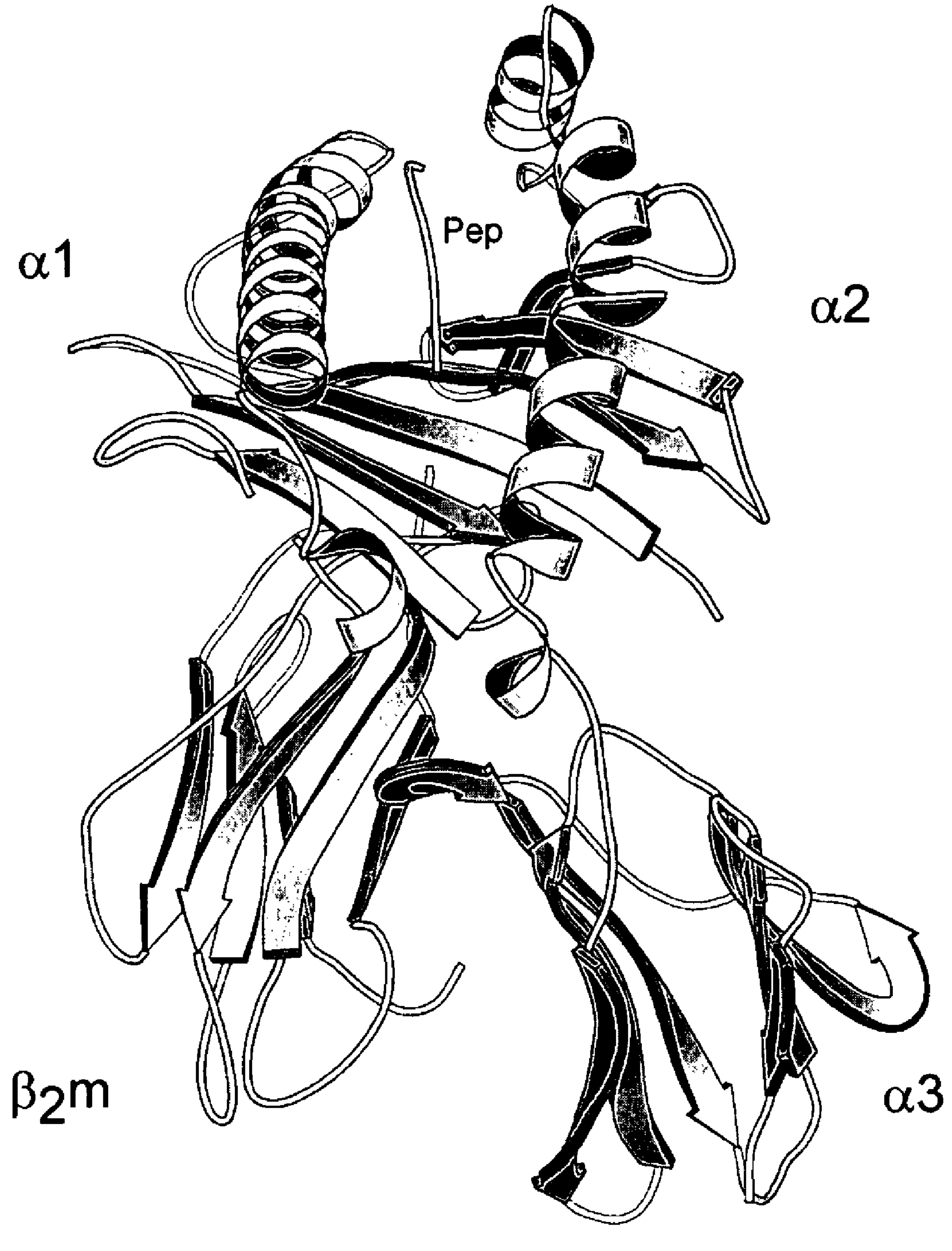
FIG. 11 shows the structure of the class I molecule HLA-A2. The bound peptide is labeled as pep between the α1 and α2 helices.

Human lymphocyte antigen-A2 (HLA-A2) is capable of binding several important viral peptide antigens including influenza A virus matrix M1 residues 58-66, human immunodeficiency virus type 1 (HIV-1) reverse transcriptase residues 309-317, HIV-1 gp120 residues 197-205, human T lymphotrophic virus type 1 (HTLV-1) Tax residues 11-19 and hepatitis B virus nucleocapsid residues 18-27 and presenting them to the T-cells for antigenic recognition. The structure of HLA-A2 is shown in FIG. 11. HLA-A2 including its heavy chain and $\beta_2$m subunit has been expressed in *Escherichia coli* at high levels as inclusion bodies. Thus, to produce functional soluble HLA-A2 molecules, an in vitro refolding process was required. Unfortunately, this refolding process is inefficient and laborious and in addition, such an expression system is not amenable to directed evolution in which screening tens of thousands of variants is required.

Here, two different forms of HLA-A2 molecules (FIG. 12) are expressed: a single chain form of two subunits (scHLA-A2), and a peptide binding scaffold consisting of α1 and α2 domains (pbsHLA-A2) on the yeast surface. These varying forms are designed to find out the minimal structural requirement of HLA-A2 for peptide antigen recognition and T-cell activation as well as the particular construct of HLA-A2 amenable to functional expression.

Expression of HLA-A2 as Wild Type Proteins Using a Yeast Surface Display System

Plasmids p4037 and p714 that contain genes encoding HLA-A2 heavy chain (amino acids 1-271) and $\beta_2$m, respectively, are used as the templates to construct two different forms of HLA-A2 as mentioned above. These two plasmids were obtained from Dr. David N. Garboczi at National Institutes of Health.

Figure 12:
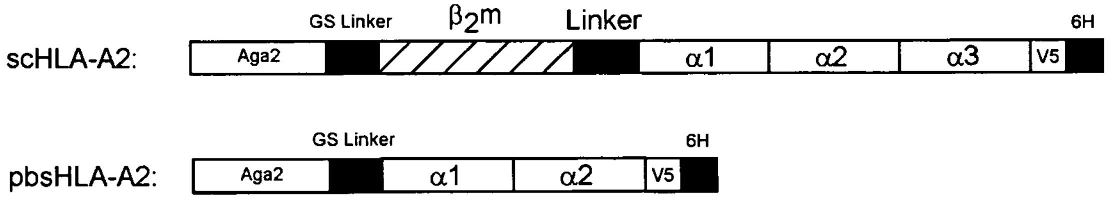
FIG. 12 shows the schematic representation of the two constructs of HLA-A2. scHLA-A2, single chain form of full-length HLA-A2; pbsHLA-A2, the peptide binding scaffold consisting of domains α1 and α2. Both V5 and 6H (polyhistidine) are epitopes for simple detection of displayed proteins. GS linker is the polypeptide $(Gly_4\text{-}Ser)_3$ plus Xpress epitope and some residues in between (Invitrogen catalog).

As shown in FIG. 12, for the single chain full-length form of HLA-A2, scHLA-A2, the two separate subunits are connected through a flexible peptide linker so that the carboxyl-terminus of $\beta_2$m is linked to the amino-terminus of the heavy chain. DNA encoding the extracellular domain of the heavy chain and the $\beta_2$m joined by a linker of 15 amino acids was prepared by splicing overlap extension PCR (SOE-PCR) The DNA encoding the heavy chain subunit is amplified from p4037 with a standard PCR using oligonucleotide primers A1 (5'GGCGGCTCGGG TGGCGGCGGCTCTGGCGGAG-GTGGATCCGGCTCTCACTCCATGAGGTATTTC-3', SEQ ID NO:16), and A2 (5'-ATACCGCTCGAGT TCCCATCTCAGGGTGAGGGG-3', SEQ ID NO:17). The DNA encoding $\beta_2$m is analogously amplified from p714 using primers B1 (5'-GATCGAAGCCAGTGTGGTG-GAAATGATCCAGCGTACTCCAAAG-3', SEQ ID NO:18), and B2 (5' ACCTCCGCCAGAGCCGCCGCCAC-CCGAGCCGCCGCCTCCCATGTCT CGATCCCACT-TAAC 3",SEQ ID NO:19). The assembled fragment was digested with BstXI and XhoI and cloned into vector pYD1 (Invitrogen).

For construction of the second form of HLA-A2 (pbsHLA-A2) (FIG. 12), the DNA encoding the α1 and α2 domains of HLA-A2 is amplified from p4037 with primer A3 (5'GATC-GAAGCCAGTGTGGTGGAAATGGGCTCT-CACTCCATGAGG 3', SEQ ID NO:20) and A4 (5' ATAC-CGCTCGAGCTGCAGCGTCTCCTTCCC3', SEQ ID NO:21). The PCR product is digested with BstXI and XhoI and cloned into pYD1. Sequences are shown in Table 3.

Figure 13:
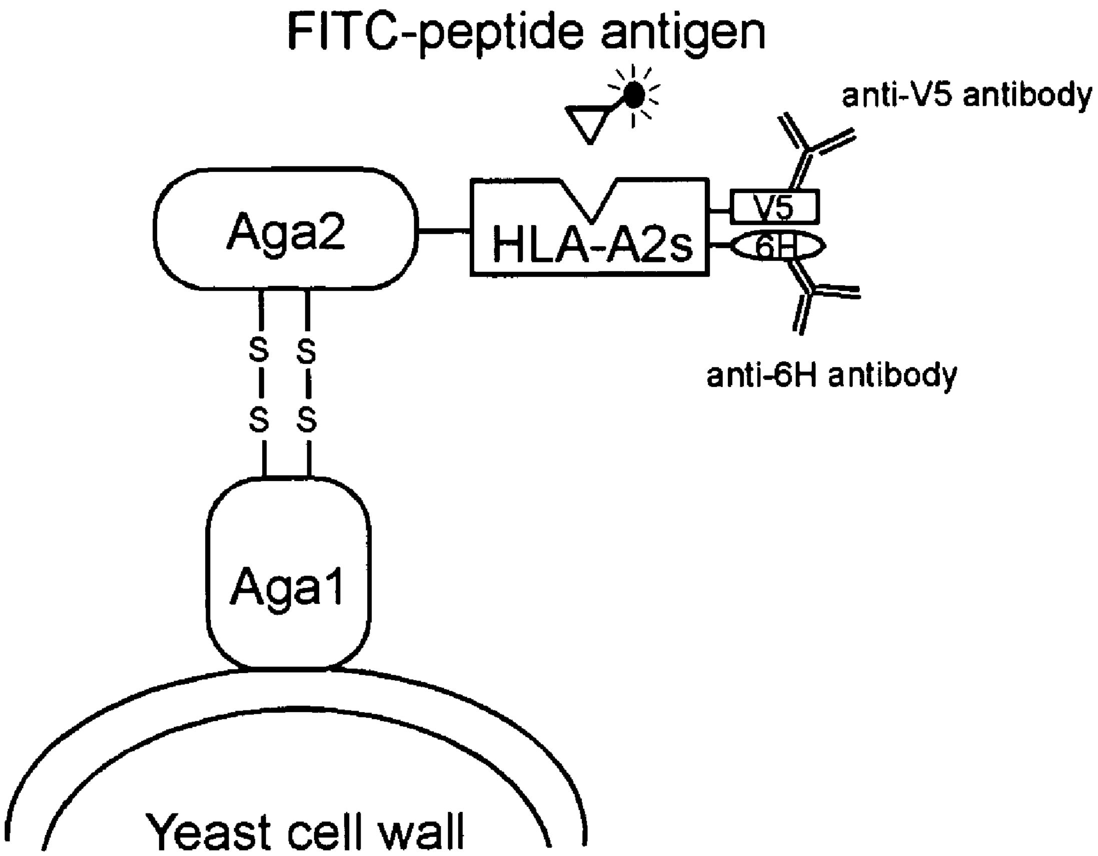
FIG. 13 shows the schematic representation of yeast surface display of various HLA-A2 proteins. The peptide antigen is labeled with a fluorescent dye-FITC.

The yeast display system including vector pYD1 and EBY100 *S. cerevisiae* can be obtained from Invitrogen. pYD1 uses the a-agglutinin yeast adhesion receptor consisting of two domains, Aga1 and Aga2, to display recombinant proteins on the surface of *S. cerevisiae*. Each form of HLA-A2 is cloned into the pYD1 vector in frame with the Aga2 gene. The resulting construct is transformed into the EBY100 *S. cerevisiae* strain. Aga1 and Aga2-fusion protein associate within the secretory pathway and are displayed on the cell surface (FIG. 13). Two epitopes (V5 and 6H) from pYD1 are fused to the C-terminus of the HLA-A2 proteins, allowing the simple detection of the displayed products with anti-V5 antibody or anti-6H antibody.

Figure 14:
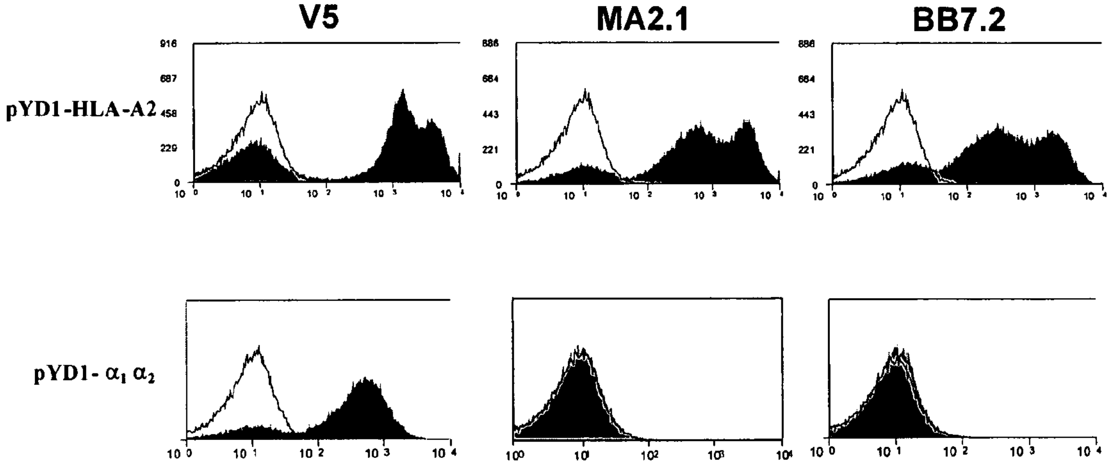
FIG. 14 shows fluorescence of cells displaying wild-type single-chain HLA-A2 and α1α2 molecules.

Antibody analysis of Xpress and V5 epitopes by flow cytometry allows the detection of expressed proteins on the cell surface and estimation of their expression levels. Expression of the Aga2p-HLA-A2 fusion products is induced by the addition of galactose into the growth medium. Surface localization of the fusion products is verified by laser scanning confocal fluorescence microscopy. Both an anti-V5 monoclonal antibody (labeled with a fluorescent dye other than fluorescein, such as phycoerythrin) and a fluorescein-conjugated peptide antigen variant from HIV-1 reverse transcriptase residues 309-317 (the peptide sequence is ILKECVHGV, SEQ ID NO:22) are incubated with the yeast cells. Phycoerythrin is attached to the antibody through an amido ester linkage to the lysine residues while fluorescein maleimide is attached to the peptide through a thio-ether linkage to the cysteine residues. The anti-V5 monoclonal antibody (mAb) specifically binds with the V5-epitope, which indicates the existence of surface-displayed fusion products. The peptide antigen specifically binds with the peptide-binding site of HLA-A2, which indicates the correct folding of the proteins. FIG. 14 shows fluorescence of cells displaying the wild-type single-chain HLA-A2 and $\alpha1\alpha2$ molecules. Cells were labeled with V5, MA2.1, BB7.2 antibodies followed by secondary labeling with biotinylated-goat-anti-mouse Ig antibodies and streptavidin-PE conjugated, then analyzed by flow cytometry. Histograms of surface expression level, as measured by epitope tag labeling with V5 are shown in the left column. Histograms of folded single chain HLA-A2 and $\alpha1\alpha2$ as measured by MA2.1 and BB7.2 antibodies, are shown in the two right columns. As shown in FIG. 14, both constructs were capable of expressing soluble single-chain HLA-A2 on the yeast cell surface as indicated by the mean fluorescence intensity obtained when the induced yeast were stained with anti-V5 antibodies. However, when conformation-sensitive anti-A2 antibodies were used to detect properly folded single chain HLA-A2 molecules, only binding of the antibody to the scHLA-A2 molecule was detected (FIG. 14).

Figure 15:
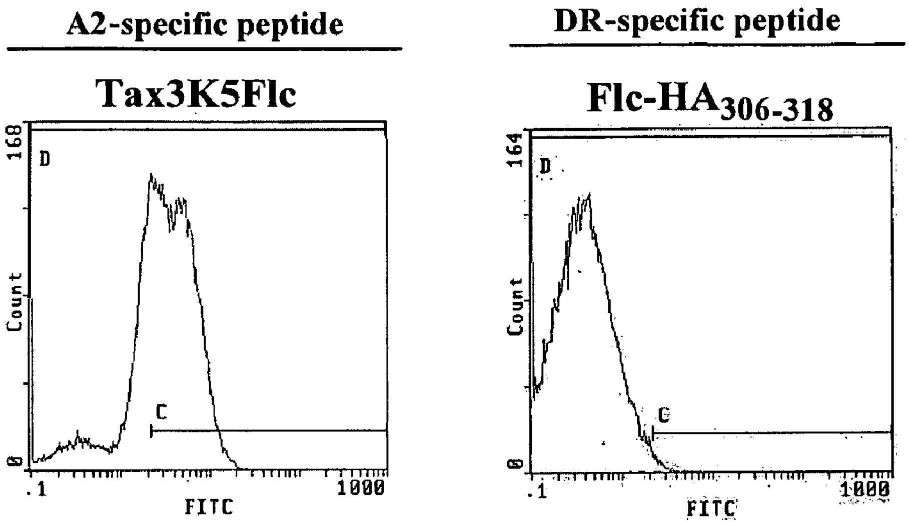
FIG. 15 shows binding of Tax3K5Flc to yeast cells displaying single-chain HLA-A2 molecules.

In addition, to evaluate whether the single-chain HLA-A2 molecules were capable of binding peptides, the direct binding of the fluorescein-conjugated Tax peptide (Tax3K5Flc) to yeast cells displaying the single-chain HLA-A2 molecules was assayed. After incubation of the yeast cells with 25 μM of Tax3K5Flc peptide for 12 hours at room temperature, a positive population could be observed for the yeast displaying single-chain HLA-A2 molecules (FIG. 15). This positive population was not observed when the cells were incubated with the same concentration of the DR-specific $HA_{306-318}$ peptide attached to fluorescein (right panels of FIG. 15). Similarly, incubation of yeast cells expressing the single-chain DR1 molecules described above failed to react with Tax3K5Flc peptide (data not shown).

Protein Chips

The mutant universal peptide-binding scaffolds can be used on a protein chip. In this embodiment, mutants of the universal peptide-binding scaffold are attached to a solid support. The target peptide or peptides are placed in contact with the solid support to allow binding of the target peptide or peptides with the mutants. Binding is determined by means known in the art, such as the use of a fluorescent tag. The mutants that exhibit the desired binding specificity and affinity are isolated. Making protein chips is described in the art, for example, Heng, Z. et al. Global analysis of protein activities using proteome chips. Science 293, 2101-2105 (2001); WO 02/054070; WO01/83827; Mitchell, A perspective on protein microarrays. Nature Biotechnology 20, 225-229 (2002).

The universal peptide binding scaffolds can be used to "read" unique peptide sequences representing the proteins in a given proteome, similar to DNA hybridization in a standard DNA chip. Further, all proteins in a cell population, including membrane proteins can be directly analyzed. Purifying all the proteins is also straightforward, using methods known in the art. Prior to the subject invention, it was difficult to isolate and express folded intact membrane proteins, so no protein capturing agents such as antibodies to recognize membrane proteins had been developed.

Figure 16:
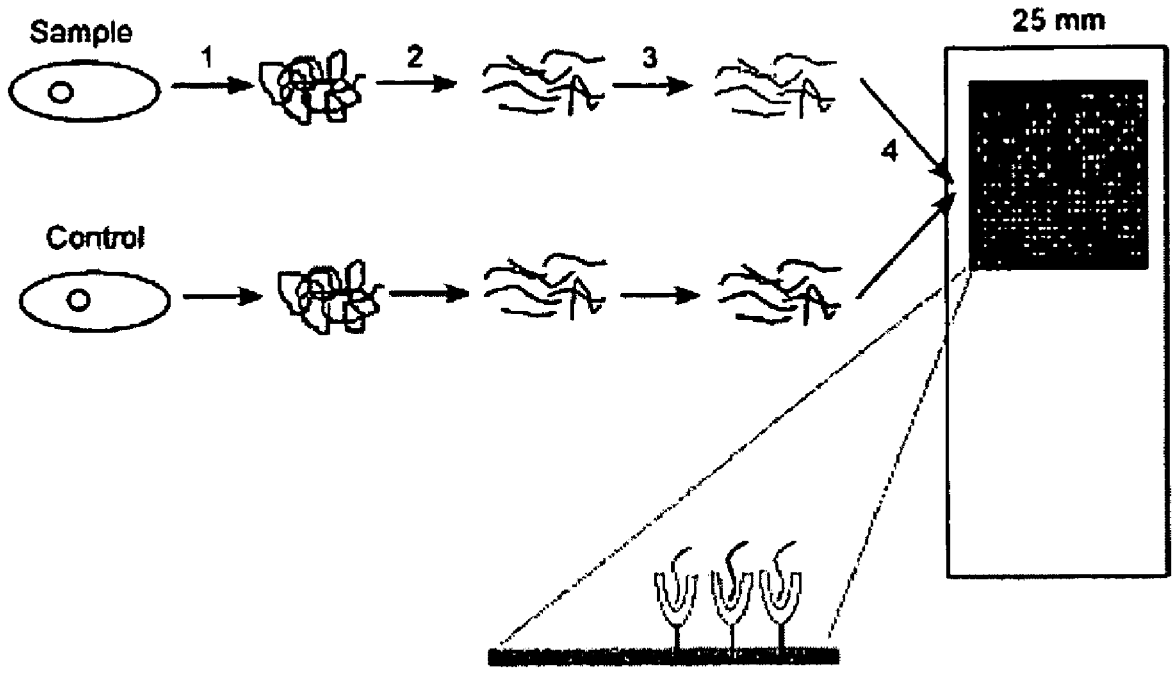
FIG. 16 shows protein expression analysis using a protein chip.

FIG. 16 shows one embodiment of the protein chip. (1) The total pool of proteins from each cell population (control and sample) is extracted. (2) The proteins are denatured and digested into peptides using proteases. (3) The peptides from each sample are labeled with different fluorescent dyes. (4) The two pools of fluorescently labeled peptides are then mixed and hybridized with a protein chip in which the universal peptide-binding scaffolds are arrayed on a glass slide, each of them recognizing a unique peptide sequence representing each protein in a given proteome.

Although the description above contains many specificities, these should not be construed as limiting the scope of the invention but as merely providing illustrations of some of the presently-preferred embodiments of this invention. Specific names of compounds are intended to be exemplary, as it is known that one of ordinary skill in the art can name the same compounds differently. One of ordinary skill in the art will appreciate that methods, device elements, starting materials, synthetic methods, and display methods other than those specifically exemplified can be employed in the practice of the invention without resort to undue experimentation. All art-known functional equivalents, of any such methods, device elements, starting materials, synthetic methods, and display methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. In general the terms and phrases used herein have their art-recognized meaning, which can be found by reference to standard texts, journal references and contexts known to those skilled in the art. All patents and publications mentioned in the specification are indicative of the levels of skill of those skilled in the art to which the invention pertains. One skilled in the art would readily appreciate that the present invention is well adapted to carry out the objects and obtain the ends and advantages mentioned, as well as those inherent therein. The mutants and methods and accessory methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Although the description herein contains many specificities, these should not be construed as limiting the scope of the invention, but as merely providing illustrations of some of the embodiments of the invention. Thus, additional embodiments are within the scope of the invention and within the following claims. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis, additional methods of mutation, additional methods of display and additional uses of the invention.

TABLE 1

DNA and amino acid sequences of the evolved scHLA-DR1 variants.

```
1. Mutant H2-1 (SEQ ID NOs:23 and 24)
            P  K  Y  V  K  Q  N  T  L  K  L  A  T  G  T  G  G  S  L  V
   1 cccaagtatgttaagcaaaacaccctgaagttggcaacaggtaccggtggctcactagtg     60

     P  R  G  S  G  G  G  G  S  G  D  T  R  P  R  F  L  W  Q  H
  61 ccacggggctctggaggaggtgggtccggggacacccgaccacgtttcttgtggcagcat    120

     K  F  E  C  H  F  F  N  G  T  E  R  V  R  L  L  E  R  C  I
 121 aagtttgaatgtcatttcttcaatgggacggagcgggtgcggttgctggaaagatgcatc    180

     Y  N  Q  E  E  S  V  R  F  D  S  D  V  G  E  Y  R  A  V  T
 181 tataaccaagaggagtccgtgcgcttcgacagcgacgtgggggagtaccgggcggtgacg    240

     E  L  G  R  P  D  A  E  Y  W  N  S  Q  K  D  L  L  E  Q  R
 241 gagctggggcggcctgatgccgagtactggaacagccagaaggacctcctggagcagagg    300

     R  A  A  V  D  T  Y  C  R  H  N  Y  G  V  G  E  S  F  T  V
 301 cgggccgcggtggacacctactgcagacacaactacggggttggtgagagcttcacagtg    360

     Q  R  R  V  E  P  K  V  T  V  Y  P  S  K  T  Q  P  L  Q  H
 361 cagcggcgagttgagcctaaggtgactgtgtatccttcaaagacccagcccctgcagcac    420

     H  N  L  L  V  C  S  V  S  G  F  Y  P  G  S  I  E  V  R  W
 421 cacaacctcctggtctgctctgtgagtggtttctatccaggcagcattgaagtcaggtgg    480

     F  R  N  G  Q  E  E  K  A  G  V  V  S  T  G  L  I  Q  N  G
 481 ttccggaacggccaggaagagaaggctggggtggtgtccacaggcctgatccagaatgga    540

     D  W  T  F  Q  T  L  V  M  L  E  T  V  P  R  S  G  E  V  Y
 541 gattggaccttccagaccctggtgatgctggaaacagttcctcggagtggagaggtttac    600

     T  C  Q  V  E  H  P  S  V  T  S  P  L  T  V  E  W  R  A  R
 601 acctgccaagtggagcacccaagtgtgacgagccctctcacagtggaatggagagcacgg    660

     S  E  S  A  Q  R  S  G  G  G  G  S  G  G  T  S  K  E  E  H
 661 tctgaatctgcacagagatctggaggtggaggctcaggaggtactagtaaagaagaacat    720

     V  I  I  Q  A  E  F  Y  L  N  P  D  Q  S  G  E  F  M  F  D
 721 gtgatcatccaggccgagttctatctgaatcctgaccaatcaggcgagtttatgtttgac    780

     F  D  G  D  E  I  F  H  V  D  M  A  K  K  E  T  V  W  R  L
 781 tttgatggtgatgagattttccatgtggatatggcaaagaaggagacggtctggcggctt    840

     E  E  F  G  R  F  A  S  F  E  A  Q  G  A  L  A  N  I  A  V
 841 gaagaatttggacgatttgccagctttgaggctcaaggtgcattggccaacatagctgtg    900

     D  K  A  N  L  E  I  M  T  K  R  S  N  Y  T  P  I  T  N  V
 901 gacaaagccaacctggaaatcatgacaaagcgctccaactatactccgatcaccaatgta    960

     P  P  E  V  T  V  L  T  N  S  P  V  E  L  R  E  P  N  V  L
 961 cctccagaggtaactgtgctcacgaacagccctgtggaactgagagagcccaacgtcctc   1020
```

TABLE 1-continued

DNA and amino acid sequences of the evolved scHLA-DR1 variants.

```
     I  C  F  I  D  K  F  T  P  P  V  V  N  V  T  W  L  R  N  G
1021 atctgtttcatcgacaagttcaccccaccagtggtcaatgtcacgtggcttcgaaatgga    1080

     K  P  V  T  T  G  V  S  E  T  V  F  L  P  R  E  D  H  L  F
1081 aaacctgtcaccacaggagtgtcagagacagtcttcctgcccagggaagaccaccttttc    1140

     R  K  F  H  Y  L  P  F  L  P  S  T  E  D  V  Y  D  C  R  V
1141 cgcaagttccactatctccccttcctgccctcaactgaggacgtttacgactgcagggtg    1200

     E  H  W  G  L  D  E  P  L  L  K  H  W  E  F  D  A  P  S  P
1201 gagcactggggcttggatgagcctcttctcaagcactgggagtttgatgcaccaagccct    1260

     L  P  E  T  T  E  N  L  L  E  S  R  G  P  F  E  G  K  P  I
1261 ctcccagagactacagagaacttactcgagtctagagggcccttcgaaggtaagcctatc    1320

     P  N  P  L  L  G  L  D  S  T  R  T  G  H  H  H  H  H  H  *
1321 cctaaccctctcctcggtctcgattctacgcgtaccggtcatcatcaccatcaccattga    1380
```

2. Mutant H2-2 (SEQ ID NOs:25 and 26)

```
             P  K  Y  V  K  Q  N  T  L  K  L  A  T  G  T  G  G  S  L  V
   1 cccaagtatgttaagcaaaacaccctgaagttggcaacaggtaccggtggctcactagtg      60

     P  R  G  S  G  G  G  G  S  G  D  T  R  P  R  F  L  W  Q  H
  61 ccacggggctctggaggaggtgggtccggggacacccgaccacgtttcttgtggcagcat     120

     K  F  E  C  H  F  F  N  G  T  E  R  V  R  L  L  E  R  C  I
 121 aagtttgaatgtcatttcttcaatgggacggagcgggtgcggttgctggaaagatgcatc     180

     Y  N  Q  E  E  S  V  R  F  D  S  D  V  G  E  Y  R  A  V  T
 181 tataaccaagaggagtccgtgcgcttcgacagcgacgtgggggagtaccgggcggtgacg     240

     E  L  G  R  P  D  A  E  Y  W  N  S  Q  K  D  L  L  E  Q  R
 241 gagctggggcggcctgatgccgagtactggaacagccagaaggacctcctggagcagagg     300

     R  A  A  V  D  T  Y  C  K  H  N  Y  G  V  G  E  S  F  T  V
 301 cgggccgcggtggacacctactgcaaacacaactacggggttggtgagagcttcacagtg     360

     Q  R  R  V  E  P  K  V  T  V  Y  P  S  K  T  Q  P  L  Q  H
 361 cagcggcgagttgagcctaaggtgactgtgtatccttcaaagacccagcccctgcagcac     420

     H  N  L  L  V  C  S  V  S  G  F  Y  P  G  S  I  E  V  R  W
 421 cacaacctcctggtctgctctgtgagtggtttctatccaggcagcattgaagtcaggtgg     480

     F  R  N  G  Q  E  E  K  A  G  V  V  S  T  G  L  I  Q  N  G
 481 ttccggaacggccaggaagagaaggctggggtggtgtccacaggcctgatccagaatgga     540

     D  W  T  F  Q  T  L  V  M  L  E  T  V  P  R  S  G  E  V  Y
 541 gattggaccttccagaccctggtgatgctggaaacagttcctcggagtggagaggtttac     600

     T  C  Q  V  E  H  P  S  V  T  S  P  L  T  V  E  W  R  A  R
 601 acctgccaagtggagcacccaagtgtgacgagccctctcacagtggaatggagagcacgg     660

     S  E  S  A  Q  R  S  G  G  G  G  S  G  G  T  S  R  E  E  H
 661 tctgaatctgcacagagatctggaggtggaggctcaggaggtactagtagagaagaacat     720

     V  I  I  Q  A  E  F  Y  L  N  P  D  Q  S  G  E  F  M  F  D
 721 gtgatcatccaggccgagttctatctgaatcctgaccaatcaggcgagtttatgtttgac     780

     F  D  G  D  E  I  F  H  V  D  M  A  K  K  E  T  V  W  R  L
 781 tttgatggtgatgagattttccatgtggatatggcaaagaaggagacggtctggcggctt     840

     E  E  F  G  R  F  A  S  F  E  A  Q  G  A  L  A  N  I  A  V
 841 gaagaatttggacgatttgccagctttgaggctcaaggtgcattggccaacatagctgtg     900

     D  K  A  N  L  E  I  L  T  K  R  S  N  Y  T  P  I  T  N  V
 901 gacaaagccaacctggaaatcttgacaaagcgctccaactatactccgatcaccaatgta     960

     P  P  E  V  T  V  L  T  N  S  P  V  E  L  R  E  P  N  V  L
 961 cctccagaggtaactgtgctcacgaacagccctgtggaactgagagagcccaacgtcctc    1020

     I  C  F  I  D  K  F  T  P  P  V  V  N  V  T  W  L  R  N  G
1021 atctgtttcatcgacaagttcaccccaccagtggtcaatgtcacgtggcttcgaaatgga    1080

     K  P  V  T  T  G  V  S  E  T  V  F  L  P  R  E  D  H  L  F
1081 aaacctgtcaccacaggagtgtcagagacagtcttcctgcccagggaagaccaccttttc    1140
```

TABLE 1-continued

DNA and amino acid sequences of the evolved scHLA-DR1 variants.

R K F H Y L P F L P S T E D V Y D C R V
1141 cgcaagttccactatctccccttcctgccctcaactgaggacgtttacgactgcagggtg 1200

E H W G L D E P L L K H W E F D A P S P
1201 gagcactggggcttggatgagcctcttctcaagcactgggagtttgatgcaccaagccct 1260

L P E T T E N L L E S R G P F E G K P I
1261 ctcccagagactacagagaacttactcgagtctagagggcccttcgaaggtaagcctatc 1320

P N P L L G L D S T R T G H H H H H H *
1321 cctaaccctctcctcggtctcgattctacgcgtaccggtcatcatcaccatcaccattga 1380

3. Mutant H2-3 (SEQ ID NOs:27 and 28)

P K Y V K Q N T L K L A T G T G G S L V
1 cccaagtatgttaagcaaaacaccctgaagttggcaacaggtaccggtggctcactagtg 60

P R G S G G G G S G D T R P R F L W Q H
61 ccacggggctctggaggaggtgggtccggggacacccgaccacgtttcttgtggcagcat 120

K F E C H F F N G T E R V R L L E R C I
121 aagtttgaatgtcatttcttcaatgggacggagcgggtgcggttgctggaaagatgcatc 180

Y N Q K E S V R F D S D V G E Y R A V T
181 tataaccaaaaggagtccgtgcgcttcgacagcgacgtgggggagtaccgggcggtgacn 240

E L G R P D A E Y W N S Q K D L L E Q R
241 gagctggggcggcctgatgccgagtactggaacagccagaaggacctcctggagcaaagg 300

R A A V D T Y C R H N Y G V G E S F T V
301 cgggccgccgtggacacctactgcagacacaactacggggttggtgagagcttcacagtg 360

Q R R V E P K V T V Y P S K T Q P L Q H
361 cagcggcgagttgagcctaaggtgactgtgtatccttcaaagacccagcccctgcagcac 420

H N L L V C S V S G F Y P G S I E V R W
421 cacaacctcctggtctgctctgtgagtggtttctatccaggcagcattgaagtcaggtgg 480

F R N G Q E E K A G V V S T G L I Q N G
481 ttccggaacggccaggaagagaaggctggggtggtgtccacaggcctgatccagaatgga 540

D W T F Q T L V M L E T V P R S G E V Y
541 gattggaccttccagaccctggtgatgctggaaacagttcctcggagtggagaggtttac 600

T C Q V E H P S V T S P L T V E W R A R
601 acctgccaagtggagcacccaagtgtgacgagccctctcacagtggaatggagagcacgg 660

S E S A Q R S G G G G S G G T S K E E H
661 tctgaatctgcacagagatctggaggtggaggctcaggaggtactagtaaagaagaacat 720

V I I Q A E F Y L N P D Q S G E F M F D
721 gtgatcatccaggccgagttctatctgaatcctgaccaatcaggcgagtttatgtttgac 780

F D G D E I F H V D M A K K S T V W R L
781 tttgatggtgatgagattttccatgtggatatggcaaagaaggagacggtctggcggctt 840

E E F G R F A S F E A Q G A L A N I A V
841 gaagaatttggacgatttgccagctttgaggctcaaggtgcattggccaacatagctgtg 900

D K A N L E I M T K R S N Y T P I T N V
901 gacaaagccaacctggaaatcatgacaaagcgctccaactatactccgatcaccaatgta 960

P P E V T V L T N S P V E L R E P N V L
961 cctccagaggtaactgtgctcacgaacagccctgtggaactgagagagcccaacgtcctc 1020

I C F I D K F T P P V V N V T W L R N G
1021 atctgtttcatcgacaagttcaccccaccagtggtcaatgtcacgtggcttcgaaatgga 1080

K P V T T G V S E T V F L P R E D H L F
1081 aaacctgtcaccacaggagtgtcagagacagtcttcctgcccagggaagaccaccttttc 1140

R K F H Y L P F L P S T E D V Y D C R V
1141 cgcaagttccactatctccccttcctgccctcaactgaggacgtttacgactgcagggtg 1200

E H W G L D S P L L K H W E F D A P S P
1201 gagcactggggcttggatgagcctcttctcaagcactgggagtttgatgcaccaagccct 1260

TABLE 1-continued

DNA and amino acid sequences of the evolved scHLA-DR1 variants.

L P E T T E N * L E S R G P F E G K P I
1261 ctcccagagactacagagaactgactcgagtctagagggcccttcgaaggtaagcctatc 1320

R S P L L G L D S T R T G H H H H H H *
1321 cgtagccctctcctcggtctcgattctacgcgtaccggtcatcatcaccatcaccattga 1380

4. Mutant H3-3 (SEQ ID NOs:29 and 30)

S K Y V K Q N T L K L A T G T G G S L V
1 tccaagtatgttaagcaaaacaccctgaagttggcaacaggtaccggtggctctctagtg 60

P R G S G G G G S G D T R P R F L W Q H
61 ccacggggctctggaggaggtgggtccggggacacccgaccacgtttcttgtggcagcat 120

K F E C H F F N G T E R V R L L E R C I
121 aagtttgaatgtcatttcttcaatgggacggagcgggtgcggttgctggaaagatgcatc 180

Y N Q E E S V R F D S D V G E Y R A V T
181 tataaccaagaggagtccgtgcgcttcgacagcgacgtgggggagtaccgggcggtgacg 240

E L G R P D A E Y W N S Q K D L L E Q R
241 gagctggggcggcctgatgccgagtactggaacagccagaaggacctcctggagcagagg 300

R A A V D T Y C R H N Y G V G E S F T V
301 cgggccgcggtggacacctactgcagacacaactacggggttggtgagagcttcacagtg 360

Q R R V E P K V T V Y P S K T Q P L Q H
361 cagcggcgagttgagcctaaggtgactgtgtatccttcaaagacccagcccctgcagcac 420

H N L L V C S V S G F Y P G S T E V R W
421 cacaacctcctggtctgctctgtgagtggtttctatccaggcagcattgaagtcaggtgg 480

F R N G Q E E K A G V V S T G L I Q N G
481 ttccggaacggccaggaagagaaggctggggtggtgtccacaggcctgatccagaatgga 540

D W T F Q T L V M L E T V F R S G E V Y
541 gattggaccttccagaccctggtgatgctggaaacagttcctcggagtggagaggtttac 600

T C Q V E H P S V T S F L T V E W S A R
601 acctgccaagtggagcacccaagtgtgacgagccctctcacagtggaatggagtgcacgg 660

S E S A Q R S G G G G S G G T S K E E H
661 tctgaatctgcacagagatctggaggtggaggctcaggaggtactagtaaagaagaacat 720

V I I Q A E F Y L N P D Q S G E F M F D
721 gtgatcatccaggccgagttctatctgaatcctgaccaatcaggcgagtttatgtttgac 780

F D S D E T F H V D M A K K E T V W R L
781 tttgatagtgatgagactttccatgtggatatggcaaagaaggagacggtctggcggctt 840

E E F G R F A S F E A Q G A L A N I A V
841 gaagaatttggacgatttgccagctttgaggctcaaggtgcattggccaacatagctgtg 900

D K A N L H I M T K R S N Y T P I T N V
901 gacaaagccaacctggaaatcatgacaaagcgctccaactatactccgatcaccaatgta 960

P P E V T V L T N S F V E L R E F N V L
961 cctccagaggtaactgtgctcacgaacagccctgtggaactgagagagcccaacgtcctc 1020

I C F I D K F T P P V V N V T W L R N G
1021 atctgtttcatcgacaagttcaccccaccagtggtcaatgtcacgtggcttcgaaatgga 1080

K F V T T G V S E T V F L P R E D H L F
1081 aaacctgtcaccacaggagtgtcagagacagtcttcctgcccagggaagaccaccttttc 1140

R K F H Y L P F L P S T E D V Y D C R V
1141 cgcaagttccactatctccccttcctgccctcaactgaggacgtttacgactgcagggtg 1200

E H W G L D E P L L K H W E F D A P S F
1201 gagcactggggcttggatgagcctcttctcaagcactgggagtttgatgcaccaagccct 1260

L P E T T E N L L E S R G P F E G K P I
1261 ctcccagagactacagagaacttactcgagtctagagggcccttcgaaggtaagcctatc 1320

P N F L L G L D S T R T G H H H H H H *
1321 cctaaccctctcctcggtctcgattctacgcgtaccggtcatcatcaccatcaccattga 1380P For mutants H2-1, H2-2, H2-3 and H3-3, aa1 of α chain is Ser instead Ile and aa 193 (last amino acid of α chain) is Leu instead Val.

TABLE 1-continued

DNA and amino acid sequences of the evolved scHLA-DR1 variants.

```
5. Mutant DO-1 (SEQ ID NOs:31 and 32)
     R  K  E  E  H  V  I  T  Q  A  E  F  Y  L  N  P  D  Q  S  G
   1 aggaaagaagaacatgtgatcacccaggccgagttctatctgaatcctgaccaatcaggc      60

     E  F  M  F  D  F  D  G  D  E  I  F  H  V  D  M  A  K  K  E
  61 gagtttatgtttgactttgatggtgatgagattttccatgtggatatggcaaagaaggag     120

     T  V  W  R  L  E  E  F  G  R  F  A  S  F  E  A  Q  G  A  L
 121 acggtctggcggcttgaagaatttggacgatttgccagctttgaggctcaaggtgcattg     180

     A  N  I  A  V  D  K  A  N  L  E  I  M  T  K  R  S  N  Y  T
 181 gccaacatagctgtggacaaagccaacctggaaatcatgacaaagcgctccaactatact     240

     P  I  T  N  V  P  P  E  V  T  V  L  T  N  S  P  V  E  L  R
 241 ccgatcaccaatgtacctccagaggtaactgtgctcacgaacagccctgtggaactgaga     300

     E  P  N  V  L  I  C  Y  I  D  K  F  T  P  P  V  V  N  V  T
 301 gagcccaacgtcctcatctgttacatcgacaagttcaccccaccagtggtcaatgtcacg     360

     W  L  R  N  G  K  P  V  T  T  G  V  S  E  T  V  F  L  P  R
 361 tggcttcgaaatggaaaacctgtcaccacaggagtgtcagagacagtcttcctgcccagg     420

     E  D  H  L  F  R  K  F  H  Y  L  P  F  L  P  S  T  E  D  V
 421 gaagaccaccttttccgcaagttccactatctccccttcctgccctcaactgaggacgtt     480

     Y  D  C  R  V  E  H  W  G  L  D  E  P  L  L  K  H  W  E  F
 481 tacgactgcagggtggagcactggggcttggatgagcctcttctcaagcactgggagttt     540

     N  A  P  S  P  L  P  E  T  T  E  N  L  G  G  G  G  S  G  G
 541 aatgcaccaagccctctcccagagactacagagaacttaggaggcggcggctcaggtggc     600

     G  R  S  G  G  G  G  S  G  D  T  R  P  R  F  L  W  Q  H  K
 601 ggccgctctggcggaggtggatccggggacacccgaccacgtttcttgtggcagcataag     660

     F  E  C  H  F  F  N  G  T  E  R  V  R  L  L  E  R  C  I  Y
 661 tttgaatgtcatttcttcaatgggacggagcgggtgcggttgctggaaagatgcatctat     720

     N  Q  E  E  S  V  R  F  D  S  D  V  G  E  Y  R  A  V  T  E
 721 aaccaagaggagtccgtgcgcttcgacagcgacgtgggggagtaccgggcggtgacggag     780

     L  G  R  P  A  A  E  Y  W  N  S  Q  K  D  L  L  E  Q  R  R
 781 ctggggcggcctgctgccgagtactggaacagccagaaggacctcctggagcagaggcgg     840

     A  A  A  D  T  Y  C  R  H  N  Y  G  V  G  E  S  F  T  V  R
 841 gccgcggcggacacctactgcagacacaactacggggttggtgagagcttcacagtgcgg     900

     R  R  V  E  P  K  V  T  V  Y  P  S  K  T  Q  P  L  Q  H  H
 901 cggcgagttgagcctaaggtgactgtgtatccttcaaagacccagcccctgcagcaccac     960

     N  L  L  V  C  S  V  S  G  F  Y  P  G  S  I  E  V  R  W  F
 961 aacctcctggtctgctctgtgagtggtttctatccaggcagcattgaagtcaggtggttc    1020

     R  N  G  Q  E  E  K  A  G  V  V  S  T  G  L  I  Q  N  G  D
1021 cggaacggccaggaagagaaggctggggtggtgtccacaggcctgatccagaatggagat    1080

     W  T  F  Q  T  L  V  M  L  E  T  V  P  R  S  G  E  V  Y  T
1081 tggaccttccagaccctggtgatgctggaaacagttcctcggagtggagaggtttacacc    1140

     C  Q  V  E  H  P  S  V  T  S  P  L  T  V  E  W  R  A  R  S
1141 tgccaagtggagcacccaagtgtgacgagccctctcacagtggaatggagagcacggtct    1200

     E  S  A  Q  S  K  L  E  S  R  G  P  F  E  G  K  P  I  P  N
1201 gaatctgcacagagcaagctcgagtctagagggcccttcgaaggtaagcctatccctaac    1260

     P  L  L  G  L  D  S  T  R  T  G  H  H  H  H  H  H  *
1261 cctctcctcggtctcgattctacgcgtaccggtcatcatcaccatcaccattga          1314

6. Mutant DWP-5 (SEQ ID NOs:33 and 34)
     R  K  E  E  H  V  I  I  Q  A  E  F  Y  L  N  P  D  Q  S  G
   1 aggaaagaagaacatgtgatcatccaggccgagttctatctgaatcctgaccaatcaggc      60

     E  F  M  F  D  F  D  G  D  E  I  F  H  V  D  M  A  K  K  E
  61 gagtttatgtttgactttgatggtgatgagattttccatgtggatatggcaaagaaggag     120

     T  V  W  R  L  E  E  F  G  R  F  A  S  F  E  A  Q  G  A  L
 121 acggtctggcggcttgaagaatttggacgatttgccagctttgaggctcaaggtgcattg     180
```

TABLE 1-continued

DNA and amino acid sequences of the evolved scHLA-DR1 variants.

```
     A  N  I  A  V  D  K  A  N  L  E  I  M  T  K  R  S  N  Y  T
 181 gccaacatagctgtggacaaagccaacctggaaatcatgacaaagcgctccaactatact    240

     P  I  T  N  V  P  P  E  V  T  V  L  T  N  S  P  V  E  L  R
 241 ccgatcaccaatgtacctccagaggtaactgtgctcacgaacagccctgtggaactgaga    300

     E  P  N  V  L  I  C  F  I  D  K  F  T  P  P  V  V  N  V  T
 301 gagcccaacgtcctcatctgtttcatcgacaagttcaccccaccagtggtcaatgtcacg    360

     W  L  R  N  G  K  P  V  T  T  G  V  S  E  T  V  F  L  P  R
 361 tggcttcgaaatggaaaacctgtcaccacaggagtgtcagagacagtcttcctgcccagg    420

     D  D  H  L  F  R  K  F  H  Y  L  P  F  L  P  S  T  E  D  V
 421 gatgaccaccttttccgcaagttccactatctccccttcctgccctcaactgaggacgtt    480

     Y  D  C  R  V  E  H  W  G  L  D  E  P  L  L  K  H  W  E  F
 481 tacgactgcagggtggagcactggggcttggatgagcctcttctcaagcactgggagttt    540

     D  A  P  S  P  L  P  E  T  T  E  N  L  G  G  G  G  S  G  G
 541 gatgcaccaagccctctcccagagactacagagaacttaggaggcggcggctcaggtggc    600

     G  R  S  G  G  G  G  S  G  D  T  R  P  R  F  L  W  Q  L  K
 601 ggccgctctggcggaggtggatccggggacacccgaccacgtttcttgtggcagcttaag    660

     F  E  C  H  F  F  N  G  T  E  R  V  R  F  L  E  R  C  I  Y
 661 tttgaatgtcatttcttcaatgggacggagcgggtgcggtttctggaaagatgcatctat    720

     N  Q  E  E  S  V  R  F  D  S  D  V  G  E  Y  R  A  V  T  E
 721 aaccaagaggagtccgtgcgcttcgacagcgacgtgggggagtaccgggcggtgacggag    780

     L  G  R  P  D  A  E  Y  W  N  S  Q  K  D  L  L  E  Q  R  R
 781 ctggggcggcctgatgccgagtactggaacagccagaaggacctcctggagcagaggcgg    840

     A  A  A  D  T  Y  C  R  H  N  Y  G  V  G  E  S  F  S  V  R
 841 gccgcggcggacacctactgcagacacaactacggggttggtgagagcttctcagtgcgg    900

     R  R  V  E  P  K  V  T  V  Y  P  S  K  T  Q  P  L  Q  H  H
 901 cggcgagttgagcctaaggtgactgtgtatccttcaaagacccagcccctgcagcaccac    960

     N  L  L  V  C  S  V  S  G  F  Y  P  G  S  I  E  V  R  W  F
 961 aacctcctggtctgctctgtgagtggtttctatccaggcagcattgaagtcaggtggttc   1020

     R  N  G  Q  E  E  K  A  G  V  V  S  T  G  L  I  Q  N  G  D
1021 cggaacggccaggaagagaaggctggggtggtgtccacaggcctgatccagaatggagat   1080

     W  T  F  Q  T  L  V  M  L  E  T  V  P  R  S  G  E  V  Y  T
1081 tggaccttccagaccctggtgatgctggaaacagttcctcggagtggagaggtttacacc   1140

     C  Q  V  E  H  P  S  V  T  S  P  L  T  V  E  W  R  A  R  S
1141 tgccaagtggagcacccaagtgtgacgagccctctcacagtggaatggagagcacggtct   1200

     E  S  A  Q  S  K  L  E  S  R  G  P  F  E  G  K  P  I  P  N
1201 gaatctgcacagagcaagctcgagtctagagggcccttcgaaggtaagcctatccctaac   1260

     P  L  L  G  L  D  S  T  R  T  G  H  H  H  H  H  H  *
1261 cctctcctcggtctcgattctacgcgtaccggtcatcatcaccatcaccattga         1314
```

7. Mutant DWP-7 (SEQ ID NOs:35 and 36)

```
     R  K  E  E  H  V  I  T  Q  A  E  F  Y  L  N  P  D  Q  S  G
   1 aggaaagaagaacatgtgatcacccaggccgagttctatctgaatcctgaccaatcaggc     60

     E  F  M  F  D  F  D  G  D  E  I  F  H  V  D  M  A  K  K  E
  61 gagtttatgtttgactttgatggtgatgagattttccatgtggatatggcaaagaaggag    120

     T  V  W  R  L  E  E  F  G  R  F  A  S  F  E  A  Q  G  A  L
 121 acggtctggcggcttgaagaatttggacgatttgccagctttgaggctcaaggtgcattg    180

     A  N  I  A  V  D  K  A  N  L  E  I  M  T  K  R  S  N  Y  T
 181 gccaacatagctgtggacaaagccaacctggaaatcatgacaaagcgctccaactatact    240

     P  I  T  N  V  P  P  E  V  T  V  L  T  N  S  P  V  E  L  R
 241 ccgatcaccaatgtacctccagaggtaactgtgctcacgaacagccctgtggaactgaga    300

     E  P  N  V  L  I  C  Y  I  D  K  F  T  P  P  V  V  N  V  T
 301 gagcccaacgtcctcatctgttacatcgacaagttcaccccaccagtggtcaatgtcacg    360
```

TABLE 1-continued

DNA and amino acid sequences of the evolved scHLA-DR1 variants.

W L R N G K P V T T G V S E T V F L P R
361 tggcttcgaaatggaaaacctgtcaccacaggagtgtcagagacagtcttcctgcccagg 420

E D H L F R K F H Y L P F L P S T E D V
421 gaagaccaccttttccgcaagttccactatctccccttcctgccctcaactgaggacgtt 480

Y D C R V E H W G L D E P L L K H W E F
481 tacgactgcagggtggagcactggggcttggatgagcctcttctcaagcactgggagttt 540

N A P S P L P E T T E N L G G G G S G G
541 aatgcaccaagccctctcccagagactacagagaacttaggaggcggcggctcaggtggc 600

G R S G G G G S G D T R P R F L W Q H K
601 ggccgctctggcggaggtggatccggggacacccgaccacgtttcttgtggcagcataag 660

F E C H F F N G T E R V R L L E R C I Y
661 tttgaatgtcatttcttcaatgggacggagcgggtgcggttgctggaaagatgcatctat 720

N Q E E S V R F D S D V G E Y R A V T E
721 aaccaagaggagtccgtgcgcttcgacagcgacgtgggggagtaccgggcggtgacggag 780

L G R P A A E Y W N S Q K D L L E Q R R
781 ctggggcggcctgctgccgagtactggaacagccagaaggacctcctggagcagaggcgg 840

A A A D T Y C R H N Y G V G E S F T V R
841 gccgcggcggacacctactgcagacacaactacggggttggtgagagcttcacagtgcgg 900

R R V E P K V T V Y P S K T Q P L Q H H
901 cggcgagttgagcctaaggtgactgtgtatccttcaaagacccagcccctgcagcaccac 960

N L L V C S V S G F Y P G S I E V R W F
961 aacctcctggtctgctctgtgagtggtttctatccaggcagcattgaagtcaggtggttc 1020

R N G Q E E K A G V V S T G L I Q N G D
1021 cggaacggccaggaagagaaggctggggtggtgtccacaggcctgatccagaatggagat 1080

W T F Q T L V M L E T V P R S G E V Y T
1081 tggaccttccagaccctggtgatgctggaaacagttcctcggagtggagaggtttacacc 1140

C Q V E H P S V T S P L T V E W R A R S
1141 tgccaagtggagcacccaagtgtgacgagccctctcacagtggaatggagagcacggtct 1200

E S A Q S K L E S R G P F E G K P I P N
1201 gaatctgcacagagcaagctcgagtctagagggcccttcgaaggtaagcctatccctaac 1260

P L L G L D S T R T G H H H H H H *
1261 cctctcctcggtctcgattctacgcgtaccggtcatcatcaccatcaccattga 1314

For mutants DO-1, DWP-5 and DWP-7, aa1 of α domain is Arg instead Ile and aa 193 (last amino acid of α chain) is Leu instead Val.

TABLE 2

DNA and amino acid sequences of the wild type scβ1α1 (A) and the engineered scβ1α1 mutant (B).

A. Wild-type scβ1α1 (SEQ ID NOs:37 and 38)

G D T R P R F L W Q L K F E C H F F N G
1 ggggacacccgaccacgtttcttgtggcagcttaagtttgaatgtcatttcttcaatggg 60

T E R V R L L E R C I Y N Q E E S V R F
61 acggagcgggtgcggttgctggaaagatgcatctataaccaagaggagtccgtgcgcttc 120

D S D V G E Y R A V T E L G R P D A E Y
121 gacagcgacgtgggggagtaccgggcggtgacggagctggggcggcctgatgccgagtac 180

W N S Q K D L L E Q R R A A V D T Y C R
181 tggaacagccagaaggacctcctggagcagaggcgggccgcggtggacacctactgcaga 240

H N Y G V G E S F T V Q R R V G S G G T
241 cacaactacggggttggtgagagcttcacagtgcagcggcgagttggctcaggaggtact 300

S K E E H V I I Q A E F Y L N P D Q S G
301 agtaaagaagaacatgtgatcatccaggccgagttctatctgaatcctgaccaatcaggc 360

TABLE 2-continued

DNA and amino acid sequences of the wild type scβ1α1 (A) and the engineered scβ1α1 mutant (B).

E F M F D F D G D E I F H V D M A K K E
361 gagtttatgtttgactttgatggtgatgagattttccatgtggatatggcaaagaaggag 420

T V W R L E E F G R F A S F E A Q G A L
421 acggtctggcggcttgaagaatttggacgatttgccagctttgaggctcaaggtgcattg 480

A N I A V D K A N L E I M T K R S N Y T
481 gccaacatagctgtggacaaagccaacctggaaatcatgacaaagcgctccaactatact 540

P I T N
541 ccgatcaccaat 552

β1 domain underlined and α1 domain in bold.
Aa1 of α1 is Ser instead Ile.

B. mutant $sc\beta1\alpha1_{L\beta11H,I\alpha ST}$ (SEQ ID NOs:39 and 40)

G D T R P R F L W Q H K F E C H F F N G
1 ggggacacccgaccacgtttcttgtggcagcataagtttgaatgtcatttcttcaatggg 60

T E R V R L L E R C I Y N Q E E S V R F
61 acggagcgggtgcggttgctggaaagatgcatctataaccaagaggagtccgtgcgcttc 120

D S D V G E Y R A V T E L G R P D A E Y
121 gacagcgacgtgggggagtaccgggcggtgacggagctggggcggcctgatgccgagtac 180

W N S Q K D L L E Q R R A A V D T Y C R
181 tggaacagccagaaggacctcctggagcagaggcgggccgcggtggacacctactgcaga 240

H N Y G V G E S F T V Q R R V G S G G T
241 cacaactacggggttggtgagagcttcacagtgcagcggcgagttggctcaggaggtact 300

S K E E H V I T Q A E F Y L N P D Q S G
301 agtaaagaagaacatgtgatcacccaggccgagttctatctgaatcctgaccaatcaggc 360

E F M F D F D G D E I F H V D M A K K E
361 gagtttatgtttgactttgatggtgatgagattttccatgtggatatggcaaagaaggag 420

T V W R L E E F G R F A S F E A Q G A L
421 acggtctggcggcttgaagaatttggacgatttgccagctttgaggctcaaggtgcattg 480

A N I A V D K A N L E I M T K R S N Y T
481 gccaacatagctgtggacaaagccaacctggaaatcatgacaaagcgctccaactatact 540

P I T N
541 ccgatcaccaat 552

TABLE 3

DNA and amino acid sequences of two forms of single chain HLA-A2 molecules.

A. scHLA-A2 (SEQ ID NOs:41 and 42)

M I Q R T P K I Q V Y S R H P A E N G K
1 atgatccagcgtactccaaagattcaggtttactcacgtcatccagcagagaatggaaag 60

S N F L N C Y V S G F H P S D I E V D L
61 tcaaatttcctgaattgctatgtgtctgggtttcatccatccgacattgaagttgactta 120

L K N G E R I E K V E H S D L S F S K D
121 ctgaagaatggagagagaattgaaaaagtggagcattcagacttgtctttcagcaaggac 180

W S F Y L L Y Y T E F T P T E K D E Y A
181 tggtctttctatctcttgtactacactgaattcacccccactgaaaaagatgagtatgcc 240

C R V N H V T L S Q P E I V K W D R D M
241 tgccgtgtgaaccatgtgactttgtcacagcccgagatagttaagtgggatcgagacatg 300

G G G G S G G G G S G G G G S G S H S M
301 ggaggcggcggctcgggtggcggcggctctggcggaggtggatccggctctcactccatg 360

R Y F F T S V S R P G R G E P R F I A V
361 aggtatttcttcacatccgtgtcccggcccggccgcggggagccccgcttcatcgcagtg 420

G Y V D D T Q F V R F D S D A A S Q R M
421 ggctacgtggacgacacgcagttcgtgcggttcgacagcgacgccgcgagccagaggatg 480

TABLE 3-continued

DNA and amino acid sequences of two forms of single chain HLA-A2 molecules.

```
     E  P  R  A  P  W  I  E  Q  E  G  P  E  Y  W  D  G  E  T  R
 481 gagccgcgggcgccgtggatagagcaggagggtccggagtattgggacggggagacacgg   540

     K  V  K  A  H  S  Q  T  H  R  V  D  L  G  T  L  R  G  Y  Y
 541 aaagtgaaggcccactcacagactcaccgagtggacctggggaccctgcgcggctactac   600

     N  Q  S  E  A  G  S  H  T  V  Q  R  M  Y  G  C  D  V  G  S
 601 aaccagagcgaggccggttctcacaccgtccagaggatgtatggctgcgacgtggggtcg   660

     D  W  R  F  L  R  G  Y  H  Q  Y  A  Y  D  G  K  D  Y  I  A
 661 gactggcgcttcctccgcgggtaccaccagtacgcctacgacggcaaggattacatcgcc   720

     L  K  E  D  L  R  S  W  T  A  A  D  M  A  A  Q  T  T  K  H
 721 ctgaaagaggacctgcgctcttggaccgcggcggacatggcagctcagaccaccaagcac   780

     K  W  E  A  A  H  V  A  E  Q  L  R  A  Y  L  E  G  T  C  V
 781 aagtgggaggcggcccatgtggcggagcagttgagagcctacctggagggcacgtgcgtg   840

     E  W  L  R  R  Y  L  E  N  G  K  E  T  L  Q  R  T  D  A  P
 841 gagtggctccgcagatacctggagaacgggaaggagacgctgcagcgcacggacgccccc   900

     K  T  H  M  T  H  H  A  V  S  D  H  E  A  T  L  R  C  W  A
 901 aaaacgcatatgactcaccacgctgtctctgaccatgaagccaccctgaggtgctgggcc   960

     L  S  F  Y  P  A  E  I  T  L  T  W  Q  R  D  G  E  D  Q  T
 961 ctgagcttctaccctgcggagatcacactgacctggcagcgggatggggaggaccagacc  1020

     Q  D  T  E  L  V  E  T  R  P  A  G  D  G  T  F  Q  K  W  A
1021 caggacacggagctcgtggagaccaggcctgcaggggatggaaccttccagaagtgggcg  1080

     A  V  V  V  P  S  G  Q  E  Q  R  Y  T  C  H  V  Q  H  E  G
1081 gctgtggtggtgccttctggacaggagcagagatacacctgccatgtgcagcatgagggt  1140

     L  P  K  P  L  T  L  R  W  E  L  E  S  R  G  P  F  E  G  K
1141 ttgcccaagcccctcaccctgagatgggaactcgagtctagagggcccttcgaaggtaag  1200

     P  I  P  N  P  L  L  G  L  D  S  T  R  T  G  H  H  H  H  H
1201 cctatccctaaccctctcctcggtctcgattctacgcgtaccggtcatcatcaccatcac  1260

     H  *
1261 cattga                                                        1266

B. pbsHLA-A2 (SEQ ID NOs:43 and 44)
     M  G  S  H  S  M  R  Y  F  F  T  S  V  S  R  P  G  R  G  E
   1 atgggctctcactccatgaggtatttcttcacatccgtgtcccggcccggccgcggggag    60

     P  R  F  I  A  V  G  Y  V  D  D  T  Q  F  V  R  F  D  S  D
  61 ccccgcttcatcgcagtgggctacgtggacgacacgcagttcgtgcggttcgacagcgac   120

     A  A  S  Q  R  M  E  P  R  A  P  W  I  E  Q  E  G  P  E  Y
 121 gccgcgagccagaggatggagccgcgggcgccgtggatagagcaggagggtccggagtat   180

     W  D  G  E  T  R  K  V  K  A  H  S  Q  T  H  R  V  D  L  G
 181 tgggacggggagacacggaaagtgaaggcccactcacagactcaccgagtggacctgggg   240

     T  L  R  G  Y  Y  N  Q  S  E  A  G  S  H  T  V  Q  R  M  Y
 241 accctgcgcggctactacaaccagagcgaggccggttctcacaccgtccagaggatgtat   300

     G  C  D  V  G  S  D  W  R  F  L  R  G  Y  H  Q  Y  A  Y  D
 301 ggctgcgacgtggggtcggactggcgcttcctccgcgggtaccaccagtacgcctacgac   360

     G  K  D  Y  I  A  L  K  E  D  L  R  S  W  T  A  A  D  M  A
 361 ggcaaggattacatcgccctgaaagaggacctgcgctcttggaccgcggcggacatggca   420

     A  Q  T  T  K  H  K  W  E  A  A  H  V  A  E  Q  L  R  A  Y
 421 gctcagaccaccaagcacaagtgggaggcggcccatgtggcggagcagttgagagcctac   480

     L  E  G  T  C  V  E  W  L  R  R  Y  L  E  N  G  K  E  T  L
 481 ctggagggcacgtgcgtggagtggctccgcagatacctggagaacgggaaggagacgctg   540

     Q
 541 cag                                                           543
```

REFERENCES

Pandey, A. and M. Mann, *Nature,* 2000. 405(6788): p. 837-46.

Gygi, S. P., et al., *Nat Biotechnol,* 1999. 17(10): p. 994-9.

Emili, A. Q. and G. Cagney, *Nat Biotechnol,* 2000. 18(4): p. 393-7.

de Wildt, R. M., et al., *Nat Biotechnol,* 2000. 18(9): p. 989-94.

Cahill, D. J., *J Immunol Methods,* 2001. 250(1-2): p. 81-91.

Stanfield, R. L. and I. A. Wilson, *Curr Opin Struct Biol,* 1995. 5(1): p. 103-13.

Schneider, S., et al., *Nat Biotechnol,* 1999. 17(2): p. 170-5.

Madden, D. R., *Annu Rev Immunol,* 1995. 13: p. 587-622.

Pinilla, C., et al., *Curr Opin Immunol,* 1999. 11(2): p. 193-202.

Stern, L. J. and D. C. Wiley, *Cell,* 1992. 68(3): p. 465-77.

Arnold, F. H., F. M. Richards, and D. Eisenberg, eds. *Advanced Protein Chemistry*. Vol. 55. 2001, Academic Press.

Zhu, X., et al., *Eur J Immunol,* 1997. 27(8): p. 1933-41.

Crameri, A., et al., *Nature,* 1998. 391(6664): p. 288-91.

Shusta, E. V., et al., *J Mol Biol,* 1999. 292(5): p. 949-56.

Leary, J. F., *Methods Cell Biol,* 1994. 42(Pt B): p. 331-58.

Townsend, A. R., et al., *The epitopes of influenza nucleoprotein recognized by cytotoxic T lymphocytes can be defined with short synthetic peptides*. Cell, 1986. 44(6): p. 959-68.

Buus, S., *Description and prediction of peptide-MHC binding: the 'human MHC project'*. Curr Opin Immunol, 1999. 11(2): p. 209-13.

Garboczi, D. N., D. R. Madden, and D. C. Wiley, *Five viral peptide-HLA-A2 co-crystals. Simultaneous space group determination and X-ray data collection*. J Mol Biol, 1994. 239(4): p. 581-7.

Garboczi, D. N., D. T. Hung, and D. C. Wiley, *HLA-A2-peptide complexes: refolding and crystallization of molecules expressed in Escherichia coli and complexed with single antigenic peptides*. Proc Natl Acad Sci USA, 1992. 89(8): p. 3429-33.

Boder, E. T. and K. D. Wittrup, *Yeast surface display for screening combinatorial polypeptide libraries*. Nat Biotechnol, 1997. 15(6): p. 553-7.

Arnold, F. H., *Design by directed evolution*. Acct. Chem. Res., 1998. 31(3): p. 125-131.

Lin, Z., T. Thorsen, and F. H. Arnold, *Functional expression of horseradish peroxidase in E. coli by directed evolution*. Biotechnol Prog, 1999. 15(3): p. 467-71.

Kieke, M. C., et al., *Selection of functional T cell receptor mutants from a yeast surface-display library*. Proc Natl Acad Sci USA, 1999. 96(10): p. 5651-6.

Madden, D. R., D. N. Garboczi, and D. C. Wiley, *The antigenic identity of peptide-MHC complexes: a comparison of the conformations of five viral peptides presented by HLA-A2*. Cell, 1993. 75(4): p. 693-708.

Joshi, R. V., J. A. Zarutskie, and L. J. Stern, *A three-step kinetic mechanism for peptide binding to MHC class II proteins*. Biochemistry, 2000. 39(13): p. 3751-62.

Zhao, H., et al., *Methods for optimizing industrial enzymes by directed evolution*, in *Manual of Industrial Microbiology and Biotechnology,* 2nd Ed., A. L. Demain and J. E. Davies, Editors. 1999, ASM Press: Washington, D.C. p. 597-604.

VanAntwerp, J. J. and K. D. Wittrup, *Fine affinity discrimination by yeast surface display and flow cytometry*. Biotechnol Prog, 2000. 16(1): p. 31-7.

Tissot, A. C., et al., *Viral escape at the molecular level explained by quantitative T-cell Receptor/Peptide/MHC interactions and the crystal structure of a Peptide/MHC complex*. J Mol Biol, 2000. 302(4): p. 873-85.

Bertoletti, A., et al., *Natural variants of cytotoxic epitopes are T-cell receptor antagonists for antiviral cytotoxic T cells*. Nature, 1994. 369(6479): p. 407-10.

Klenerman, P., et al., *Cytotoxic T-cell activity antagonized by naturally occurring HIV-1 Gag variants*. Nature, 1994. 369(6479): p. 403-7.

Jain, R. K. and L. T. Baxter, *Mechanisms of heterogeneous distribution of monoclonal antibodies and other macromolecules in tumors: significance of elevated interstitial pressure*. Cancer Res, 1988. 48(24 Pt 1): p. 7022-32.

Strominger, J. L., and Wiley, D. C. (1995) *JAMA* 274, 1074-1076

Tiwari, J. L., and Terasaki, P. I. (1981) *Prog Clin Biol Res* 58, 151-163

Singh, N., Agrawal, S., and Rastogi, A. K. (1997) *Emerging Infectious Diseases* 3, 41-49

Maile, R., Wang, B., Schooler, W., Meyer, A., Collins, E. J., and Frelinger, J. A. (2001) *J Immunol* 167, 3708-3714

Casares, S., Hurtado, A., McEvoy, R. C., Sarukhan, A., von Boehmer, H., and Brumeanu, T. D. (2002) *Nat Immunol* 3, 383-391

Masteller, E. L., Warner, M. R., Ferlin, W., Judkowski, V., Wilson, D., Glaichenhaus, N., and Bluestone, J. A. (2003) *J Immunol* 171, 5587-5595

Sharma, S. D., Nag, B., Su, X. M., Green, D., Spack, E., Clark, B. R., and Sriram, S. (1991) *Proc Natl Acad Sci USA* 88, 11465-11469

Kwok, W. W., Ptacek, N. A., Liu, A. W., and Buckner, J. H. (2002) *J Immunol Methods* 268, 71-81

Boehncke, W. H., Takeshita, T., Pendleton, C. D., Houghten, R. A., Sadegh-Nasseri, S., Racioppi, L., van der Burg, S. H., Visseren, M. J., Brandt, R. M., Kast, W. M., and Melief, C. J. (1996) *J Immunol* 156, 3308-3314

Hackett, C. J., and Sharma, O. K. (2002) *Nat Immunol* 3, 887-889

Arnold, F. H. (2001) *Nature* 409, 253-257

Schmidt-Dannert, C. (2001) *Biochemistry* 40, 13125-13136

Waldo, G. S. (2003) *Curr Opin Chem Biol* 7, 33-38

Pedelacq, J. D., Piltch, E., Liong, E. C., Berendzen, J., Kim, C. Y., Rho, B. S., Park, M. S., Terwilliger, T. C., and Waldo, G. S. (2002) *Nat Biotechnol* 20, 927-932

Bulter, T., Alcalde, M., Sieber, V., Meinhold, P., Schlachtbauer, C., and Arnold, F. H. (2003) *Appl Environ Microbiol* 69, 987-995

Kalandadze, A., Galleno, M., Foncerrada, L., Strominger, J. L., and Wucherpfennig, K. W. (1996) *Journal of Biological Chemistry* 271, 20156-20162

Scott, C. A., Garcia, K. C., Carbone, F. R., Wilson, I. A., and Teyton, L. (1996) *J Exp Med* 183, 2087-2095

Kozono, H., White, J., Clements, J., Marrack, P., and Kappler, J. (1994) *Nature* 369, 151-154

Scheirle, A., Takacs, B., Kremer, L., Marin, F., and Sinigaglia, F. (1992) *J Immunol* 149, 1994-1999

Boder, E. T., and Wittrup, K. D. (1998) *Biotechnol Prog* 14, 55-62.

Yeung, Y. A., and Wittrup, K. D. (2002) *Biotechnol Prog* 18, 212-220

Wittrup, K. D. (2001) *Curr Opin Biotechnol* 12, 395-399

Boder, E. T., Midelfort, K. S., and Wittrup, K. D. (2000) *Proc Natl Acad Sci USA* 97, 10701-10705

Feldhaus, M. J., Siegel, R. W., Opresko, L. K., Coleman, J. R., Feldhaus, J. M., Yeung, Y. A., Cochran, J. R., Heinzelman, P., Colby, D., Swers, J., Graff, C., Wiley, H. S., and Wittrup, K. D. (2003) *Nat Biotechnol* 21, 163-170

Kieke, M. C., Cho, B. K., Boder, E. T., Kranz, D. M., and Wittrup, K. D. (1997) *Protein Eng* 10, 1303-1310

Holler, P. D., Holman, P. O., Shusta, E. V., O'Herrin, S., Wittrup, K. D., and Kranz, D. M. (2000) *Proceedings of the National Academy of Sciences of the United States of America* 97, 5387-5392

Kieke, M. C., Shusta, E. V., Boder, E. T., Teyton, L., Wittrup, K. D., and Kranz, D. M. (1999) *Proc Natl Acad Sci USA* 96, 5651-5656

Kieke, M. C., Sundberg, E., Shusta, E. V., Mariuzza, R. A., Wittrup, K. D., and Kranz, D. M. (2001) *J Mol Biol* 307, 1305-1315

Starwalt, S. E., Masteller, E. L., Bluestone, J. A., and Kranz, D. M. (2003) *Protein Eng* 16, 147-156

Schweickhardt, R. L., Jiang, X., Garone, L. M., and Brondyk, W. H. (2003) *J Biol Chem* 278, 28961-28967

Horton, R. M., Ho, S. N., Pullen, J. K., Hunt, H. D., Cai, Z., and Pease, L. R. (1993) *Methods Enzymol* 217, 270-279

Oldenburg, K. R., Vo, K. T., Michaelis, S., and Paddon, C. (1997) *Nucleic Acids Res* 25, 451-452

Prado, F., and Aguilera, A. (1994) *Current Genetics* 25, 180-183

Zhao, H., Giver, L., Shao, Z., Affholter, J. A., and Arnold, F. H. (1998) *Nat Biotechnol* 16, 258-261

Gietz, R. D., and Woods, R. A. (2002) *Guide to Yeast Genetics and Molecular and Cell Biology, Pt B* 350, 87-96

Orr, B. A., Carr, L. M., Wittrup, K. D., Roy, E. J., and Kranz, D. M. (2003) *Biotechnol Prog* 19, 631-638

Stern, L. J., Brown, J. H., Jardetzky, T. S., Gorga, J. C., Urban, R. G., Strominger, J. L., and Wiley, D. C. (1994) *Nature* 368, 215-221

Shusta, E. V., Holler, P. D., Kieke, M. C., Kranz, D. M., and Wittrup, K. D. (2000) *Nat Biotechnol* 18, 754-759

Adams, T. E., Bodmer, J. G., and Bodmer, W. F. (1983) *Immunology* 50, 613-624

Boder, E. T., and Wittrup, K. D. (2000) *Methods Enzymol* 328, 430-444

Zhao, H., Shen, Z. M., Kahn, P. C., and Lipke, P. N. (2001) *J Bacteriol* 183, 2874-2880

LaPan, K. E., Klapper, D. G., and Frelinger, J. A. (1992) *Hybridoma* 11, 217-223

Santambrogio, L., Sato, A. K., Fischer, F. R., Dorf, M. E., and Stern, L. J. (1999) *Proc Natl Acad Sci USA* 96, 15050-15055

Busch, R., and Rothbard, J. B. (1990) *Journal of Immunological Methods* 134, 1-22

Frayser, M., Sato, A. K., Xu, L., and Stern, L. J. (1999) *Protein Expr Purif* 15, 105-114

Ueda, M., and Tanaka, A. (2000) *Biotechnology Advances* 18, 121-140

Hammond, C., and Helenius, A. (1994) *J Cell Biol* 126, 41-52

Chang, J. W., Mechling, D. E., Bachinger, H. P., and Burrows, G. G. (2001) *Journal of Biological Chemistry* 276, 24170-24176

Burley, S. K., and Petsko, G. A. (1986) *Febs Letters* 203, 139-143

Burley, S. K., and Petsko, G. A. (1988) *Adv Protein Chem* 39, 125-189

Zauhar, R. J., Colbert, C. L., Morgan, R. S., and Welsh, W. J. (2000) *Biopolymers* 53, 233-248

Reid, K. S. C., Lindley, P. F., and Thornton, J. M. (1985) *FEBS Lett* 190, 209-213

Todd, J. A., Bell, J. I., and Mcdevitt, H. O. (1987) *Nature* 329, 599-604

Sato, A. K., Stumiolo, T., Sinigaglia, F., and Stern, L. J. (1999) *Hum Immunol* 60, 1227-1236

Waldburger, C. D., Jonsson, T., and Sauer, R. T. (1996) *Proceedings of the National Academy of Sciences of the United States of America* 93, 2629-2634

Doebele, R. C., Pashine, A., Liu, W., Zaller, D. M., Belmares, M., Busch, R., and Mellins, E. D. (2003) *Journal of Immunology* 170, 4683-4692

Sato, A. K., Zarutskie, J. A., Rushe, M. M., Lomakin, A., Natarajan, S. K., Sadegh-Nasseri, S., Benedek, G. B., and Stern, L. J. (2000) *Journal of Biological Chemistry* 275, 2165-2173

Natarajan, S. K., Assadi, M., and Sadegh-Nasseri, S. (1999) *Journal of Immunology* 162, 4030-4036

Ferlin, W., Glaichenhaus, N., and Mougneau, E. (2000) *Current Opinion in Immunology* 12, 670-675

Shusta, E. V., Raines, R. T., Pluckthun, A., and Wittrup, K. D. (1998) *Nature Biotechnology* 16, 773-777

U.S. Pat. No. 6,391,625 (May 21, 2002); WO 02/54070; WO 01/83827

We claim:

1. A universal peptide or protein binding scaffold comprising: a library of mutants of a peptide or protein binding scaffold of MHC class II DR1 peptide binding domains having an affinity for a ligand between $10^{-6}$ and $10^{-9}$ molar and having a point mutation L11H in the β1 domain.

2. The scaffold of claim 1, wherein the library of mutants is displayed on a yeast cell surface.

3. The scaffold of claim 1, wherein the scaffold is presented in a protein chip.

4. A protein chip comprising: a substrate and mutants of a peptide or protein binding scaffold of MHC class II DR1 peptide binding domains having a point mutation L11H in the β1 domain bound to the substrate, wherein the peptide has an affinity for a ligand between $10^{-6}$ and $10^{-9}$ molar.

5. The protein chip of claim 4, wherein the mutants are bound to the substrate in a pattern.

6. The protein chip of claim 4, wherein the substrate is selected from the group consisting of: glass, polycarbonate, polytetrafluoroethylene, polystyrene, silicon oxide and silicon nitride.

7. A method of selecting proteins or peptides that bind to a peptide binding scaffold comprising: preparing a library of mutants of a peptide binding domain of MHC class II peptide binding domains having a point mutation L11H in the β1 domain; contacting said library with labeled peptides or proteins; and selecting those mutants that bind to labeled peptides or proteins with a desired affinity.

8. The method of claim 7, wherein the peptide binding domain is a DR1 protein variant of a MHC class II binding domain.

9. The method of claim 7, wherein the desired affinity is between $10^{-6}$ and $10^{-9}$ molar.

10. The method of claim 7, wherein the selection is performed by fluorescence activated cell sorting.

11. The method of claim 7, wherein the library of mutants is displayed on a yeast cell surface.

12. The method of claim 7, further comprising selecting those mutants having the highest fluorescence.

13. The method of claim 7, wherein the library of mutants is in the form of protein chips.

14. The method of claim 13, wherein the protein chips are in a high throughput format.

* * * * *

SEQUENCE LISTING

```
<160> NUMBER OF SEQ ID NOS: 47

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

Pro Lys Tyr Val Lys Gln Asn Thr Leu Lys Leu Ala Thr
1               5                   10


<210> SEQ ID NO 2
<211> LENGTH: 41
<212> TYPE: DNA
<213> ORGANISM: Artificial sequence
<220> FEATURE:
<223> OTHER INFORMATION: Synthetic nucleotide primer
```

<400> SEQUENCE: 2
gtaccaggat ccagtgtggt ggaaggggac acccgaccac g 41

<210> SEQ ID NO 3
<211> LENGTH: 54
<212> TYPE: DNA
<213> ORGANISM: Artificial sequence
<220> FEATURE:
<223> OTHER INFORMATION: Synthetic nucleotide primer

<400> SEQUENCE: 3
gccagagcgg ccgccacctg agccgccgcc tcctaagttc tctgtagtct ctgg 54

<210> SEQ ID NO 4
<211> LENGTH: 49
<212> TYPE: DNA
<213> ORGANISM: Artificial sequence
<220> FEATURE:
<223> OTHER INFORMATION: Synthetic nucleotide primer

<400> SEQUENCE: 4
tcaggtggcg gccgctctgg cggaggtgga tccggggaca cccgaccac 49

<210> SEQ ID NO 5
<211> LENGTH: 37
<212> TYPE: DNA
<213> ORGANISM: Artificial sequence
<220> FEATURE:
<223> OTHER INFORMATION: Synthetic nucleotide primer

<400> SEQUENCE: 5
ccctctagac tcgagcttgc tctgtgcaga ttcagac 37

<210> SEQ ID NO 6
<211> LENGTH: 41
<212> TYPE: DNA
<213> ORGANISM: Artificial sequence
<220> FEATURE:
<223> OTHER INFORMATION: Synthetic nucleotide primer

<400> SEQUENCE: 6
gtaccaggat ccagtgtggt ggaaggggac acccgaccac g 41

<210> SEQ ID NO 7
<211> LENGTH: 36
<212> TYPE: DNA
<213> ORGANISM: Artificial sequence
<220> FEATURE:
<223> OTHER INFORMATION: Synthetic nucleotide primer

<400> SEQUENCE: 7
ccctctagac tcgagtaagt tctctgtagt ctctgg 36

<210> SEQ ID NO 8
<211> LENGTH: 44
<212> TYPE: DNA
<213> ORGANISM: Artificial sequence
<220> FEATURE:
<223> OTHER INFORMATION: Synthetic nucleotide primer

<400> SEQUENCE: 8
cttctttact agtacctcct gagccaactc gccgctgcac tgtg 44

<210> SEQ ID NO 9
<211> LENGTH: 22

-continued

<212> TYPE: DNA
<213> ORGANISM: artificial sequence
<220> FEATURE:
<223> OTHER INFORMATION: Synthetic nucleotide primer

<400> SEQUENCE: 9
ggctcaggag gtactagtaa ag 22

<210> SEQ ID NO 10
<211> LENGTH: 37
<212> TYPE: DNA
<213> ORGANISM: Artificial sequence
<220> FEATURE:
<223> OTHER INFORMATION: Synthetic nucleotide primer

<400> SEQUENCE: 10
ccctctagac tcgagattgg tgatcggagt atagttg 37

<210> SEQ ID NO 11
<211> LENGTH: 66
<212> TYPE: DNA
<213> ORGANISM: Artificial sequence
<220> FEATURE:
<223> OTHER INFORMATION: Synthetic nucleotide primer

<400> SEQUENCE: 11
ggtcgggatc tgtacgacga tgacgataag gtaccaggat ccagtgggga cacccgacca 60
cgtttc 66

<210> SEQ ID NO 12
<211> LENGTH: 72
<212> TYPE: DNA
<213> ORGANISM: Artificial sequence
<220> FEATURE:
<223> OTHER INFORMATION: Synthetic nucleotide primer
<220> FEATURE:
<221> NAME/KEY: misc_feature
<222> LOCATION: (18)..(18)
<223> OTHER INFORMATION: R at position 18 is A or G.

<400> SEQUENCE: 12
gatagaactc ggcctggrtg atcacatgtt cttctttact agtacctcct gagccaactc 60
gccgccgcac tg 72

<210> SEQ ID NO 13
<211> LENGTH: 20
<212> TYPE: DNA
<213> ORGANISM: Artificial sequence
<220> FEATURE:
<223> OTHER INFORMATION: Synthetic nucleotide primer

<400> SEQUENCE: 13
ggcccgcctc tgctccagga 20

<210> SEQ ID NO 14
<211> LENGTH: 19
<212> TYPE: DNA
<213> ORGANISM: Artificial sequence
<220> FEATURE:
<223> OTHER INFORMATION: Synthetic nucleotide primer

<400> SEQUENCE: 14
cggcgagttg gctcaggag 19

<210> SEQ ID NO 15

<211> LENGTH: 22
<212> TYPE: DNA
<213> ORGANISM: Artificial sequence
<220> FEATURE:
<223> OTHER INFORMATION: Synthetic nucleotide primer

<400> SEQUENCE: 15
agtatgtgta aagttggtaa cg 22

<210> SEQ ID NO 16
<211> LENGTH: 63
<212> TYPE: DNA
<213> ORGANISM: Artificial sequence
<220> FEATURE:
<223> OTHER INFORMATION: Synthetic nucleotide primer

<400> SEQUENCE: 16
ggcggctcgg gtggcggcgg ctctggcgga ggtggatccg gctctcactc catgaggtat 60
ttc 63

<210> SEQ ID NO 17
<211> LENGTH: 33
<212> TYPE: DNA
<213> ORGANISM: Artificial sequence
<220> FEATURE:
<223> OTHER INFORMATION: Synthetic nucleotide primer

<400> SEQUENCE: 17
ataccgctcg agttcccatc tcagggtgag ggg 33

<210> SEQ ID NO 18
<211> LENGTH: 43
<212> TYPE: DNA
<213> ORGANISM: Artificial sequence
<220> FEATURE:
<223> OTHER INFORMATION: Synthetic nucleotide primer

<400> SEQUENCE: 18
gatcgaagcc agtgtggtgg aaatgatcca gcgtactcca aag 43

<210> SEQ ID NO 19
<211> LENGTH: 60
<212> TYPE: DNA
<213> ORGANISM: Artificial sequence
<220> FEATURE:
<223> OTHER INFORMATION: Synthetic nucleotide primer

<400> SEQUENCE: 19
acctccgcca gagccgccgc cacccgagcc gccgcctccc atgtctcgat cccacttaac 60

<210> SEQ ID NO 20
<211> LENGTH: 43
<212> TYPE: DNA
<213> ORGANISM: Artificial sequence
<220> FEATURE:
<223> OTHER INFORMATION: Synthetic nucleotide primer

<400> SEQUENCE: 20
gatcgaagcc agtgtggtgg aaatgggctc tcactccatg agg 43

<210> SEQ ID NO 21
<211> LENGTH: 30
<212> TYPE: DNA
<213> ORGANISM: Artificial sequence
<220> FEATURE:
<223> OTHER INFORMATION: Synthetic nucleotide primer -continued

<400> SEQUENCE: 21

```
ataccgctcg agctgcagcg tctccttccc                                    30


<210> SEQ ID NO 22
<211> LENGTH: 9
<212> TYPE: PRT
<213> ORGANISM: Artificial sequence
<220> FEATURE:
<223> OTHER INFORMATION: Synthetic peptide

<400> SEQUENCE: 22

Ile Leu Lys Glu Cys Val His Gly Val
1               5


<210> SEQ ID NO 23
<211> LENGTH: 1380
<212> TYPE: DNA
<213> ORGANISM: Artificial sequence
<220> FEATURE:
<223> OTHER INFORMATION: Sequence of mutant H2-1
<220> FEATURE:
<221> NAME/KEY: CDS
<222> LOCATION: (1)..(1377)

<400> SEQUENCE: 23

ccc aag tat gtt aag caa aac acc ctg aag ttg gca aca ggt acc ggt       48
Pro Lys Tyr Val Lys Gln Asn Thr Leu Lys Leu Ala Thr Gly Thr Gly
1               5                   10                  15

ggc tca cta gtg cca cgg ggc tct gga gga ggt ggg tcc ggg gac acc       96
Gly Ser Leu Val Pro Arg Gly Ser Gly Gly Gly Gly Ser Gly Asp Thr
            20                  25                  30

cga cca cgt ttc ttg tgg cag cat aag ttt gaa tgt cat ttc ttc aat      144
Arg Pro Arg Phe Leu Trp Gln His Lys Phe Glu Cys His Phe Phe Asn
        35                  40                  45

ggg acg gag cgg gtg cgg ttg ctg gaa aga tgc atc tat aac caa gag      192
Gly Thr Glu Arg Val Arg Leu Leu Glu Arg Cys Ile Tyr Asn Gln Glu
    50                  55                  60

gag tcc gtg cgc ttc gac agc gac gtg ggg gag tac cgg gcg gtg acg      240
Glu Ser Val Arg Phe Asp Ser Asp Val Gly Glu Tyr Arg Ala Val Thr
65                  70                  75                  80

gag ctg ggg cgg cct gat gcc gag tac tgg aac agc cag aag gac ctc      288
Glu Leu Gly Arg Pro Asp Ala Glu Tyr Trp Asn Ser Gln Lys Asp Leu
                85                  90                  95

ctg gag cag agg cgg gcc gcg gtg gac acc tac tgc aga cac aac tac      336
Leu Glu Gln Arg Arg Ala Ala Val Asp Thr Tyr Cys Arg His Asn Tyr
            100                 105                 110

ggg gtt ggt gag agc ttc aca gtg cag cgg cga gtt gag cct aag gtg      384
Gly Val Gly Glu Ser Phe Thr Val Gln Arg Arg Val Glu Pro Lys Val
        115                 120                 125

act gtg tat cct tca aag acc cag ccc ctg cag cac cac aac ctc ctg      432
Thr Val Tyr Pro Ser Lys Thr Gln Pro Leu Gln His His Asn Leu Leu
    130                 135                 140

gtc tgc tct gtg agt ggt ttc tat cca ggc agc att gaa gtc agg tgg      480
Val Cys Ser Val Ser Gly Phe Tyr Pro Gly Ser Ile Glu Val Arg Trp
145                 150                 155                 160

ttc cgg aac ggc cag gaa gag aag gct ggg gtg gtg tcc aca ggc ctg      528
Phe Arg Asn Gly Gln Glu Glu Lys Ala Gly Val Val Ser Thr Gly Leu
                165                 170                 175

atc cag aat gga gat tgg acc ttc cag acc ctg gtg atg ctg gaa aca      576
Ile Gln Asn Gly Asp Trp Thr Phe Gln Thr Leu Val Met Leu Glu Thr
            180                 185                 190
```

-continued

```
gtt cct cgg agt gga gag gtt tac acc tgc caa gtg gag cac cca agt      624
Val Pro Arg Ser Gly Glu Val Tyr Thr Cys Gln Val Glu His Pro Ser
        195                 200                 205

gtg acg agc cct ctc aca gtg gaa tgg aga gca cgg tct gaa tct gca      672
Val Thr Ser Pro Leu Thr Val Glu Trp Arg Ala Arg Ser Glu Ser Ala
    210                 215                 220

cag aga tct gga ggt gga ggc tca gga ggt act agt aaa gaa gaa cat      720
Gln Arg Ser Gly Gly Gly Gly Ser Gly Gly Thr Ser Lys Glu Glu His
225                 230                 235                 240

gtg atc atc cag gcc gag ttc tat ctg aat cct gac caa tca ggc gag      768
Val Ile Ile Gln Ala Glu Phe Tyr Leu Asn Pro Asp Gln Ser Gly Glu
                245                 250                 255

ttt atg ttt gac ttt gat ggt gat gag att ttc cat gtg gat atg gca      816
Phe Met Phe Asp Phe Asp Gly Asp Glu Ile Phe His Val Asp Met Ala
            260                 265                 270

aag aag gag acg gtc tgg cgg ctt gaa gaa ttt gga cga ttt gcc agc      864
Lys Lys Glu Thr Val Trp Arg Leu Glu Glu Phe Gly Arg Phe Ala Ser
        275                 280                 285

ttt gag gct caa ggt gca ttg gcc aac ata gct gtg gac aaa gcc aac      912
Phe Glu Ala Gln Gly Ala Leu Ala Asn Ile Ala Val Asp Lys Ala Asn
    290                 295                 300

ctg gaa atc atg aca aag cgc tcc aac tat act ccg atc acc aat gta      960
Leu Glu Ile Met Thr Lys Arg Ser Asn Tyr Thr Pro Ile Thr Asn Val
305                 310                 315                 320

cct cca gag gta act gtg ctc acg aac agc cct gtg gaa ctg aga gag     1008
Pro Pro Glu Val Thr Val Leu Thr Asn Ser Pro Val Glu Leu Arg Glu
                325                 330                 335

ccc aac gtc ctc atc tgt ttc atc gac aag ttc acc cca cca gtg gtc     1056
Pro Asn Val Leu Ile Cys Phe Ile Asp Lys Phe Thr Pro Pro Val Val
            340                 345                 350

aat gtc acg tgg ctt cga aat gga aaa cct gtc acc aca gga gtg tca     1104
Asn Val Thr Trp Leu Arg Asn Gly Lys Pro Val Thr Thr Gly Val Ser
        355                 360                 365

gag aca gtc ttc ctg ccc agg gaa gac cac ctt ttc cgc aag ttc cac     1152
Glu Thr Val Phe Leu Pro Arg Glu Asp His Leu Phe Arg Lys Phe His
    370                 375                 380

tat ctc ccc ttc ctg ccc tca act gag gac gtt tac gac tgc agg gtg     1200
Tyr Leu Pro Phe Leu Pro Ser Thr Glu Asp Val Tyr Asp Cys Arg Val
385                 390                 395                 400

gag cac tgg ggc ttg gat gag cct ctt ctc aag cac tgg gag ttt gat     1248
Glu His Trp Gly Leu Asp Glu Pro Leu Leu Lys His Trp Glu Phe Asp
                405                 410                 415

gca cca agc cct ctc cca gag act aca gag aac tta ctc gag tct aga     1296
Ala Pro Ser Pro Leu Pro Glu Thr Thr Glu Asn Leu Leu Glu Ser Arg
            420                 425                 430

ggg ccc ttc gaa ggt aag cct atc cct aac cct ctc ctc ggt ctc gat     1344
Gly Pro Phe Glu Gly Lys Pro Ile Pro Asn Pro Leu Leu Gly Leu Asp
        435                 440                 445

tct acg cgt acc ggt cat cat cac cat cac cat tga                     1380
Ser Thr Arg Thr Gly His His His His His His
    450                 455
```

<210> SEQ ID NO 24
<211> LENGTH: 459
<212> TYPE: PRT
<213> ORGANISM: Artificial sequence
<220> FEATURE:
<223> OTHER INFORMATION: Sequence of mutant H2-1

<400> SEQUENCE: 24

```
Pro Lys Tyr Val Lys Gln Asn Thr Leu Lys Leu Ala Thr Gly Thr Gly
```

-continued

```
1               5                   10                  15

Gly Ser Leu Val Pro Arg Gly Ser Gly Gly Gly Gly Ser Gly Asp Thr
            20                  25                  30

Arg Pro Arg Phe Leu Trp Gln His Lys Phe Glu Cys His Phe Phe Asn
        35                  40                  45

Gly Thr Glu Arg Val Arg Leu Leu Glu Arg Cys Ile Tyr Asn Gln Glu
    50                  55                  60

Glu Ser Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Gln Arg Arg Ala Ala Val Asp Thr Tyr Cys Arg His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Gln Arg Ser Gly Gly Gly Gly Ser Gly Gly Thr Ser Lys Glu Glu His
225                 230                 235                 240

Val Ile Ile Gln Ala Glu Phe Tyr Leu Asn Pro Asp Gln Ser Gly Glu
                245                 250                 255

Phe Met Phe Asp Phe Asp Gly Asp Glu Ile Phe His Val Asp Met Ala
            260                 265                 270

Lys Lys Glu Thr Val Trp Arg Leu Glu Glu Phe Gly Arg Phe Ala Ser
        275                 280                 285

Phe Glu Ala Gln Gly Ala Leu Ala Asn Ile Ala Val Asp Lys Ala Asn
    290                 295                 300

Leu Glu Ile Met Thr Lys Arg Ser Asn Tyr Thr Pro Ile Thr Asn Val
305                 310                 315                 320

Pro Pro Glu Val Thr Val Leu Thr Asn Ser Pro Val Glu Leu Arg Glu
                325                 330                 335

Pro Asn Val Leu Ile Cys Phe Ile Asp Lys Phe Thr Pro Pro Val Val
            340                 345                 350

Asn Val Thr Trp Leu Arg Asn Gly Lys Pro Val Thr Thr Gly Val Ser
        355                 360                 365

Glu Thr Val Phe Leu Pro Arg Glu Asp His Leu Phe Arg Lys Phe His
    370                 375                 380

Tyr Leu Pro Phe Leu Pro Ser Thr Glu Asp Val Tyr Asp Cys Arg Val
385                 390                 395                 400

Glu His Trp Gly Leu Asp Glu Pro Leu Leu Lys His Trp Glu Phe Asp
                405                 410                 415

Ala Pro Ser Pro Leu Pro Glu Thr Thr Glu Asn Leu Leu Glu Ser Arg
            420                 425                 430
```

-continued

```
Gly Pro Phe Glu Gly Lys Pro Ile Pro Asn Pro Leu Leu Gly Leu Asp
        435                 440                 445

Ser Thr Arg Thr Gly His His His His His His
    450                 455


<210> SEQ ID NO 25
<211> LENGTH: 1380
<212> TYPE: DNA
<213> ORGANISM: Artificial sequence
<220> FEATURE:
<223> OTHER INFORMATION: Sequence of mutant H2-2
<220> FEATURE:
<221> NAME/KEY: CDS
<222> LOCATION: (1)..(1377)

<400> SEQUENCE: 25

ccc aag tat gtt aag caa aac acc ctg aag ttg gca aca ggt acc ggt       48
Pro Lys Tyr Val Lys Gln Asn Thr Leu Lys Leu Ala Thr Gly Thr Gly
1               5                   10                  15

ggc tca cta gtg cca cgg ggc tct gga gga ggt ggg tcc ggg gac acc       96
Gly Ser Leu Val Pro Arg Gly Ser Gly Gly Gly Gly Ser Gly Asp Thr
            20                  25                  30

cga cca cgt ttc ttg tgg cag cat aag ttt gaa tgt cat ttc ttc aat      144
Arg Pro Arg Phe Leu Trp Gln His Lys Phe Glu Cys His Phe Phe Asn
        35                  40                  45

ggg acg gag cgg gtg cgg ttg ctg gaa aga tgc atc tat aac caa gag      192
Gly Thr Glu Arg Val Arg Leu Leu Glu Arg Cys Ile Tyr Asn Gln Glu
    50                  55                  60

gag tcc gtg cgc ttc gac agc gac gtg ggg gag tac cgg gcg gtg acg      240
Glu Ser Val Arg Phe Asp Ser Asp Val Gly Glu Tyr Arg Ala Val Thr
65                  70                  75                  80

gag ctg ggg cgg cct gat gcc gag tac tgg aac agc cag aag gac ctc      288
Glu Leu Gly Arg Pro Asp Ala Glu Tyr Trp Asn Ser Gln Lys Asp Leu
                85                  90                  95

ctg gag cag agg cgg gcc gcg gtg gac acc tac tgc aaa cac aac tac      336
Leu Glu Gln Arg Arg Ala Ala Val Asp Thr Tyr Cys Lys His Asn Tyr
            100                 105                 110

ggg gtt ggt gag agc ttc aca gtg cag cgg cga gtt gag cct aag gtg      384
Gly Val Gly Glu Ser Phe Thr Val Gln Arg Arg Val Glu Pro Lys Val
        115                 120                 125

act gtg tat cct tca aag acc cag ccc ctg cag cac cac aac ctc ctg      432
Thr Val Tyr Pro Ser Lys Thr Gln Pro Leu Gln His His Asn Leu Leu
    130                 135                 140

gtc tgc tct gtg agt ggt ttc tat cca ggc agc att gaa gtc agg tgg      480
Val Cys Ser Val Ser Gly Phe Tyr Pro Gly Ser Ile Glu Val Arg Trp
145                 150                 155                 160

ttc cgg aac ggc cag gaa gag aag gct ggg gtg gtg tcc aca ggc ctg      528
Phe Arg Asn Gly Gln Glu Glu Lys Ala Gly Val Val Ser Thr Gly Leu
                165                 170                 175

atc cag aat gga gat tgg acc ttc cag acc ctg gtg atg ctg gaa aca      576
Ile Gln Asn Gly Asp Trp Thr Phe Gln Thr Leu Val Met Leu Glu Thr
            180                 185                 190

gtt cct cgg agt gga gag gtt tac acc tgc caa gtg gag cac cca agt      624
Val Pro Arg Ser Gly Glu Val Tyr Thr Cys Gln Val Glu His Pro Ser
        195                 200                 205

gtg acg agc cct ctc aca gtg gaa tgg aga gca cgg tct gaa tct gca      672
Val Thr Ser Pro Leu Thr Val Glu Trp Arg Ala Arg Ser Glu Ser Ala
    210                 215                 220

cag aga tct gga ggt gga ggc tca gga ggt act agt aga gaa gaa cat      720
Gln Arg Ser Gly Gly Gly Gly Ser Gly Gly Thr Ser Arg Glu Glu His
225                 230                 235                 240
```

-continued gtg atc atc cag gcc gag ttc tat ctg aat cct gac caa tca ggc gag 768
Val Ile Ile Gln Ala Glu Phe Tyr Leu Asn Pro Asp Gln Ser Gly Glu
245 250 255 ttt atg ttt gac ttt gat ggt gat gag att ttc cat gtg gat atg gca 816
Phe Met Phe Asp Phe Asp Gly Asp Glu Ile Phe His Val Asp Met Ala
260 265 270 aag aag gag acg gtc tgg cgg ctt gaa gaa ttt gga cga ttt gcc agc 864
Lys Lys Glu Thr Val Trp Arg Leu Glu Glu Phe Gly Arg Phe Ala Ser
275 280 285 ttt gag gct caa ggt gca ttg gcc aac ata gct gtg gac aaa gcc aac 912
Phe Glu Ala Gln Gly Ala Leu Ala Asn Ile Ala Val Asp Lys Ala Asn
290 295 300 ctg gaa atc ttg aca aag cgc tcc aac tat act ccg atc acc aat gta 960
Leu Glu Ile Leu Thr Lys Arg Ser Asn Tyr Thr Pro Ile Thr Asn Val
305 310 315 320 cct cca gag gta act gtg ctc acg aac agc cct gtg gaa ctg aga gag 1008
Pro Pro Glu Val Thr Val Leu Thr Asn Ser Pro Val Glu Leu Arg Glu
325 330 335 ccc aac gtc ctc atc tgt ttc atc gac aag ttc acc cca cca gtg gtc 1056
Pro Asn Val Leu Ile Cys Phe Ile Asp Lys Phe Thr Pro Pro Val Val
340 345 350 aat gtc acg tgg ctt cga aat gga aaa cct gtc acc aca gga gtg tca 1104
Asn Val Thr Trp Leu Arg Asn Gly Lys Pro Val Thr Thr Gly Val Ser
355 360 365 gag aca gtc ttc ctg ccc agg gaa gac cac ctt ttc cgc aag ttc cac 1152
Glu Thr Val Phe Leu Pro Arg Glu Asp His Leu Phe Arg Lys Phe His
370 375 380 tat ctc ccc ttc ctg ccc tca act gag gac gtt tac gac tgc agg gtg 1200
Tyr Leu Pro Phe Leu Pro Ser Thr Glu Asp Val Tyr Asp Cys Arg Val
385 390 395 400 gag cac tgg ggc ttg gat gag cct ctt ctc aag cac tgg gag ttt gat 1248
Glu His Trp Gly Leu Asp Glu Pro Leu Leu Lys His Trp Glu Phe Asp
405 410 415 gca cca agc cct ctc cca gag act aca gag aac tta ctc gag tct aga 1296
Ala Pro Ser Pro Leu Pro Glu Thr Thr Glu Asn Leu Leu Glu Ser Arg
420 425 430 ggg ccc ttc gaa ggt aag cct atc cct aac cct ctc ctc ggt ctc gat 1344
Gly Pro Phe Glu Gly Lys Pro Ile Pro Asn Pro Leu Leu Gly Leu Asp
435 440 445 tct acg cgt acc ggt cat cat cac cat cac cat tga 1380
Ser Thr Arg Thr Gly His His His His His His
450 455

<210> SEQ ID NO 26
<211> LENGTH: 459
<212> TYPE: PRT
<213> ORGANISM: Artificial sequence
<220> FEATURE:
<223> OTHER INFORMATION: Sequence of mutant H2-2

<400> SEQUENCE: 26

Pro Lys Tyr Val Lys Gln Asn Thr Leu Lys Leu Ala Thr Gly Thr Gly
1 5 10 15

Gly Ser Leu Val Pro Arg Gly Ser Gly Gly Gly Gly Ser Gly Asp Thr
20 25 30

Arg Pro Arg Phe Leu Trp Gln His Lys Phe Glu Cys His Phe Phe Asn
35 40 45

Gly Thr Glu Arg Val Arg Leu Leu Glu Arg Cys Ile Tyr Asn Gln Glu
50 55 60

-continued

```
Glu Ser Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Gln Arg Arg Ala Ala Val Asp Thr Tyr Cys Lys His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Gln Arg Ser Gly Gly Gly Gly Ser Gly Gly Thr Ser Arg Glu Glu His
225                 230                 235                 240

Val Ile Ile Gln Ala Glu Phe Tyr Leu Asn Pro Asp Gln Ser Gly Glu
                245                 250                 255

Phe Met Phe Asp Phe Asp Gly Asp Glu Ile Phe His Val Asp Met Ala
            260                 265                 270

Lys Lys Glu Thr Val Trp Arg Leu Glu Glu Phe Gly Arg Phe Ala Ser
        275                 280                 285

Phe Glu Ala Gln Gly Ala Leu Ala Asn Ile Ala Val Asp Lys Ala Asn
    290                 295                 300

Leu Glu Ile Leu Thr Lys Arg Ser Asn Tyr Thr Pro Ile Thr Asn Val
305                 310                 315                 320

Pro Pro Glu Val Thr Val Leu Thr Asn Ser Pro Val Glu Leu Arg Glu
                325                 330                 335

Pro Asn Val Leu Ile Cys Phe Ile Asp Lys Phe Thr Pro Pro Val Val
            340                 345                 350

Asn Val Thr Trp Leu Arg Asn Gly Lys Pro Val Thr Thr Gly Val Ser
        355                 360                 365

Glu Thr Val Phe Leu Pro Arg Glu Asp His Leu Phe Arg Lys Phe His
    370                 375                 380

Tyr Leu Pro Phe Leu Pro Ser Thr Glu Asp Val Tyr Asp Cys Arg Val
385                 390                 395                 400

Glu His Trp Gly Leu Asp Glu Pro Leu Leu Lys His Trp Glu Phe Asp
                405                 410                 415

Ala Pro Ser Pro Leu Pro Glu Thr Thr Glu Asn Leu Leu Glu Ser Arg
            420                 425                 430

Gly Pro Phe Glu Gly Lys Pro Ile Pro Asn Pro Leu Leu Gly Leu Asp
        435                 440                 445

Ser Thr Arg Thr Gly His His His His His His
    450                 455

<210> SEQ ID NO 27
<211> LENGTH: 1380
<212> TYPE: DNA
```

-continued

<213> ORGANISM: Artificial sequence
<220> FEATURE:
<223> OTHER INFORMATION: Sequence of mutant H2-3
<220> FEATURE:
<221> NAME/KEY: CDS
<222> LOCATION: (1)..(1377)
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (1356)..(1356)
<223> OTHER INFORMATION: n is a, c, g, or t

<400> SEQUENCE: 27 ccc aag tat gtt aag caa aac acc ctg aag ttg gca aca ggt acc ggt 48
Pro Lys Tyr Val Lys Gln Asn Thr Leu Lys Leu Ala Thr Gly Thr Gly
1 5 10 15 ggc tca cta gtg cca cgg ggc tct gga gga ggt ggg tcc ggg gac acc 96
Gly Ser Leu Val Pro Arg Gly Ser Gly Gly Gly Gly Ser Gly Asp Thr
20 25 30 cga cca cgt ttc ttg tgg cag cat aag ttt gaa tgt cat ttc ttc aat 144
Arg Pro Arg Phe Leu Trp Gln His Lys Phe Glu Cys His Phe Phe Asn
35 40 45 ggg acg gag cgg gtg cgg ttg ctg gaa aga tgc atc tat aac caa aag 192
Gly Thr Glu Arg Val Arg Leu Leu Glu Arg Cys Ile Tyr Asn Gln Lys
50 55 60 gag tcc gtg cgc ttc gac agc gac gtg ggg gag tac cgg gcg gtg acn 240
Glu Ser Val Arg Phe Asp Ser Asp Val Gly Glu Tyr Arg Ala Val Thr
65 70 75 80 gag ctg ggg cgg cct gat gcc gag tac tgg aac agc cag aag gac ctc 288
Glu Leu Gly Arg Pro Asp Ala Glu Tyr Trp Asn Ser Gln Lys Asp Leu
85 90 95 ctg gag caa agg cgg gcc gcc gtg gac acc tac tgc aga cac aac tac 336
Leu Glu Gln Arg Arg Ala Ala Val Asp Thr Tyr Cys Arg His Asn Tyr
100 105 110 ggg gtt ggt gag agc ttc aca gtg cag cgg cga gtt gag cct aag gtg 384
Gly Val Gly Glu Ser Phe Thr Val Gln Arg Arg Val Glu Pro Lys Val
115 120 125 act gtg tat cct tca aag acc cag ccc ctg cag cac cac aac ctc ctg 432
Thr Val Tyr Pro Ser Lys Thr Gln Pro Leu Gln His His Asn Leu Leu
130 135 140 gtc tgc tct gtg agt ggt ttc tat cca ggc agc att gaa gtc agg tgg 480
Val Cys Ser Val Ser Gly Phe Tyr Pro Gly Ser Ile Glu Val Arg Trp
145 150 155 160 ttc cgg aac ggc cag gaa gag aag gct ggg gtg gtg tcc aca ggc ctg 528
Phe Arg Asn Gly Gln Glu Glu Lys Ala Gly Val Val Ser Thr Gly Leu
165 170 175 atc cag aat gga gat tgg acc ttc cag acc ctg gtg atg ctg gaa aca 576
Ile Gln Asn Gly Asp Trp Thr Phe Gln Thr Leu Val Met Leu Glu Thr
180 185 190 gtt cct cgg agt gga gag gtt tac acc tgc caa gtg gag cac cca agt 624
Val Pro Arg Ser Gly Glu Val Tyr Thr Cys Gln Val Glu His Pro Ser
195 200 205 gtg acg agc cct ctc aca gtg gaa tgg aga gca cgg tct gaa tct gca 672
Val Thr Ser Pro Leu Thr Val Glu Trp Arg Ala Arg Ser Glu Ser Ala
210 215 220 cag aga tct gga ggt gga ggc tca gga ggt act agt aaa gaa gaa cat 720
Gln Arg Ser Gly Gly Gly Gly Ser Gly Gly Thr Ser Lys Glu Glu His
225 230 235 240 gtg atc atc cag gcc gag ttc tat ctg aat cct gac caa tca ggc gag 768
Val Ile Ile Gln Ala Glu Phe Tyr Leu Asn Pro Asp Gln Ser Gly Glu -continued

```
                245                 250                 255

ttt atg ttt gac ttt gat ggt gat gag att ttc cat gtg gat atg gca      816
Phe Met Phe Asp Phe Asp Gly Asp Glu Ile Phe His Val Asp Met Ala
            260                 265                 270

aag aag gag acg gtc tgg cgg ctt gaa gaa ttt gga cga ttt gcc agc      864
Lys Lys Glu Thr Val Trp Arg Leu Glu Glu Phe Gly Arg Phe Ala Ser
        275                 280                 285

ttt gag gct caa ggt gca ttg gcc aac ata gct gtg gac aaa gcc aac      912
Phe Glu Ala Gln Gly Ala Leu Ala Asn Ile Ala Val Asp Lys Ala Asn
    290                 295                 300

ctg gaa atc atg aca aag cgc tcc aac tat act ccg atc acc aat gta      960
Leu Glu Ile Met Thr Lys Arg Ser Asn Tyr Thr Pro Ile Thr Asn Val
305                 310                 315                 320

cct cca gag gta act gtg ctc acg aac agc cct gtg gaa ctg aga gag     1008
Pro Pro Glu Val Thr Val Leu Thr Asn Ser Pro Val Glu Leu Arg Glu
                325                 330                 335

ccc aac gtc ctc atc tgt ttc atc gac aag ttc acc cca cca gtg gtc     1056
Pro Asn Val Leu Ile Cys Phe Ile Asp Lys Phe Thr Pro Pro Val Val
            340                 345                 350

aat gtc acg tgg ctt cga aat gga aaa cct gtc acc aca gga gtg tca     1104
Asn Val Thr Trp Leu Arg Asn Gly Lys Pro Val Thr Thr Gly Val Ser
        355                 360                 365

gag aca gtc ttc ctg ccc agg gaa gac cac ctt ttc cgc aag ttc cac     1152
Glu Thr Val Phe Leu Pro Arg Glu Asp His Leu Phe Arg Lys Phe His
    370                 375                 380

tat ctc ccc ttc ctg ccc tca act gag gac gtt tac gac tgc agg gtg     1200
Tyr Leu Pro Phe Leu Pro Ser Thr Glu Asp Val Tyr Asp Cys Arg Val
385                 390                 395                 400

gag cac tgg ggc ttg gat gag cct ctt ctc aag cac tgg gag ttt gat     1248
Glu His Trp Gly Leu Asp Glu Pro Leu Leu Lys His Trp Glu Phe Asp
                405                 410                 415

gca cca agc cct ctc cca gag act aca gag aac tga ctc gag tct aga     1296
Ala Pro Ser Pro Leu Pro Glu Thr Thr Glu Asn     Leu Glu Ser Arg
            420                 425                 430

ggg ccc ttc gaa ggt aag cct atc cgt agc cct ctc ctc ggt ctc gat     1344
Gly Pro Phe Glu Gly Lys Pro Ile Arg Ser Pro Leu Leu Gly Leu Asp
            435                 440                 445

tct acg cgt acn ggt cat cat cac cat cac cat tga                     1380
Ser Thr Arg Thr Gly His His His His His His
        450                 455


<210> SEQ ID NO 28
<211> LENGTH: 427
<212> TYPE: PRT
<213> ORGANISM: Artificial sequence
<220> FEATURE:
<223> OTHER INFORMATION: Sequence of mutant H2-3

<400> SEQUENCE: 28

Pro Lys Tyr Val Lys Gln Asn Thr Leu Lys Leu Ala Thr Gly Thr Gly
1               5                   10                  15

Gly Ser Leu Val Pro Arg Gly Ser Gly Gly Gly Gly Ser Gly Asp Thr
            20                  25                  30

Arg Pro Arg Phe Leu Trp Gln His Lys Phe Glu Cys His Phe Phe Asn
        35                  40                  45

Gly Thr Glu Arg Val Arg Leu Leu Glu Arg Cys Ile Tyr Asn Gln Lys
    50                  55                  60

Glu Ser Val Arg Phe Asp Ser Asp Val Gly Glu Tyr Arg Ala Val Thr
65                  70                  75                  80
```

-continued

```
Glu Leu Gly Arg Pro Asp Ala Glu Tyr Trp Asn Ser Gln Lys Asp Leu
                85                  90                  95

Leu Glu Gln Arg Arg Ala Ala Val Asp Thr Tyr Cys Arg His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Gln Arg Ser Gly Gly Gly Gly Ser Gly Gly Thr Ser Lys Glu Glu His
225                 230                 235                 240

Val Ile Ile Gln Ala Glu Phe Tyr Leu Asn Pro Asp Gln Ser Gly Glu
                245                 250                 255

Phe Met Phe Asp Phe Asp Gly Asp Glu Ile Phe His Val Asp Met Ala
            260                 265                 270

Lys Lys Glu Thr Val Trp Arg Leu Glu Glu Phe Gly Arg Phe Ala Ser
        275                 280                 285

Phe Glu Ala Gln Gly Ala Leu Ala Asn Ile Ala Val Asp Lys Ala Asn
    290                 295                 300

Leu Glu Ile Met Thr Lys Arg Ser Asn Tyr Thr Pro Ile Thr Asn Val
305                 310                 315                 320

Pro Pro Glu Val Thr Val Leu Thr Asn Ser Pro Val Glu Leu Arg Glu
                325                 330                 335

Pro Asn Val Leu Ile Cys Phe Ile Asp Lys Phe Thr Pro Pro Val Val
            340                 345                 350

Asn Val Thr Trp Leu Arg Asn Gly Lys Pro Val Thr Thr Gly Val Ser
        355                 360                 365

Glu Thr Val Phe Leu Pro Arg Glu Asp His Leu Phe Arg Lys Phe His
    370                 375                 380

Tyr Leu Pro Phe Leu Pro Ser Thr Glu Asp Val Tyr Asp Cys Arg Val
385                 390                 395                 400

Glu His Trp Gly Leu Asp Glu Pro Leu Leu Lys His Trp Glu Phe Asp
                405                 410                 415

Ala Pro Ser Pro Leu Pro Glu Thr Thr Glu Asn
            420                 425
```

<210> SEQ ID NO 29
<211> LENGTH: 31
<212> TYPE: PRT
<213> ORGANISM: Artificial sequence
<220> FEATURE:
<223> OTHER INFORMATION: Sequence of mutant H2-3

<400> SEQUENCE: 29

```
Leu Glu Ser Arg Gly Pro Phe Glu Gly Lys Pro Ile Arg Ser Pro Leu
1               5                   10                  15
```

-continued

Leu Gly Leu Asp Ser Thr Arg Thr Gly His His His His His His
20 25 30

<210> SEQ ID NO 30
<211> LENGTH: 1380
<212> TYPE: DNA
<213> ORGANISM: Artificial sequence
<220> FEATURE:
<223> OTHER INFORMATION: Sequence of mutant H3-3
<220> FEATURE:
<221> NAME/KEY: CDS
<222> LOCATION: (1)..(1377)

<400> SEQUENCE: 30 tcc aag tat gtt aag caa aac acc ctg aag ttg gca aca ggt acc ggt 48
Ser Lys Tyr Val Lys Gln Asn Thr Leu Lys Leu Ala Thr Gly Thr Gly
1 5 10 15 ggc tct cta gtg cca cgg ggc tct gga gga ggt ggg tcc ggg gac acc 96
Gly Ser Leu Val Pro Arg Gly Ser Gly Gly Gly Gly Ser Gly Asp Thr
20 25 30 cga cca cgt ttc ttg tgg cag cat aag ttt gaa tgt cat ttc ttc aat 144
Arg Pro Arg Phe Leu Trp Gln His Lys Phe Glu Cys His Phe Phe Asn
35 40 45 ggg acg gag cgg gtg cgg ttg ctg gaa aga tgc atc tat aac caa gag 192
Gly Thr Glu Arg Val Arg Leu Leu Glu Arg Cys Ile Tyr Asn Gln Glu
50 55 60 gag tcc gtg cgc ttc gac agc gac gtg ggg gag tac cgg gcg gtg acg 240
Glu Ser Val Arg Phe Asp Ser Asp Val Gly Glu Tyr Arg Ala Val Thr
65 70 75 80 gag ctg ggg cgg cct gat gcc gag tac tgg aac agc cag aag gac ctc 288
Glu Leu Gly Arg Pro Asp Ala Glu Tyr Trp Asn Ser Gln Lys Asp Leu
85 90 95 ctg gag cag agg cgg gcc gcg gtg gac acc tac tgc aga cac aac tac 336
Leu Glu Gln Arg Arg Ala Ala Val Asp Thr Tyr Cys Arg His Asn Tyr
100 105 110 ggg gtt ggt gag agc ttc aca gtg cag cgg cga gtt gag cct aag gtg 384
Gly Val Gly Glu Ser Phe Thr Val Gln Arg Arg Val Glu Pro Lys Val
115 120 125 act gtg tat cct tca aag acc cag ccc ctg cag cac cac aac ctc ctg 432
Thr Val Tyr Pro Ser Lys Thr Gln Pro Leu Gln His His Asn Leu Leu
130 135 140 gtc tgc tct gtg agt ggt ttc tat cca ggc agc att gaa gtc agg tgg 480
Val Cys Ser Val Ser Gly Phe Tyr Pro Gly Ser Ile Glu Val Arg Trp
145 150 155 160 ttc cgg aac ggc cag gaa gag aag gct ggg gtg gtg tcc aca ggc ctg 528
Phe Arg Asn Gly Gln Glu Glu Lys Ala Gly Val Val Ser Thr Gly Leu
165 170 175 atc cag aat gga gat tgg acc ttc cag acc ctg gtg atg ctg gaa aca 576
Ile Gln Asn Gly Asp Trp Thr Phe Gln Thr Leu Val Met Leu Glu Thr
180 185 190 gtt cct cgg agt gga gag gtt tac acc tgc caa gtg gag cac cca agt 624
Val Pro Arg Ser Gly Glu Val Tyr Thr Cys Gln Val Glu His Pro Ser
195 200 205 gtg acg agc cct ctc aca gtg gaa tgg agt gca cgg tct gaa tct gca 672
Val Thr Ser Pro Leu Thr Val Glu Trp Ser Ala Arg Ser Glu Ser Ala
210 215 220 cag aga tct gga ggt gga ggc tca gga ggt act agt aaa gaa gaa cat 720
Gln Arg Ser Gly Gly Gly Gly Ser Gly Gly Thr Ser Lys Glu Glu His
225 230 235 240 gtg atc atc cag gcc gag ttc tat ctg aat cct gac caa tca ggc gag 768
Val Ile Ile Gln Ala Glu Phe Tyr Leu Asn Pro Asp Gln Ser Gly Glu
245 250 255

-continued

```
ttt atg ttt gac ttt gat agt gat gag act ttc cat gtg gat atg gca      816
Phe Met Phe Asp Phe Asp Ser Asp Glu Thr Phe His Val Asp Met Ala
            260                 265                 270

aag aag gag acg gtc tgg cgg ctt gaa gaa ttt gga cga ttt gcc agc      864
Lys Lys Glu Thr Val Trp Arg Leu Glu Glu Phe Gly Arg Phe Ala Ser
        275                 280                 285

ttt gag gct caa ggt gca ttg gcc aac ata gct gtg gac aaa gcc aac      912
Phe Glu Ala Gln Gly Ala Leu Ala Asn Ile Ala Val Asp Lys Ala Asn
    290                 295                 300

ctg gaa atc atg aca aag cgc tcc aac tat act ccg atc acc aat gta      960
Leu Glu Ile Met Thr Lys Arg Ser Asn Tyr Thr Pro Ile Thr Asn Val
305                 310                 315                 320

cct cca gag gta act gtg ctc acg aac agc cct gtg gaa ctg aga gag     1008
Pro Pro Glu Val Thr Val Leu Thr Asn Ser Pro Val Glu Leu Arg Glu
                325                 330                 335

ccc aac gtc ctc atc tgt ttc atc gac aag ttc acc cca cca gtg gtc     1056
Pro Asn Val Leu Ile Cys Phe Ile Asp Lys Phe Thr Pro Pro Val Val
            340                 345                 350

aat gtc acg tgg ctt cga aat gga aaa cct gtc acc aca gga gtg tca     1104
Asn Val Thr Trp Leu Arg Asn Gly Lys Pro Val Thr Thr Gly Val Ser
        355                 360                 365

gag aca gtc ttc ctg ccc agg gaa gac cac ctt ttc cgc aag ttc cac     1152
Glu Thr Val Phe Leu Pro Arg Glu Asp His Leu Phe Arg Lys Phe His
    370                 375                 380

tat ctc ccc ttc ctg ccc tca act gag gac gtt tac gac tgc agg gtg     1200
Tyr Leu Pro Phe Leu Pro Ser Thr Glu Asp Val Tyr Asp Cys Arg Val
385                 390                 395                 400

gag cac tgg ggc ttg gat gag cct ctt ctc aag cac tgg gag ttt gat     1248
Glu His Trp Gly Leu Asp Glu Pro Leu Leu Lys His Trp Glu Phe Asp
                405                 410                 415

gca cca agc cct ctc cca gag act aca gag aac tta ctc gag tct aga     1296
Ala Pro Ser Pro Leu Pro Glu Thr Thr Glu Asn Leu Leu Glu Ser Arg
            420                 425                 430

ggg ccc ttc gaa ggt aag cct atc cct aac cct ctc ctc ggt ctc gat     1344
Gly Pro Phe Glu Gly Lys Pro Ile Pro Asn Pro Leu Leu Gly Leu Asp
        435                 440                 445

tct acg cgt acc ggt cat cat cac cat cac cat tga                     1380
Ser Thr Arg Thr Gly His His His His His His
    450                 455


<210> SEQ ID NO 31
<211> LENGTH: 459
<212> TYPE: PRT
<213> ORGANISM: Artificial sequence
<220> FEATURE:
<223> OTHER INFORMATION: Sequence of mutant H3-3

<400> SEQUENCE: 31

Ser Lys Tyr Val Lys Gln Asn Thr Leu Lys Leu Ala Thr Gly Thr Gly
1               5                   10                  15

Gly Ser Leu Val Pro Arg Gly Ser Gly Gly Gly Gly Ser Gly Asp Thr
            20                  25                  30

Arg Pro Arg Phe Leu Trp Gln His Lys Phe Glu Cys His Phe Phe Asn
        35                  40                  45

Gly Thr Glu Arg Val Arg Leu Leu Glu Arg Cys Ile Tyr Asn Gln Glu
    50                  55                  60

Glu Ser Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
```

-continued

```
                85                  90                  95

Leu Glu Gln Arg Arg Ala Ala Val Asp Thr Tyr Cys Arg His Asn Tyr
            100                 105                 110

Gly Val Gly Glu Ser Phe Thr Val Gln Arg Arg Val Glu Pro Lys Val
        115                 120                 125

Thr Val Tyr Pro Ser Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Ser Ala Arg Ser Glu Ser Ala
    210                 215                 220

Gln Arg Ser Gly Gly Gly Gly Ser Gly Gly Thr Ser Lys Glu Glu His
225                 230                 235                 240

Val Ile Ile Gln Ala Glu Phe Tyr Leu Asn Pro Asp Gln Ser Gly Glu
                245                 250                 255

Phe Met Phe Asp Phe Asp Ser Asp Glu Thr Phe His Val Asp Met Ala
            260                 265                 270

Lys Lys Glu Thr Val Trp Arg Leu Glu Glu Phe Gly Arg Phe Ala Ser
        275                 280                 285

Phe Glu Ala Gln Gly Ala Leu Ala Asn Ile Ala Val Asp Lys Ala Asn
    290                 295                 300

Leu Glu Ile Met Thr Lys Arg Ser Asn Tyr Thr Pro Ile Thr Asn Val
305                 310                 315                 320

Pro Pro Glu Val Thr Val Leu Thr Asn Ser Pro Val Glu Leu Arg Glu
                325                 330                 335

Pro Asn Val Leu Ile Cys Phe Ile Asp Lys Phe Thr Pro Pro Val Val
            340                 345                 350

Asn Val Thr Trp Leu Arg Asn Gly Lys Pro Val Thr Thr Gly Val Ser
        355                 360                 365

Glu Thr Val Phe Leu Pro Arg Glu Asp His Leu Phe Arg Lys Phe His
    370                 375                 380

Tyr Leu Pro Phe Leu Pro Ser Thr Glu Asp Val Tyr Asp Cys Arg Val
385                 390                 395                 400

Glu His Trp Gly Leu Asp Glu Pro Leu Leu Lys His Trp Glu Phe Asp
                405                 410                 415

Ala Pro Ser Pro Leu Pro Glu Thr Thr Glu Asn Leu Leu Glu Ser Arg
            420                 425                 430

Gly Pro Phe Glu Gly Lys Pro Ile Pro Asn Pro Leu Leu Gly Leu Asp
        435                 440                 445

Ser Thr Arg Thr Gly His His His His His His
    450                 455
```

<210> SEQ ID NO 32
<211> LENGTH: 1314
<212> TYPE: DNA
<213> ORGANISM: Artificial sequence
<220> FEATURE:
<223> OTHER INFORMATION: Sequence of mutant DO-1
<220> FEATURE:

```
<221> NAME/KEY: CDS
<222> LOCATION: (1)..(1311)

<400> SEQUENCE: 32

agg aaa gaa gaa cat gtg atc acc cag gcc gag ttc tat ctg aat cct       48
Arg Lys Glu Glu His Val Ile Thr Gln Ala Glu Phe Tyr Leu Asn Pro
1               5                   10                  15

gac caa tca ggc gag ttt atg ttt gac ttt gat ggt gat gag att ttc       96
Asp Gln Ser Gly Glu Phe Met Phe Asp Phe Asp Gly Asp Glu Ile Phe
            20                  25                  30

cat gtg gat atg gca aag aag gag acg gtc tgg cgg ctt gaa gaa ttt      144
His Val Asp Met Ala Lys Lys Glu Thr Val Trp Arg Leu Glu Glu Phe
        35                  40                  45

gga cga ttt gcc agc ttt gag gct caa ggt gca ttg gcc aac ata gct      192
Gly Arg Phe Ala Ser Phe Glu Ala Gln Gly Ala Leu Ala Asn Ile Ala
    50                  55                  60

gtg gac aaa gcc aac ctg gaa atc atg aca aag cgc tcc aac tat act      240
Val Asp Lys Ala Asn Leu Glu Ile Met Thr Lys Arg Ser Asn Tyr Thr
65                  70                  75                  80

ccg atc acc aat gta cct cca gag gta act gtg ctc acg aac agc cct      288
Pro Ile Thr Asn Val Pro Pro Glu Val Thr Val Leu Thr Asn Ser Pro
                85                  90                  95

gtg gaa ctg aga gag ccc aac gtc ctc atc tgt tac atc gac aag ttc      336
Val Glu Leu Arg Glu Pro Asn Val Leu Ile Cys Tyr Ile Asp Lys Phe
            100                 105                 110

acc cca cca gtg gtc aat gtc acg tgg ctt cga aat gga aaa cct gtc      384
Thr Pro Pro Val Val Asn Val Thr Trp Leu Arg Asn Gly Lys Pro Val
        115                 120                 125

acc aca gga gtg tca gag aca gtc ttc ctg ccc agg gaa gac cac ctt      432
Thr Thr Gly Val Ser Glu Thr Val Phe Leu Pro Arg Glu Asp His Leu
    130                 135                 140

ttc cgc aag ttc cac tat ctc ccc ttc ctg ccc tca act gag gac gtt      480
Phe Arg Lys Phe His Tyr Leu Pro Phe Leu Pro Ser Thr Glu Asp Val
145                 150                 155                 160

tac gac tgc agg gtg gag cac tgg ggc ttg gat gag cct ctt ctc aag      528
Tyr Asp Cys Arg Val Glu His Trp Gly Leu Asp Glu Pro Leu Leu Lys
                165                 170                 175

cac tgg gag ttt aat gca cca agc cct ctc cca gag act aca gag aac      576
His Trp Glu Phe Asn Ala Pro Ser Pro Leu Pro Glu Thr Thr Glu Asn
            180                 185                 190

tta gga ggc ggc ggc tca ggt ggc ggc cgc tct ggc gga ggt gga tcc      624
Leu Gly Gly Gly Gly Ser Gly Gly Gly Arg Ser Gly Gly Gly Gly Ser
        195                 200                 205

ggg gac acc cga cca cgt ttc ttg tgg cag cat aag ttt gaa tgt cat      672
Gly Asp Thr Arg Pro Arg Phe Leu Trp Gln His Lys Phe Glu Cys His
    210                 215                 220

ttc ttc aat ggg acg gag cgg gtg cgg ttg ctg gaa aga tgc atc tat      720
Phe Phe Asn Gly Thr Glu Arg Val Arg Leu Leu Glu Arg Cys Ile Tyr
225                 230                 235                 240

aac caa gag gag tcc gtg cgc ttc gac agc gac gtg ggg gag tac cgg      768
Asn Gln Glu Glu Ser Val Arg Phe Asp Ser Asp Val Gly Glu Tyr Arg
                245                 250                 255

gcg gtg acg gag ctg ggg cgg cct gct gcc gag tac tgg aac agc cag      816
Ala Val Thr Glu Leu Gly Arg Pro Ala Ala Glu Tyr Trp Asn Ser Gln
            260                 265                 270

aag gac ctc ctg gag cag agg cgg gcc gcg gcg gac acc tac tgc aga      864
Lys Asp Leu Leu Glu Gln Arg Arg Ala Ala Ala Asp Thr Tyr Cys Arg
        275                 280                 285

cac aac tac ggg gtt ggt gag agc ttc aca gtg cgg cgg cga gtt gag      912
His Asn Tyr Gly Val Gly Glu Ser Phe Thr Val Arg Arg Arg Val Glu
```

-continued

```
    290                 295                 300

cct aag gtg act gtg tat cct tca aag acc cag ccc ctg cag cac cac      960
Pro Lys Val Thr Val Tyr Pro Ser Lys Thr Gln Pro Leu Gln His His
305                 310                 315                 320

aac ctc ctg gtc tgc tct gtg agt ggt ttc tat cca ggc agc att gaa     1008
Asn Leu Leu Val Cys Ser Val Ser Gly Phe Tyr Pro Gly Ser Ile Glu
                325                 330                 335

gtc agg tgg ttc cgg aac ggc cag gaa gag aag gct ggg gtg gtg tcc     1056
Val Arg Trp Phe Arg Asn Gly Gln Glu Glu Lys Ala Gly Val Val Ser
            340                 345                 350

aca ggc ctg atc cag aat gga gat tgg acc ttc cag acc ctg gtg atg     1104
Thr Gly Leu Ile Gln Asn Gly Asp Trp Thr Phe Gln Thr Leu Val Met
        355                 360                 365

ctg gaa aca gtt cct cgg agt gga gag gtt tac acc tgc caa gtg gag     1152
Leu Glu Thr Val Pro Arg Ser Gly Glu Val Tyr Thr Cys Gln Val Glu
    370                 375                 380

cac cca agt gtg acg agc cct ctc aca gtg gaa tgg aga gca cgg tct     1200
His Pro Ser Val Thr Ser Pro Leu Thr Val Glu Trp Arg Ala Arg Ser
385                 390                 395                 400

gaa tct gca cag agc aag ctc gag tct aga ggg ccc ttc gaa ggt aag     1248
Glu Ser Ala Gln Ser Lys Leu Glu Ser Arg Gly Pro Phe Glu Gly Lys
                405                 410                 415

cct atc cct aac cct ctc ctc ggt ctc gat tct acg cgt acc ggt cat     1296
Pro Ile Pro Asn Pro Leu Leu Gly Leu Asp Ser Thr Arg Thr Gly His
            420                 425                 430

cat cac cat cac cat tga                                             1314
His His His His His
        435


<210> SEQ ID NO 33
<211> LENGTH: 437
<212> TYPE: PRT
<213> ORGANISM: Artificial sequence
<220> FEATURE:
<223> OTHER INFORMATION: Sequence of mutant DO-1

<400> SEQUENCE: 33

Arg Lys Glu Glu His Val Ile Thr Gln Ala Glu Phe Tyr Leu Asn Pro
1               5                   10                  15

Asp Gln Ser Gly Glu Phe Met Phe Asp Phe Asp Gly Asp Glu Ile Phe
            20                  25                  30

His Val Asp Met Ala Lys Lys Glu Thr Val Trp Arg Leu Glu Glu Phe
        35                  40                  45

Gly Arg Phe Ala Ser Phe Glu Ala Gln Gly Ala Leu Ala Asn Ile Ala
    50                  55                  60

Val Asp Lys Ala Asn Leu Glu Ile Met Thr Lys Arg Ser Asn Tyr Thr
65                  70                  75                  80

Pro Ile Thr Asn Val Pro Pro Glu Val Thr Val Leu Thr Asn Ser Pro
                85                  90                  95

Val Glu Leu Arg Glu Pro Asn Val Leu Ile Cys Tyr Ile Asp Lys Phe
            100                 105                 110

Thr Pro Pro Val Val Asn Val Thr Trp Leu Arg Asn Gly Lys Pro Val
        115                 120                 125

Thr Thr Gly Val Ser Glu Thr Val Phe Leu Pro Arg Glu Asp His Leu
    130                 135                 140

Phe Arg Lys Phe His Tyr Leu Pro Phe Leu Pro Ser Thr Glu Asp Val
145                 150                 155                 160

Tyr Asp Cys Arg Val Glu His Trp Gly Leu Asp Glu Pro Leu Leu Lys
```

-continued

```
                165                 170                 175

His Trp Glu Phe Asn Ala Pro Ser Pro Leu Pro Glu Thr Thr Glu Asn
            180                 185                 190

Leu Gly Gly Gly Gly Ser Gly Gly Gly Arg Ser Gly Gly Gly Gly Ser
        195                 200                 205

Gly Asp Thr Arg Pro Arg Phe Leu Trp Gln His Lys Phe Glu Cys His
    210                 215                 220

Phe Phe Asn Gly Thr Glu Arg Val Arg Leu Leu Glu Arg Cys Ile Tyr
225                 230                 235                 240

Asn Gln Glu Glu Ser Val Arg Phe Asp Ser Asp Val Gly Glu Tyr Arg
                245                 250                 255

Ala Val Thr Glu Leu Gly Arg Pro Ala Ala Glu Tyr Trp Asn Ser Gln
            260                 265                 270

Lys Asp Leu Leu Glu Gln Arg Arg Ala Ala Ala Asp Thr Tyr Cys Arg
        275                 280                 285

His Asn Tyr Gly Val Gly Glu Ser Phe Thr Val Arg Arg Arg Val Glu
    290                 295                 300

Pro Lys Val Thr Val Tyr Pro Ser Lys Thr Gln Pro Leu Gln His His
305                 310                 315                 320

Asn Leu Leu Val Cys Ser Val Ser Gly Phe Tyr Pro Gly Ser Ile Glu
                325                 330                 335

Val Arg Trp Phe Arg Asn Gly Gln Glu Glu Lys Ala Gly Val Val Ser
            340                 345                 350

Thr Gly Leu Ile Gln Asn Gly Asp Trp Thr Phe Gln Thr Leu Val Met
        355                 360                 365

Leu Glu Thr Val Pro Arg Ser Gly Glu Val Tyr Thr Cys Gln Val Glu
    370                 375                 380

His Pro Ser Val Thr Ser Pro Leu Thr Val Glu Trp Arg Ala Arg Ser
385                 390                 395                 400

Glu Ser Ala Gln Ser Lys Leu Glu Ser Arg Gly Pro Phe Glu Gly Lys
                405                 410                 415

Pro Ile Pro Asn Pro Leu Leu Gly Leu Asp Ser Thr Arg Thr Gly His
            420                 425                 430

His His His His His
        435


<210> SEQ ID NO 34
<211> LENGTH: 1314
<212> TYPE: DNA
<213> ORGANISM: Artificial sequence
<220> FEATURE:
<223> OTHER INFORMATION: Sequence of mutant DWP-5
<220> FEATURE:
<221> NAME/KEY: CDS
<222> LOCATION: (1)..(1311)

<400> SEQUENCE: 34

agg aaa gaa gaa cat gtg atc atc cag gcc gag ttc tat ctg aat cct       48
Arg Lys Glu Glu His Val Ile Ile Gln Ala Glu Phe Tyr Leu Asn Pro
1               5                   10                  15

gac caa tca ggc gag ttt atg ttt gac ttt gat ggt gat gag att ttc       96
Asp Gln Ser Gly Glu Phe Met Phe Asp Phe Asp Gly Asp Glu Ile Phe
            20                  25                  30

cat gtg gat atg gca aag aag gag acg gtc tgg cgg ctt gaa gaa ttt      144
His Val Asp Met Ala Lys Lys Glu Thr Val Trp Arg Leu Glu Glu Phe
        35                  40                  45

gga cga ttt gcc agc ttt gag gct caa ggt gca ttg gcc aac ata gct      192
```

-continued

```
Gly Arg Phe Ala Ser Phe Glu Ala Gln Gly Ala Leu Ala Asn Ile Ala
    50                  55                  60

gtg gac aaa gcc aac ctg gaa atc atg aca aag cgc tcc aac tat act      240
Val Asp Lys Ala Asn Leu Glu Ile Met Thr Lys Arg Ser Asn Tyr Thr
65                  70                  75                  80

ccg atc acc aat gta cct cca gag gta act gtg ctc acg aac agc cct      288
Pro Ile Thr Asn Val Pro Pro Glu Val Thr Val Leu Thr Asn Ser Pro
                85                  90                  95

gtg gaa ctg aga gag ccc aac gtc ctc atc tgt ttc atc gac aag ttc      336
Val Glu Leu Arg Glu Pro Asn Val Leu Ile Cys Phe Ile Asp Lys Phe
            100                 105                 110

acc cca cca gtg gtc aat gtc acg tgg ctt cga aat gga aaa cct gtc      384
Thr Pro Pro Val Val Asn Val Thr Trp Leu Arg Asn Gly Lys Pro Val
        115                 120                 125

acc aca gga gtg tca gag aca gtc ttc ctg ccc agg gat gac cac ctt      432
Thr Thr Gly Val Ser Glu Thr Val Phe Leu Pro Arg Asp Asp His Leu
    130                 135                 140

ttc cgc aag ttc cac tat ctc ccc ttc ctg ccc tca act gag gac gtt      480
Phe Arg Lys Phe His Tyr Leu Pro Phe Leu Pro Ser Thr Glu Asp Val
145                 150                 155                 160

tac gac tgc agg gtg gag cac tgg ggc ttg gat gag cct ctt ctc aag      528
Tyr Asp Cys Arg Val Glu His Trp Gly Leu Asp Glu Pro Leu Leu Lys
                165                 170                 175

cac tgg gag ttt gat gca cca agc cct ctc cca gag act aca gag aac      576
His Trp Glu Phe Asp Ala Pro Ser Pro Leu Pro Glu Thr Thr Glu Asn
            180                 185                 190

tta gga ggc ggc ggc tca ggt ggc ggc cgc tct ggc gga ggt gga tcc      624
Leu Gly Gly Gly Gly Ser Gly Gly Gly Arg Ser Gly Gly Gly Gly Ser
        195                 200                 205

ggg gac acc cga cca cgt ttc ttg tgg cag ctt aag ttt gaa tgt cat      672
Gly Asp Thr Arg Pro Arg Phe Leu Trp Gln Leu Lys Phe Glu Cys His
    210                 215                 220

ttc ttc aat ggg acg gag cgg gtg cgg ttt ctg gaa aga tgc atc tat      720
Phe Phe Asn Gly Thr Glu Arg Val Arg Phe Leu Glu Arg Cys Ile Tyr
225                 230                 235                 240

aac caa gag gag tcc gtg cgc ttc gac agc gac gtg ggg gag tac cgg      768
Asn Gln Glu Glu Ser Val Arg Phe Asp Ser Asp Val Gly Glu Tyr Arg
                245                 250                 255

gcg gtg acg gag ctg ggg cgg cct gat gcc gag tac tgg aac agc cag      816
Ala Val Thr Glu Leu Gly Arg Pro Asp Ala Glu Tyr Trp Asn Ser Gln
            260                 265                 270

aag gac ctc ctg gag cag agg cgg gcc gcg gcg gac acc tac tgc aga      864
Lys Asp Leu Leu Glu Gln Arg Arg Ala Ala Ala Asp Thr Tyr Cys Arg
        275                 280                 285

cac aac tac ggg gtt ggt gag agc ttc tca gtg cgg cgg cga gtt gag      912
His Asn Tyr Gly Val Gly Glu Ser Phe Ser Val Arg Arg Arg Val Glu
    290                 295                 300

cct aag gtg act gtg tat cct tca aag acc cag ccc ctg cag cac cac      960
Pro Lys Val Thr Val Tyr Pro Ser Lys Thr Gln Pro Leu Gln His His
305                 310                 315                 320

aac ctc ctg gtc tgc tct gtg agt ggt ttc tat cca ggc agc att gaa     1008
Asn Leu Leu Val Cys Ser Val Ser Gly Phe Tyr Pro Gly Ser Ile Glu
                325                 330                 335

gtc agg tgg ttc cgg aac ggc cag gaa gag aag gct ggg gtg gtg tcc     1056
Val Arg Trp Phe Arg Asn Gly Gln Glu Glu Lys Ala Gly Val Val Ser
            340                 345                 350

aca ggc ctg atc cag aat gga gat tgg acc ttc cag acc ctg gtg atg     1104
Thr Gly Leu Ile Gln Asn Gly Asp Trp Thr Phe Gln Thr Leu Val Met
        355                 360                 365
```

-continued

```
ctg gaa aca gtt cct cgg agt gga gag gtt tac acc tgc caa gtg gag      1152
Leu Glu Thr Val Pro Arg Ser Gly Glu Val Tyr Thr Cys Gln Val Glu
    370                 375                 380

cac cca agt gtg acg agc cct ctc aca gtg gaa tgg aga gca cgg tct      1200
His Pro Ser Val Thr Ser Pro Leu Thr Val Glu Trp Arg Ala Arg Ser
385                 390                 395                 400

gaa tct gca cag agc aag ctc gag tct aga ggg ccc ttc gaa ggt aag      1248
Glu Ser Ala Gln Ser Lys Leu Glu Ser Arg Gly Pro Phe Glu Gly Lys
                405                 410                 415

cct atc cct aac cct ctc ctc ggt ctc gat tct acg cgt acc ggt cat      1296
Pro Ile Pro Asn Pro Leu Leu Gly Leu Asp Ser Thr Arg Thr Gly His
            420                 425                 430

cat cac cat cac cat tga                                              1314
His His His His His
        435
```

<210> SEQ ID NO 35
<211> LENGTH: 437
<212> TYPE: PRT
<213> ORGANISM: Artificial sequence
<220> FEATURE:
<223> OTHER INFORMATION: Sequence of mutant DWP-5

<400> SEQUENCE: 35

```
Arg Lys Glu Glu His Val Ile Ile Gln Ala Glu Phe Tyr Leu Asn Pro
1               5                   10                  15

Asp Gln Ser Gly Glu Phe Met Phe Asp Phe Asp Gly Asp Glu Ile Phe
            20                  25                  30

His Val Asp Met Ala Lys Lys Glu Thr Val Trp Arg Leu Glu Glu Phe
        35                  40                  45

Gly Arg Phe Ala Ser Phe Glu Ala Gln Gly Ala Leu Ala Asn Ile Ala
    50                  55                  60

Val Asp Lys Ala Asn Leu Glu Ile Met Thr Lys Arg Ser Asn Tyr Thr
65                  70                  75                  80

Pro Ile Thr Asn Val Pro Pro Glu Val Thr Val Leu Thr Asn Ser Pro
                85                  90                  95

Val Glu Leu Arg Glu Pro Asn Val Leu Ile Cys Phe Ile Asp Lys Phe
            100                 105                 110

Thr Pro Pro Val Val Asn Val Thr Trp Leu Arg Asn Gly Lys Pro Val
        115                 120                 125

Thr Thr Gly Val Ser Glu Thr Val Phe Leu Pro Arg Asp Asp His Leu
    130                 135                 140

Phe Arg Lys Phe His Tyr Leu Pro Phe Leu Pro Ser Thr Glu Asp Val
145                 150                 155                 160

Tyr Asp Cys Arg Val Glu His Trp Gly Leu Asp Glu Pro Leu Leu Lys
                165                 170                 175

His Trp Glu Phe Asp Ala Pro Ser Pro Leu Pro Glu Thr Thr Glu Asn
            180                 185                 190

Leu Gly Gly Gly Gly Ser Gly Gly Gly Arg Ser Gly Gly Gly Ser
        195                 200                 205

Gly Asp Thr Arg Pro Arg Phe Leu Trp Gln Leu Lys Phe Glu Cys His
    210                 215                 220

Phe Phe Asn Gly Thr Glu Arg Val Arg Phe Leu Glu Arg Cys Ile Tyr
225                 230                 235                 240

Asn Gln Glu Glu Ser Val Arg Phe Asp Ser Asp Val Gly Glu Tyr Arg
                245                 250                 255

Ala Val Thr Glu Leu Gly Arg Pro Asp Ala Glu Tyr Trp Asn Ser Gln
```

-continued

```
        260                 265                 270

Lys Asp Leu Leu Glu Gln Arg Arg Ala Ala Ala Asp Thr Tyr Cys Arg
    275                 280                 285

His Asn Tyr Gly Val Gly Glu Ser Phe Ser Val Arg Arg Arg Val Glu
    290                 295                 300

Pro Lys Val Thr Val Tyr Pro Ser Lys Thr Gln Pro Leu Gln His His
305                 310                 315                 320

Asn Leu Leu Val Cys Ser Val Ser Gly Phe Tyr Pro Gly Ser Ile Glu
                325                 330                 335

Val Arg Trp Phe Arg Asn Gly Gln Glu Glu Lys Ala Gly Val Val Ser
            340                 345                 350

Thr Gly Leu Ile Gln Asn Gly Asp Trp Thr Phe Gln Thr Leu Val Met
        355                 360                 365

Leu Glu Thr Val Pro Arg Ser Gly Glu Val Tyr Thr Cys Gln Val Glu
    370                 375                 380

His Pro Ser Val Thr Ser Pro Leu Thr Val Glu Trp Arg Ala Arg Ser
385                 390                 395                 400

Glu Ser Ala Gln Ser Lys Leu Glu Ser Arg Gly Pro Phe Glu Gly Lys
                405                 410                 415

Pro Ile Pro Asn Pro Leu Leu Gly Leu Asp Ser Thr Arg Thr Gly His
            420                 425                 430

His His His His His
        435


<210> SEQ ID NO 36
<211> LENGTH: 1314
<212> TYPE: DNA
<213> ORGANISM: Artificial sequence
<220> FEATURE:
<223> OTHER INFORMATION: Sequence of mutant DWP-7
<220> FEATURE:
<221> NAME/KEY: CDS
<222> LOCATION: (1)..(1311)

<400> SEQUENCE: 36

agg aaa gaa gaa cat gtg atc acc cag gcc gag ttc tat ctg aat cct      48
Arg Lys Glu Glu His Val Ile Thr Gln Ala Glu Phe Tyr Leu Asn Pro
1               5                   10                  15

gac caa tca ggc gag ttt atg ttt gac ttt gat ggt gat gag att ttc      96
Asp Gln Ser Gly Glu Phe Met Phe Asp Phe Asp Gly Asp Glu Ile Phe
            20                  25                  30

cat gtg gat atg gca aag aag gag acg gtc tgg cgg ctt gaa gaa ttt     144
His Val Asp Met Ala Lys Lys Glu Thr Val Trp Arg Leu Glu Glu Phe
        35                  40                  45

gga cga ttt gcc agc ttt gag gct caa ggt gca ttg gcc aac ata gct     192
Gly Arg Phe Ala Ser Phe Glu Ala Gln Gly Ala Leu Ala Asn Ile Ala
    50                  55                  60

gtg gac aaa gcc aac ctg gaa atc atg aca aag cgc tcc aac tat act     240
Val Asp Lys Ala Asn Leu Glu Ile Met Thr Lys Arg Ser Asn Tyr Thr
65                  70                  75                  80

ccg atc acc aat gta cct cca gag gta act gtg ctc acg aac agc cct     288
Pro Ile Thr Asn Val Pro Pro Glu Val Thr Val Leu Thr Asn Ser Pro
                85                  90                  95

gtg gaa ctg aga gag ccc aac gtc ctc atc tgt tac atc gac aag ttc     336
Val Glu Leu Arg Glu Pro Asn Val Leu Ile Cys Tyr Ile Asp Lys Phe
            100                 105                 110

acc cca cca gtg gtc aat gtc acg tgg ctt cga aat gga aaa cct gtc     384
Thr Pro Pro Val Val Asn Val Thr Trp Leu Arg Asn Gly Lys Pro Val
        115                 120                 125
```

-continued

```
acc aca gga gtg tca gag aca gtc ttc ctg ccc agg gaa gac cac ctt       432
Thr Thr Gly Val Ser Glu Thr Val Phe Leu Pro Arg Glu Asp His Leu
    130                 135                 140

ttc cgc aag ttc cac tat ctc ccc ttc ctg ccc tca act gag gac gtt       480
Phe Arg Lys Phe His Tyr Leu Pro Phe Leu Pro Ser Thr Glu Asp Val
145                 150                 155                 160

tac gac tgc agg gtg gag cac tgg ggc ttg gat gag cct ctt ctc aag       528
Tyr Asp Cys Arg Val Glu His Trp Gly Leu Asp Glu Pro Leu Leu Lys
                165                 170                 175

cac tgg gag ttt aat gca cca agc cct ctc cca gag act aca gag aac       576
His Trp Glu Phe Asn Ala Pro Ser Pro Leu Pro Glu Thr Thr Glu Asn
            180                 185                 190

tta gga ggc ggc ggc tca ggt ggc ggc cgc tct ggc gga ggt gga tcc       624
Leu Gly Gly Gly Gly Ser Gly Gly Gly Arg Ser Gly Gly Gly Gly Ser
        195                 200                 205

ggg gac acc cga cca cgt ttc ttg tgg cag cat aag ttt gaa tgt cat       672
Gly Asp Thr Arg Pro Arg Phe Leu Trp Gln His Lys Phe Glu Cys His
    210                 215                 220

ttc ttc aat ggg acg gag cgg gtg cgg ttg ctg gaa aga tgc atc tat       720
Phe Phe Asn Gly Thr Glu Arg Val Arg Leu Leu Glu Arg Cys Ile Tyr
225                 230                 235                 240

aac caa gag gag tcc gtg cgc ttc gac agc gac gtg ggg gag tac cgg       768
Asn Gln Glu Glu Ser Val Arg Phe Asp Ser Asp Val Gly Glu Tyr Arg
                245                 250                 255

gcg gtg acg gag ctg ggg cgg cct gct gcc gag tac tgg aac agc cag       816
Ala Val Thr Glu Leu Gly Arg Pro Ala Ala Glu Tyr Trp Asn Ser Gln
            260                 265                 270

aag gac ctc ctg gag cag agg cgg gcc gcg gcg gac acc tac tgc aga       864
Lys Asp Leu Leu Glu Gln Arg Arg Ala Ala Ala Asp Thr Tyr Cys Arg
        275                 280                 285

cac aac tac ggg gtt ggt gag agc ttc aca gtg cgg cgg cga gtt gag       912
His Asn Tyr Gly Val Gly Glu Ser Phe Thr Val Arg Arg Arg Val Glu
    290                 295                 300

cct aag gtg act gtg tat cct tca aag acc cag ccc ctg cag cac cac       960
Pro Lys Val Thr Val Tyr Pro Ser Lys Thr Gln Pro Leu Gln His His
305                 310                 315                 320

aac ctc ctg gtc tgc tct gtg agt ggt ttc tat cca ggc agc att gaa      1008
Asn Leu Leu Val Cys Ser Val Ser Gly Phe Tyr Pro Gly Ser Ile Glu
                325                 330                 335

gtc agg tgg ttc cgg aac ggc cag gaa gag aag gct ggg gtg gtg tcc      1056
Val Arg Trp Phe Arg Asn Gly Gln Glu Glu Lys Ala Gly Val Val Ser
            340                 345                 350

aca ggc ctg atc cag aat gga gat tgg acc ttc cag acc ctg gtg atg      1104
Thr Gly Leu Ile Gln Asn Gly Asp Trp Thr Phe Gln Thr Leu Val Met
        355                 360                 365

ctg gaa aca gtt cct cgg agt gga gag gtt tac acc tgc caa gtg gag      1152
Leu Glu Thr Val Pro Arg Ser Gly Glu Val Tyr Thr Cys Gln Val Glu
    370                 375                 380

cac cca agt gtg acg agc cct ctc aca gtg gaa tgg aga gca cgg tct      1200
His Pro Ser Val Thr Ser Pro Leu Thr Val Glu Trp Arg Ala Arg Ser
385                 390                 395                 400

gaa tct gca cag agc aag ctc gag tct aga ggg ccc ttc gaa ggt aag      1248
Glu Ser Ala Gln Ser Lys Leu Glu Ser Arg Gly Pro Phe Glu Gly Lys
                405                 410                 415

cct atc cct aac cct ctc ctc ggt ctc gat tct acg cgt acc ggt cat      1296
Pro Ile Pro Asn Pro Leu Leu Gly Leu Asp Ser Thr Arg Thr Gly His
            420                 425                 430

cat cac cat cac cat tga                                              1314
His His His His His
```

435

<210> SEQ ID NO 37
<211> LENGTH: 437
<212> TYPE: PRT
<213> ORGANISM: Artificial sequence
<220> FEATURE:
<223> OTHER INFORMATION: Sequence of mutant DWP-7

<400> SEQUENCE: 37

Arg Lys Glu Glu His Val Ile Thr Gln Ala Glu Phe Tyr Leu Asn Pro
1 5 10 15

Asp Gln Ser Gly Glu Phe Met Phe Asp Phe Asp Gly Asp Glu Ile Phe
20 25 30

His Val Asp Met Ala Lys Lys Glu Thr Val Trp Arg Leu Glu Glu Phe
35 40 45

Gly Arg Phe Ala Ser Phe Glu Ala Gln Gly Ala Leu Ala Asn Ile Ala
50 55 60

Val Asp Lys Ala Asn Leu Glu Ile Met Thr Lys Arg Ser Asn Tyr Thr
65 70 75 80

Pro Ile Thr Asn Val Pro Pro Glu Val Thr Val Leu Thr Asn Ser Pro
85 90 95

Val Glu Leu Arg Glu Pro Asn Val Leu Ile Cys Tyr Ile Asp Lys Phe
100 105 110

Thr Pro Pro Val Val Asn Val Thr Trp Leu Arg Asn Gly Lys Pro Val
115 120 125

Thr Thr Gly Val Ser Glu Thr Val Phe Leu Pro Arg Glu Asp His Leu
130 135 140

Phe Arg Lys Phe His Tyr Leu Pro Phe Leu Pro Ser Thr Glu Asp Val
145 150 155 160

Tyr Asp Cys Arg Val Glu His Trp Gly Leu Asp Glu Pro Leu Leu Lys
165 170 175

His Trp Glu Phe Asn Ala Pro Ser Pro Leu Pro Glu Thr Thr Glu Asn
180 185 190

Leu Gly Gly Gly Gly Ser Gly Gly Gly Arg Ser Gly Gly Gly Gly Ser
195 200 205

Gly Asp Thr Arg Pro Arg Phe Leu Trp Gln His Lys Phe Glu Cys His
210 215 220

Phe Phe Asn Gly Thr Glu Arg Val Arg Leu Leu Glu Arg Cys Ile Tyr
225 230 235 240

Asn Gln Glu Glu Ser Val Arg Phe Asp Ser Asp Val Gly Glu Tyr Arg
245 250 255

Ala Val Thr Glu Leu Gly Arg Pro Ala Ala Glu Tyr Trp Asn Ser Gln
260 265 270

Lys Asp Leu Leu Glu Gln Arg Arg Ala Ala Ala Asp Thr Tyr Cys Arg
275 280 285

His Asn Tyr Gly Val Gly Glu Ser Phe Thr Val Arg Arg Arg Val Glu
290 295 300

Pro Lys Val Thr Val Tyr Pro Ser Lys Thr Gln Pro Leu Gln His His
305 310 315 320

Asn Leu Leu Val Cys Ser Val Ser Gly Phe Tyr Pro Gly Ser Ile Glu
325 330 335

Val Arg Trp Phe Arg Asn Gly Gln Glu Glu Lys Ala Gly Val Val Ser
340 345 350

Thr Gly Leu Ile Gln Asn Gly Asp Trp Thr Phe Gln Thr Leu Val Met

```
        355                 360                 365

Leu Glu Thr Val Pro Arg Ser Gly Glu Val Tyr Thr Cys Gln Val Glu
    370                 375                 380

His Pro Ser Val Thr Ser Pro Leu Thr Val Glu Trp Arg Ala Arg Ser
385                 390                 395                 400

Glu Ser Ala Gln Ser Lys Leu Glu Ser Arg Gly Pro Phe Glu Gly Lys
                405                 410                 415

Pro Ile Pro Asn Pro Leu Leu Gly Leu Asp Ser Thr Arg Thr Gly His
            420                 425                 430

His His His His His
        435


<210> SEQ ID NO 38
<211> LENGTH: 552
<212> TYPE: DNA
<213> ORGANISM: Homo sapiens
<220> FEATURE:
<221> NAME/KEY: CDS
<222> LOCATION: (1)..(552)

<400> SEQUENCE: 38

ggg gac acc cga cca cgt ttc ttg tgg cag ctt aag ttt gaa tgt cat       48
Gly Asp Thr Arg Pro Arg Phe Leu Trp Gln Leu Lys Phe Glu Cys His
1               5                   10                  15

ttc ttc aat ggg acg gag cgg gtg cgg ttg ctg gaa aga tgc atc tat       96
Phe Phe Asn Gly Thr Glu Arg Val Arg Leu Leu Glu Arg Cys Ile Tyr
            20                  25                  30

aac caa gag gag tcc gtg cgc ttc gac agc gac gtg ggg gag tac cgg      144
Asn Gln Glu Glu Ser Val Arg Phe Asp Ser Asp Val Gly Glu Tyr Arg
        35                  40                  45

gcg gtg acg gag ctg ggg cgg cct gat gcc gag tac tgg aac agc cag      192
Ala Val Thr Glu Leu Gly Arg Pro Asp Ala Glu Tyr Trp Asn Ser Gln
    50                  55                  60

aag gac ctc ctg gag cag agg cgg gcc gcg gtg gac acc tac tgc aga      240
Lys Asp Leu Leu Glu Gln Arg Arg Ala Ala Val Asp Thr Tyr Cys Arg
65                  70                  75                  80

cac aac tac ggg gtt ggt gag agc ttc aca gtg cag cgg cga gtt ggc      288
His Asn Tyr Gly Val Gly Glu Ser Phe Thr Val Gln Arg Arg Val Gly
                85                  90                  95

tca gga ggt act agt aaa gaa gaa cat gtg atc atc cag gcc gag ttc      336
Ser Gly Gly Thr Ser Lys Glu Glu His Val Ile Ile Gln Ala Glu Phe
            100                 105                 110

tat ctg aat cct gac caa tca ggc gag ttt atg ttt gac ttt gat ggt      384
Tyr Leu Asn Pro Asp Gln Ser Gly Glu Phe Met Phe Asp Phe Asp Gly
        115                 120                 125

gat gag att ttc cat gtg gat atg gca aag aag gag acg gtc tgg cgg      432
Asp Glu Ile Phe His Val Asp Met Ala Lys Lys Glu Thr Val Trp Arg
    130                 135                 140

ctt gaa gaa ttt gga cga ttt gcc agc ttt gag gct caa ggt gca ttg      480
Leu Glu Glu Phe Gly Arg Phe Ala Ser Phe Glu Ala Gln Gly Ala Leu
145                 150                 155                 160

gcc aac ata gct gtg gac aaa gcc aac ctg gaa atc atg aca aag cgc      528
Ala Asn Ile Ala Val Asp Lys Ala Asn Leu Glu Ile Met Thr Lys Arg
                165                 170                 175

tcc aac tat act ccg atc acc aat                                      552
Ser Asn Tyr Thr Pro Ile Thr Asn
            180


<210> SEQ ID NO 39
<211> LENGTH: 184
```

-continued

<212> TYPE: PRT
<213> ORGANISM: Homo sapiens

<400> SEQUENCE: 39

Gly Asp Thr Arg Pro Arg Phe Leu Trp Gln Leu Lys Phe Glu Cys His
1               5                   10                  15

Phe Phe Asn Gly Thr Glu Arg Val Arg Leu Leu Glu Arg Cys Ile Tyr
            20                  25                  30

Asn Gln Glu Glu Ser Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Arg Arg Ala Ala Val Asp Thr Tyr Cys Arg
65                  70                  75                  80

His Asn Tyr Gly Val Gly Glu Ser Phe Thr Val Gln Arg Arg Val Gly
                85                  90                  95

Ser Gly Gly Thr Ser Lys Glu Glu His Val Ile Ile Gln Ala Glu Phe
            100                 105                 110

Tyr Leu Asn Pro Asp Gln Ser Gly Glu Phe Met Phe Asp Phe Asp Gly
        115                 120                 125

Asp Glu Ile Phe His Val Asp Met Ala Lys Lys Glu Thr Val Trp Arg
    130                 135                 140

Leu Glu Glu Phe Gly Arg Phe Ala Ser Phe Glu Ala Gln Gly Ala Leu
145                 150                 155                 160

Ala Asn Ile Ala Val Asp Lys Ala Asn Leu Glu Ile Met Thr Lys Arg
                165                 170                 175

Ser Asn Tyr Thr Pro Ile Thr Asn
            180

<210> SEQ ID NO 40
<211> LENGTH: 552
<212> TYPE: DNA
<213> ORGANISM: Artificial sequence
<220> FEATURE:
<223> OTHER INFORMATION: Sequence of single chain beta1alpha1 mutant

<400> SEQUENCE: 40
ggggacaccc gaccacgttt cttgtggcag cataagtttg aatgtcattt cttcaatggg 60
acggagcggg tgcggttgct ggaaagatgc atctataacc aagaggagtc cgtgcgcttc 120
gacagcgacg tgggggagta ccgggcggtg acggagctgg ggcggcctga tgccgagtac 180
tggaacagcc agaaggacct cctggagcag aggcgggccg cggtggacac ctactgcaga 240
cacaactacg ggttggtga gagcttcaca gtgcagcggc gagttggctc aggaggtact 300
agtaaagaag aacatgtgat cacccaggcc gagttctatc tgaatcctga ccaatcaggc 360
gagtttatgt ttgactttga tggtgatgag attttccatg tggatatggc aaagaaggag 420
acggtctggc ggcttgaaga atttggacga tttgccagct ttgaggctca aggtgcattg 480
gccaacatag ctgtggacaa agccaacctg gaaatcatga caaagcgctc caactatact 540
ccgatcacca at 552

<210> SEQ ID NO 41
<211> LENGTH: 1266
<212> TYPE: DNA
<213> ORGANISM: Artificial sequence
<220> FEATURE:
<223> OTHER INFORMATION: Sequence of sc HLA-A2 variant
<220> FEATURE:

-continued

<221> NAME/KEY: CDS
<222> LOCATION: (1)..(1263)

<400> SEQUENCE: 41

```
atg atc cag cgt act cca aag att cag gtt tac tca cgt cat cca gca       48
Met Ile Gln Arg Thr Pro Lys Ile Gln Val Tyr Ser Arg His Pro Ala
1               5                   10                  15

gag aat gga aag tca aat ttc ctg aat tgc tat gtg tct ggg ttt cat       96
Glu Asn Gly Lys Ser Asn Phe Leu Asn Cys Tyr Val Ser Gly Phe His
            20                  25                  30

cca tcc gac att gaa gtt gac tta ctg aag aat gga gag aga att gaa      144
Pro Ser Asp Ile Glu Val Asp Leu Leu Lys Asn Gly Glu Arg Ile Glu
        35                  40                  45

aaa gtg gag cat tca gac ttg tct ttc agc aag gac tgg tct ttc tat      192
Lys Val Glu His Ser Asp Leu Ser Phe Ser Lys Asp Trp Ser Phe Tyr
    50                  55                  60

ctc ttg tac tac act gaa ttc acc ccc act gaa aaa gat gag tat gcc      240
Leu Leu Tyr Tyr Thr Glu Phe Thr Pro Thr Glu Lys Asp Glu Tyr Ala
65                  70                  75                  80

tgc cgt gtg aac cat gtg act ttg tca cag ccc gag ata gtt aag tgg      288
Cys Arg Val Asn His Val Thr Leu Ser Gln Pro Glu Ile Val Lys Trp
                85                  90                  95

gat cga gac atg gga ggc ggc ggc tcg ggt ggc ggc ggc tct ggc gga      336
Asp Arg Asp Met Gly Gly Gly Gly Ser Gly Gly Gly Gly Ser Gly Gly
            100                 105                 110

ggt gga tcc ggc tct cac tcc atg agg tat ttc ttc aca tcc gtg tcc      384
Gly Gly Ser Gly Ser His Ser Met Arg Tyr Phe Phe Thr Ser Val Ser
        115                 120                 125

cgg ccc ggc cgc ggg gag ccc cgc ttc atc gca gtg ggc tac gtg gac      432
Arg Pro Gly Arg Gly Glu Pro Arg Phe Ile Ala Val Gly Tyr Val Asp
    130                 135                 140

gac acg cag ttc gtg cgg ttc gac agc gac gcc gcg agc cag agg atg      480
Asp Thr Gln Phe Val Arg Phe Asp Ser Asp Ala Ala Ser Gln Arg Met
145                 150                 155                 160

gag ccg cgg gcg ccg tgg ata gag cag gag ggt ccg gag tat tgg gac      528
Glu Pro Arg Ala Pro Trp Ile Glu Gln Glu Gly Pro Glu Tyr Trp Asp
                165                 170                 175

ggg gag aca cgg aaa gtg aag gcc cac tca cag act cac cga gtg gac      576
Gly Glu Thr Arg Lys Val Lys Ala His Ser Gln Thr His Arg Val Asp
            180                 185                 190

ctg ggg acc ctg cgc ggc tac tac aac cag agc gag gcc ggt tct cac      624
Leu Gly Thr Leu Arg Gly Tyr Tyr Asn Gln Ser Glu Ala Gly Ser His
        195                 200                 205

acc gtc cag agg atg tat ggc tgc gac gtg ggg tcg gac tgg cgc ttc      672
Thr Val Gln Arg Met Tyr Gly Cys Asp Val Gly Ser Asp Trp Arg Phe
    210                 215                 220

ctc cgc ggg tac cac cag tac gcc tac gac ggc aag gat tac atc gcc      720
Leu Arg Gly Tyr His Gln Tyr Ala Tyr Asp Gly Lys Asp Tyr Ile Ala
225                 230                 235                 240

ctg aaa gag gac ctg cgc tct tgg acc gcg gcg gac atg gca gct cag      768
Leu Lys Glu Asp Leu Arg Ser Trp Thr Ala Ala Asp Met Ala Ala Gln
                245                 250                 255

acc acc aag cac aag tgg gag gcg gcc cat gtg gcg gag cag ttg aga      816
Thr Thr Lys His Lys Trp Glu Ala Ala His Val Ala Glu Gln Leu Arg
            260                 265                 270

gcc tac ctg gag ggc acg tgc gtg gag tgg ctc cgc aga tac ctg gag      864
Ala Tyr Leu Glu Gly Thr Cys Val Glu Trp Leu Arg Arg Tyr Leu Glu
        275                 280                 285

aac ggg aag gag acg ctg cag cgc acg gac gcc ccc aaa acg cat atg      912
Asn Gly Lys Glu Thr Leu Gln Arg Thr Asp Ala Pro Lys Thr His Met
```

-continued

```
    290                 295                 300

act cac cac gct gtc tct gac cat gaa gcc acc ctg agg tgc tgg gcc      960
Thr His His Ala Val Ser Asp His Glu Ala Thr Leu Arg Cys Trp Ala
305                 310                 315                 320

ctg agc ttc tac cct gcg gag atc aca ctg acc tgg cag cgg gat ggg     1008
Leu Ser Phe Tyr Pro Ala Glu Ile Thr Leu Thr Trp Gln Arg Asp Gly
                325                 330                 335

gag gac cag acc cag gac acg gag ctc gtg gag acc agg cct gca ggg     1056
Glu Asp Gln Thr Gln Asp Thr Glu Leu Val Glu Thr Arg Pro Ala Gly
            340                 345                 350

gat gga acc ttc cag aag tgg gcg gct gtg gtg gtg cct tct gga cag     1104
Asp Gly Thr Phe Gln Lys Trp Ala Ala Val Val Val Pro Ser Gly Gln
        355                 360                 365

gag cag aga tac acc tgc cat gtg cag cat gag ggt ttg ccc aag ccc     1152
Glu Gln Arg Tyr Thr Cys His Val Gln His Glu Gly Leu Pro Lys Pro
    370                 375                 380

ctc acc ctg aga tgg gaa ctc gag tct aga ggg ccc ttc gaa ggt aag     1200
Leu Thr Leu Arg Trp Glu Leu Glu Ser Arg Gly Pro Phe Glu Gly Lys
385                 390                 395                 400

cct atc cct aac cct ctc ctc ggt ctc gat tct acg cgt acc ggt cat     1248
Pro Ile Pro Asn Pro Leu Leu Gly Leu Asp Ser Thr Arg Thr Gly His
                405                 410                 415

cat cac cat cac cat tga                                             1266
His His His His His
            420


<210> SEQ ID NO 42
<211> LENGTH: 421
<212> TYPE: PRT
<213> ORGANISM: Artificial sequence
<220> FEATURE:
<223> OTHER INFORMATION: Sequence of sc HLA-A2 variant

<400> SEQUENCE: 42

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Glu Ile Val Lys Trp
                85                  90                  95

Asp Arg Asp Met Gly Gly Gly Gly Ser Gly Gly Gly Gly Ser Gly Gly
            100                 105                 110

Gly Gly Ser Gly Ser His Ser Met Arg Tyr Phe Phe Thr Ser Val Ser
        115                 120                 125

Arg Pro Gly Arg Gly Glu Pro Arg Phe Ile Ala Val Gly Tyr Val Asp
    130                 135                 140

Asp Thr Gln Phe Val Arg Phe Asp Ser Asp Ala Ala Ser Gln Arg Met
145                 150                 155                 160

Glu Pro Arg Ala Pro Trp Ile Glu Gln Glu Gly Pro Glu Tyr Trp Asp
                165                 170                 175

Gly Glu Thr Arg Lys Val Lys Ala His Ser Gln Thr His Arg Val Asp
            180                 185                 190
```

```
Leu Gly Thr Leu Arg Gly Tyr Tyr Asn Gln Ser Glu Ala Gly Ser His
        195                 200                 205

Thr Val Gln Arg Met Tyr Gly Cys Asp Val Gly Ser Asp Trp Arg Phe
    210                 215                 220

Leu Arg Gly Tyr His Gln Tyr Ala Tyr Asp Gly Lys Asp Tyr Ile Ala
225                 230                 235                 240

Leu Lys Glu Asp Leu Arg Ser Trp Thr Ala Ala Asp Met Ala Ala Gln
                245                 250                 255

Thr Thr Lys His Lys Trp Glu Ala Ala His Val Ala Glu Gln Leu Arg
            260                 265                 270

Ala Tyr Leu Glu Gly Thr Cys Val Glu Trp Leu Arg Arg Tyr Leu Glu
        275                 280                 285

Asn Gly Lys Glu Thr Leu Gln Arg Thr Asp Ala Pro Lys Thr His Met
    290                 295                 300

Thr His His Ala Val Ser Asp His Glu Ala Thr Leu Arg Cys Trp Ala
305                 310                 315                 320

Leu Ser Phe Tyr Pro Ala Glu Ile Thr Leu Thr Trp Gln Arg Asp Gly
                325                 330                 335

Glu Asp Gln Thr Gln Asp Thr Glu Leu Val Glu Thr Arg Pro Ala Gly
            340                 345                 350

Asp Gly Thr Phe Gln Lys Trp Ala Ala Val Val Val Pro Ser Gly Gln
        355                 360                 365

Glu Gln Arg Tyr Thr Cys His Val Gln His Glu Gly Leu Pro Lys Pro
    370                 375                 380

Leu Thr Leu Arg Trp Glu Leu Glu Ser Arg Gly Pro Phe Glu Gly Lys
385                 390                 395                 400

Pro Ile Pro Asn Pro Leu Leu Gly Leu Asp Ser Thr Arg Thr Gly His
                405                 410                 415

His His His His His
            420


<210> SEQ ID NO 43
<211> LENGTH: 543
<212> TYPE: DNA
<213> ORGANISM: Artificial sequence
<220> FEATURE:
<223> OTHER INFORMATION: Sequence of sc HLA-A2 variant called pbsHLA-A2
<220> FEATURE:
<221> NAME/KEY: CDS
<222> LOCATION: (1)..(543)

<400> SEQUENCE: 43

atg ggc tct cac tcc atg agg tat ttc ttc aca tcc gtg tcc cgg ccc       48
Met Gly Ser His Ser Met Arg Tyr Phe Phe Thr Ser Val Ser Arg Pro
1               5                   10                  15

ggc cgc ggg gag ccc cgc ttc atc gca gtg ggc tac gtg gac gac acg       96
Gly Arg Gly Glu Pro Arg Phe Ile Ala Val Gly Tyr Val Asp Asp Thr
            20                  25                  30

cag ttc gtg cgg ttc gac agc gac gcc gcg agc cag agg atg gag ccg      144
Gln Phe Val Arg Phe Asp Ser Asp Ala Ala Ser Gln Arg Met Glu Pro
        35                  40                  45

cgg gcg ccg tgg ata gag cag gag ggt ccg gag tat tgg gac ggg gag      192
Arg Ala Pro Trp Ile Glu Gln Glu Gly Pro Glu Tyr Trp Asp Gly Glu
    50                  55                  60

aca cgg aaa gtg aag gcc cac tca cag act cac cga gtg gac ctg ggg      240
Thr Arg Lys Val Lys Ala His Ser Gln Thr His Arg Val Asp Leu Gly
65                  70                  75                  80
```

```
acc ctg cgc ggc tac tac aac cag agc gag gcc ggt tct cac acc gtc      288
Thr Leu Arg Gly Tyr Tyr Asn Gln Ser Glu Ala Gly Ser His Thr Val
                85                  90                  95

cag agg atg tat ggc tgc gac gtg ggg tcg gac tgg cgc ttc ctc cgc      336
Gln Arg Met Tyr Gly Cys Asp Val Gly Ser Asp Trp Arg Phe Leu Arg
            100                 105                 110

ggg tac cac cag tac gcc tac gac ggc aag gat tac atc gcc ctg aaa      384
Gly Tyr His Gln Tyr Ala Tyr Asp Gly Lys Asp Tyr Ile Ala Leu Lys
        115                 120                 125

gag gac ctg cgc tct tgg acc gcg gcg gac atg gca gct cag acc acc      432
Glu Asp Leu Arg Ser Trp Thr Ala Ala Asp Met Ala Ala Gln Thr Thr
    130                 135                 140

aag cac aag tgg gag gcg gcc cat gtg gcg gag cag ttg aga gcc tac      480
Lys His Lys Trp Glu Ala Ala His Val Ala Glu Gln Leu Arg Ala Tyr
145                 150                 155                 160

ctg gag ggc acg tgc gtg gag tgg ctc cgc aga tac ctg gag aac ggg      528
Leu Glu Gly Thr Cys Val Glu Trp Leu Arg Arg Tyr Leu Glu Asn Gly
                165                 170                 175

aag gag acg ctg cag                                                  543
Lys Glu Thr Leu Gln
            180


<210> SEQ ID NO 44
<211> LENGTH: 181
<212> TYPE: PRT
<213> ORGANISM: Artificial sequence
<220> FEATURE:
<223> OTHER INFORMATION: Sequence of sc HLA-A2 variant called pbsHLA-A2

<400> SEQUENCE: 44

Met Gly Ser His Ser Met Arg Tyr Phe Phe Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Gly Glu
    50                  55                  60

Thr Arg Lys Val Lys Ala His Ser Gln Thr His Arg Val Asp Leu Gly
65                  70                  75                  80

Thr Leu Arg Gly Tyr Tyr Asn Gln Ser Glu Ala Gly Ser His Thr Val
                85                  90                  95

Gln Arg Met Tyr Gly Cys Asp Val Gly Ser Asp Trp Arg Phe Leu Arg
            100                 105                 110

Gly Tyr His Gln Tyr Ala Tyr Asp Gly Lys Asp Tyr Ile Ala Leu Lys
        115                 120                 125

Glu Asp Leu Arg Ser Trp Thr Ala Ala Asp Met Ala Ala Gln Thr Thr
    130                 135                 140

Lys His Lys Trp Glu Ala Ala His Val Ala Glu Gln Leu Arg Ala Tyr
145                 150                 155                 160

Leu Glu Gly Thr Cys Val Glu Trp Leu Arg Arg Tyr Leu Glu Asn Gly
                165                 170                 175

Lys Glu Thr Leu Gln
            180


<210> SEQ ID NO 45
<211> LENGTH: 15
<212> TYPE: PRT
<213> ORGANISM: Artificial sequence
```

-continued

```
<220> FEATURE:
<223> OTHER INFORMATION: Synthetic peptide linker

<400> SEQUENCE: 45

Gly Gly Gly Gly Ser Gly Gly Gly Arg Ser Gly Gly Gly Gly Ser
1               5                   10                  15


<210> SEQ ID NO 46
<211> LENGTH: 5
<212> TYPE: PRT
<213> ORGANISM: Artificial sequence
<220> FEATURE:
<223> OTHER INFORMATION: Synthetic linker peptide

<400> SEQUENCE: 46

Gly Ser Gly Gly Thr
1               5


<210> SEQ ID NO 47
<211> LENGTH: 9
<212> TYPE: PRT
<213> ORGANISM: Artificial sequence
<220> FEATURE:
<223> OTHER INFORMATION: Synthetic peptide

<400> SEQUENCE: 47

Ile Leu Lys Glu Cys Val His Gly Val
1               5
```